US009101928B2

(12) United States Patent
Mehta et al.

(10) Patent No.: US 9,101,928 B2
(45) Date of Patent: Aug. 11, 2015

(54) MANIPULATION OF MICROPARTICLES IN MICROFLUIDIC SYSTEMS

(75) Inventors: Tammy Burd Mehta, San Jose, CA (US); Anne R. Kopf-Sill, Portola Valley, CA (US); J. Wallace Parce, Palo Alto, CA (US); Andrea W. Chow, Los Altos, CA (US); Luc J. Bousse, Los Altos, CA (US); Michael R. Knapp, Palo Alto, CA (US); Theo T. Nikiforov, San Jose, CA (US); Steve Gallagher, Palo Alto, CA (US)

(73) Assignee: Caliper Life Sciences, Inc., Hopkinton, MA (US)

( * ) Notice: Subject to any disclaimer, the term of this patent is extended or adjusted under 35 U.S.C. 154(b) by 184 days.

(21) Appl. No.: 13/015,242

(22) Filed: Jan. 27, 2011

(65) Prior Publication Data

US 2011/0118139 A1    May 19, 2011

Related U.S. Application Data

(60) Continuation of application No. 11/928,808, filed on Oct. 30, 2007, now abandoned, which is a division of application No. 10/606,201, filed on Jun. 25, 2003, now abandoned, which is a continuation of application No. 09/510,626, filed on Feb. 22, 2000, now Pat. No. 6,632,655.

(60) Provisional application No. 60/121,223, filed on Feb. 23, 1999, provisional application No. 60/127,825, filed on Apr. 5, 1999, provisional application No. 60/128,643, filed on Apr. 9, 1999.

(51) Int. Cl.
| | |
|---|---|
| G01N 35/00 | (2006.01) |
| B01L 3/00 | (2006.01) |
| C07H 21/02 | (2006.01) |
| C07H 21/04 | (2006.01) |
| C12Q 1/68 | (2006.01) |
| B01F 13/00 | (2006.01) |
| C40B 60/14 | (2006.01) |
| G01N 27/447 | (2006.01) |

(52) U.S. Cl.
CPC ......... *B01L 3/5027* (2013.01); *B01L 3/502761* (2013.01); *C07H 21/02* (2013.01); *C07H 21/04* (2013.01); *C12Q 1/6869* (2013.01); *B01F 13/0059* (2013.01); *B01J 2219/00317* (2013.01); *B01J 2219/00459* (2013.01); *B01J 2219/00468* (2013.01); *B01L 3/502715* (2013.01); *B01L 2200/0668* (2013.01); *B01L 2400/043* (2013.01); *B01L 2400/0409* (2013.01); *B01L 2400/0415* (2013.01); *B01L 2400/0487* (2013.01); *C40B 60/14* (2013.01); *G01N 27/44756* (2013.01); *G01N 35/0098* (2013.01); *G01N 2035/00574* (2013.01); *Y10T 436/143333* (2015.01)

(58) Field of Classification Search
None
See application file for complete search history.

(56) References Cited

U.S. PATENT DOCUMENTS

| | | |
|---|---|---|
| 4,390,403 A | 6/1983 | Batchelder |
| 4,863,849 A | 9/1989 | Melamede |
| 4,908,112 A | 3/1990 | Pace |
| 4,971,903 A | 11/1990 | Hyman |
| 5,122,614 A | 6/1992 | Zalipsky |
| 5,126,022 A | 6/1992 | Soane et al. |
| 5,187,085 A | 2/1993 | Lee |
| 5,202,231 A | 4/1993 | Drmanac et al. |
| 5,302,509 A | 4/1994 | Cheeseman |
| 5,304,487 A | 4/1994 | Wilding et al. |
| 5,332,666 A | 7/1994 | Prober et al. |
| 5,498,392 A | 3/1996 | Wilding et al. |
| 5,525,711 A | 6/1996 | Hawkins et al. |
| 5,571,410 A | 11/1996 | Swedberg et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,595,001 A | 1/1997 | Schutte et al. |
| 5,603,351 A | 2/1997 | Cherukuri et al. |
| 5,635,358 A | 6/1997 | Wilding et al. |
| 5,637,469 A | 6/1997 | Wilding et al. |
| 5,650,234 A | 7/1997 | Dolence et al. |
| 5,653,939 A | 8/1997 | Hollis et al. |
| 5,699,157 A | 12/1997 | Parce |
| 5,719,060 A | 2/1998 | Hutchens et al. |

(Continued)

FOREIGN PATENT DOCUMENTS

| | | |
|---|---|---|
| EP | 0376611 A2 | 7/1990 |
| EP | 0620432 A1 | 10/1994 |

(Continued)

OTHER PUBLICATIONS

Maxam & Gilbert (1977 PNAS 74:560-564).*

(Continued)

*Primary Examiner* — Christopher M Gross
(74) *Attorney, Agent, or Firm* — Cardinal Law Group

(57) ABSTRACT

An array of transportable particle sets is used in a microfluidic device for performing chemical reactions in the microfluidic device. The microfluidic device comprises a main channel and intersecting side channels, the main channel and side channels forming a plurality of intersections. The array of particle sets is disposed in the main channel, and the side channels are coupled to reagents. As the particle sets are transported through the intersections of the main channel and the side channels, reagents are flowed through the side channels into contact with each array member (or selected array members), thereby providing a plurality of chemical reactions in the microfluidic system.

18 Claims, 19 Drawing Sheets

(56) References Cited

U.S. PATENT DOCUMENTS

| | | | |
|---|---|---|---|
| 5,747,349 A | 5/1998 | van den Engh et al. | |
| 5,750,015 A * | 5/1998 | Soane et al. | 204/454 |
| 5,755,942 A | 5/1998 | Zanzucchi et al. | |
| 5,779,868 A | 7/1998 | Parce et al. | |
| 5,798,210 A | 8/1998 | Canard et al. | |
| 5,800,690 A | 9/1998 | Chow et al. | |
| 5,842,787 A | 12/1998 | Kopf-Sill et al. | |
| 5,852,495 A | 12/1998 | Parce | |
| 5,856,174 A | 1/1999 | Lipshutz et al. | |
| 5,858,195 A | 1/1999 | Ramsey | |
| 5,863,502 A | 1/1999 | Southgate et al. | |
| 5,869,004 A | 2/1999 | Parce et al. | |
| 5,876,675 A | 3/1999 | Kennedy | |
| 5,880,071 A | 3/1999 | Parce et al. | |
| 5,882,465 A | 3/1999 | McReynolds | |
| 5,885,470 A | 3/1999 | Parce et al. | |
| 5,942,443 A | 8/1999 | Parce et al. | |
| 5,948,227 A | 9/1999 | Dubrow | |
| 5,955,028 A | 9/1999 | Chow | |
| 5,957,579 A | 9/1999 | Kopf-Sill et al. | |
| 5,958,203 A | 9/1999 | Parce et al. | |
| 5,958,694 A | 9/1999 | Nikiforov | |
| 5,959,291 A | 9/1999 | Jensen | |
| 5,964,995 A | 10/1999 | Nikiforov et al. | |
| 5,965,410 A | 10/1999 | Chow et al. | |
| 5,972,187 A | 10/1999 | Parce et al. | |
| 5,976,336 A | 11/1999 | Dubrow et al. | |
| 5,981,180 A | 11/1999 | Chandler et al. | |
| 5,989,402 A | 11/1999 | Chow et al. | |
| 6,001,231 A | 12/1999 | Kopf-Sill | |
| 6,004,515 A | 12/1999 | Parce et al. | |
| 6,007,690 A | 12/1999 | Nelson et al. | |
| 6,011,252 A | 1/2000 | Jensen | |
| 6,012,902 A | 1/2000 | Parce | |
| 6,042,721 A | 3/2000 | Peters, Jr. et al. | |
| 6,046,056 A | 4/2000 | Parce et al. | |
| 6,235,471 B1 | 5/2001 | Knapp et al. | |
| 6,267,858 B1 | 7/2001 | Parce et al. | |
| 6,274,337 B1 | 8/2001 | Parce et al. | |
| 6,288,220 B1 | 9/2001 | Kambara et al. | |
| 6,306,590 B1 | 10/2001 | Mehta et al. | |
| 6,306,659 B1 | 10/2001 | Parce et al. | |
| 6,387,707 B1 * | 5/2002 | Seul et al. | 436/164 |
| 6,429,025 B1 | 8/2002 | Parce et al. | |
| 6,632,655 B1 | 10/2003 | Mehta et al. | |
| 7,226,562 B2 * | 6/2007 | Holl et al. | 422/68.1 |
| 2001/0035351 A1 | 11/2001 | Simpson et al. | |
| 2002/0153251 A1 * | 10/2002 | Sassi et al. | 204/455 |

FOREIGN PATENT DOCUMENTS

| | | | |
|---|---|---|---|
| JP | 11243997 A | | 9/1999 |
| WO | WO 94/13623 | * | 6/1994 |
| WO | 9604547 A | | 2/1996 |
| WO | 9702357 A | | 1/1997 |
| WO | 9800231 A | | 1/1998 |
| WO | 9800705 A | | 1/1998 |
| WO | 9800707 A | | 1/1998 |
| WO | 9802728 A | | 1/1998 |
| WO | 9805424 A | | 2/1998 |
| WO | 9822811 A | | 5/1998 |
| WO | 9845481 A | | 10/1998 |
| WO | 9845929 A | | 10/1998 |
| WO | 9846438 A | | 10/1998 |
| WO | 9849548 A | | 11/1998 |
| WO | 9855852 A | | 12/1998 |
| WO | 9856505 A | | 12/1998 |
| WO | 9856956 A | | 12/1998 |
| WO | 9900649 A | | 1/1999 |
| WO | 9910735 A | | 3/1999 |
| WO | 9912016 A | | 3/1999 |
| WO | 9916162 A | | 4/1999 |
| WO | 9919056 A | | 4/1999 |
| WO | 9919516 A | | 4/1999 |
| WO | 9929497 A | | 6/1999 |
| WO | 9931495 A | | 6/1999 |
| WO | 9934205 A | | 7/1999 |
| WO | 9943432 A | | 9/1999 |
| WO | 9944217 A | | 9/1999 |
| WO | 9956954 A | | 11/1999 |
| WO | 0009753 A | | 2/2000 |

OTHER PUBLICATIONS

Hultman et al (1989 Nucleic Acids Research 17: 4937-4946).*
Tyagi, S. "Taking a census of mRNA populations with microbeads", Nature. (Jun. 2000) 18:597-598.
Wang Solid Phase Synthesis of Protected Peptides via photolytic Cleavage of the a-Methylphenacyl Ester Anchoring Linkage J. Org. Chem. (1976) 41:3258.
Zalipsky et al. "Attachment of Drugs to Polyethylene Glycols" Eur. Polym. J., (1983) 19(12), 1177-1183.
Beskin et al. "On the mechanism of the modular primer effect" Nucleic Acids Research (1995) 23 (15):2881-2885.
Bousse et al. "Parallelism in integrated fluidic circuits," SPIE (1998) 3259:179-186.
Brenner, S. et al. "Gene expression analysis by massively parallel signature sequencing (MPSS) on microbead arrays". Nature Biotechnology (2000) 18:630-634.
Bruchez et al. "Semiconductor Nanocrystals as Fluorescent Biological Labels" Science (1998) 281:2013-2016.
Bult et al. "Complete Genome Sequence of the Methanogenic Archaeon, *Methanococcus jannaschii*" Science (1996) 273:1058-1073.
Chee et al "Accessing Genetic Information with High-Density DNA Arrays" Science (1996) 274:610-614.
Chou, Hou-Pu et al. "A microfabricated device for sizing and sorting DNA molecules", Proc. Natl. Acad. Sci (1999) 26:11-13.
Cohen, C.B. et al., "A Microchip-Based Enzyme Assay for Protein Kinase A," Anal. Chem. (1999) 273:89-97.
Coutlee et al. "Nonisoltopic Detection of RNA in an Enzyme Immunossay Using a Monoclonal Anitbody against DNA-RNA Hybrids" Analytical Biochemistry (1989) 181:153-162.
Dasgupta, P.K. et al., "Electroosmosis: A Reliable Fluid Propulsion System for Flow Injection Analysis," Anal. Chem. (1994) 66:1792-1798.
Drmanac et al. "Accurate sequencing by hybridization for DNA diagnostics and individual genomics." Nature Biotechnology (1998) 16:54-58.
Drmanac et al. "Sequencing of Megabase Plus DNA by Hybridization: Theory of the Method" Genomics (1989) 4:114-128.
Eckstein et al. "Phosphorothioates in molecular biology" Trendes in Biochem (1989) 14:97.
Effenhauser et al. "Glass Chips for High-Speed Capillary Electrophoresis Separations with Submicrometer Plate Heights" Anal. Chem (1993) 65:2637-2642.
Effenhauser et al. "High-Speed Separation of Antisense Oligonucleotides on a Micromachined Capillary Electrophoresis Device." Anal. Chem. (1994) 66:2949-2953.
Fan et al. Micromachining of Capillary Electrophoresis Injectors and Separators on Glass Chips and Evaluation of Flow at Capillary Intersection. Anal.Chem. (1994) 66:177-184.
Fleischmann et al. Science (1995) 269:496-512.
Fodor et al. "Light-Directed, Spatially Addressable Parallel Chemical Synthesis" Science (1991) 251:767-777.
Fodor "Genes, chips and the Human Genome" FASEB Journal (1997) 11:121-121.
Fodor "Massively Parallel Genomics" Science (1997) 277:393-395.
Fraser et al. "The Minimal Gene Complement of Mycoplasma genitalium" Science (1995) 270:397-403.
Gay et al. J. Chem. Soc. (1970) 8:1123.
Harris, J.M "Laboratory Synthesis of Polyethylene Glycol Derivatives" Rev. Macromol. Chem. Phys., (1985) C25 (3):325-373.
Harrison et al. Capillary Electrophoresis and Sample Injection Systems Integrated on a Planar Glass Chip Anal. Chem. (1992) 64:1926-1932.

(56) References Cited

OTHER PUBLICATIONS

Harrison et al. "Micromachining a Miniaturized Capillary Electrophoresis-Based Chemical Analysis System on a Chip." Science (1993) 261:895-897.

Harrison et al. "Towards Miniaturized Electrophoresis and Chemical System Analysis Systems on Silicon: An Alternative to Chemical Sensors." Sensors and Actuators (1993) 10:107-116.

Ishii et al. "Bead-Based Sandwich Hybridization Characteristics of Oligonucleotide-Alkaline Phosphatase Conjugates and Their Potential for Quantitating Target RNA Sequences" Bioconjugate Chem. American Chemical Society (1993) 4:34-41.

Jacobson et al. "Open Channel Electrochromatography on a Microchip" Anal. Chem. (1994) 66:2369-2373.

Jacobson et al. "Precolumn Reactions with Electrophoretic Analysis Integrated on Microchip" Anal. Chem. (1994) 66:4127-4132.

Jacobson et al. "Effects of Injection Schemes and Column Geometry on the Performance of Microchip Electrophoresis Devices" Anal. Chem. (1994) 66:1107-1113.

Jacobson et al. "High Speed Separations on a Microchip." Anal. Chem. (1994) 66:1114-1118.

Jacobson et al. "Microchip electrophoresis with sample stacking" Electrophoresis (1995) 16:481-486.

Jacobson, S.C. et al., "Fused Quartz Substrates for Microchip Electrophoresis," Anal. Chem. (1995) 67:2059-2063.

Kopf-Sill et al. "Complexity and performance of on-chip biochemical assays," SPIE (1997) 2978:172-179 Feb. 10-11.

Manz, A. et al., "Electroosmotic pumping and electrophoretic separations for miniaturized chemical analysis systems," J. Micromech. Microeng. (1994) 4:257-265.

Mathe, C. et al. "Phosphopeptide Prodrug Bearing an S-Acyl-2thoethyl Enzyme-Labile Phosphate Protection" J.Org. Chem. (1998) 63: 8547-8550 (1998).

Nie et al. "Quantum Dot Bioconjugates for Ultrasensitive Nonisotopic Detection" Science (1998) 281:2016-2018.

Nyren et al "Solid Phase DNA Minisequencing by an Enzymatic Luminometric Inorganic Pyrophosphate Detection Assay," Anal. Biochem. (1993) 208:171-175.

Porter et al. "Direct PCR sequencing with boronated nucleotides" Nucleic Acids Research (1997) 25 (8):1611-1617.

Raja et al. "DNA sequencing using differential extension with nucleotide subsets (DENS)" Nucleic Acids Research (1997) 25 (4):800-805.

Ramsey, J.M. et al., "Microfabricated chemical measurement systems," Nature Med. (1995) 1:1093-1096.

Rich et al. "Preparation of a New o-Nitrobenzyl Resin for Solid-Phase Synthesis of tert-Butyloxycarbonyl-Protected Peptide Acids" J. Am. Chem. Soc. (1975) 97:1575-1579.

Ronaghi, M. et al. "Real-Time DNA Sequencing Using Detection of Pyrophosphate Release" Anal. Biochem. (1996) 242:84-89.

Ronaghi, M. et al. "A Sequencing Method Based on Real Time Pyrophosphate" Science (1998) 281:363-364.

Sanger et al. "DNA Sequencing with chain-terminating inhibitors" Proc. Nat. Acad. Sci., USA (1977) 74:5463-5467.

Seiler, K. et al., "Planar Glass Chips for Capillary Electrophoresis: Repetitive Sample Injection, Quantitation, and Separation Efficiency," Anal. Chem. (1993) 65:1481-1488.

Seiler, K. et al., "Electroosmotic Pumping and Valveless Control of Fluid Flow Within a Manifold of Capillaries on a Glass Chip," Anal. Chem. (1994) 66:3485-3491.

Seiler, K. et al. "Micromachining a Miniaturized Capillary Electrophoresis-Based Chemical Analysis System on a Chip" Mit Gebiete Lebensm. Hyg. (1994) 85:59-68.

Sundberg, S. A., "High-throughput and ultra-high-throughput screening: solution—and cell-based approches," Current Opinions in Biotechnology 2000, 11:47-53.

Tomb et al. "The complete genome sequence of the gastric pathogen Helicobacter pylori" Nature (1997) 539-547.

\* cited by examiner

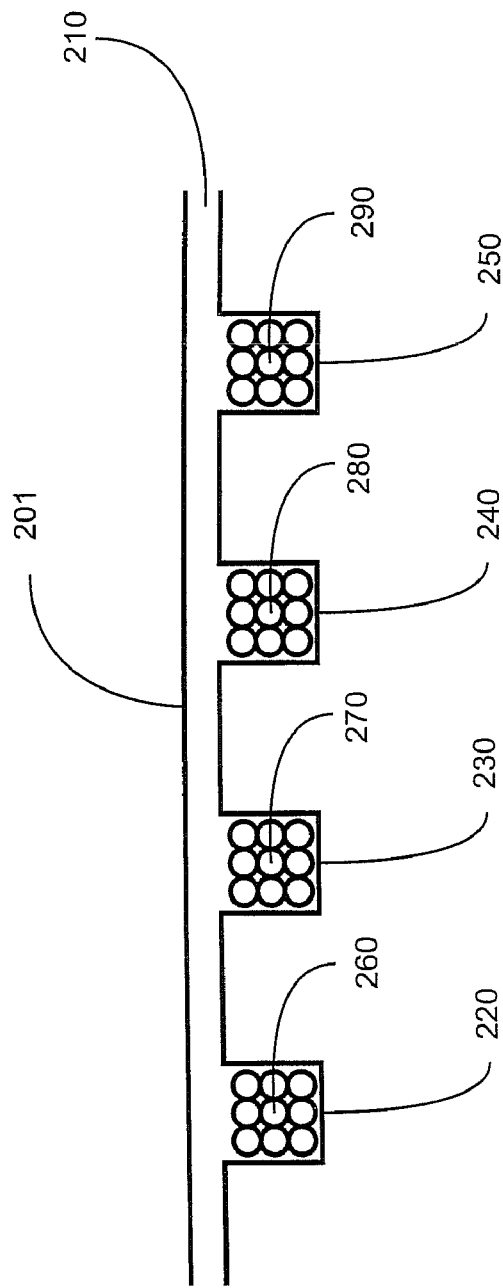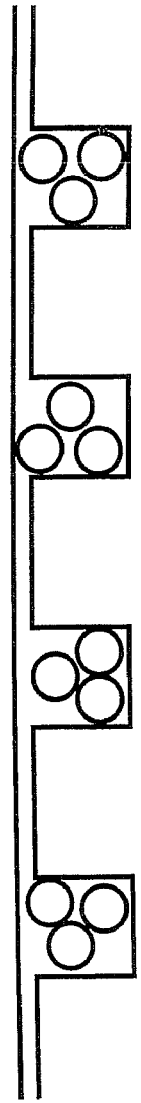

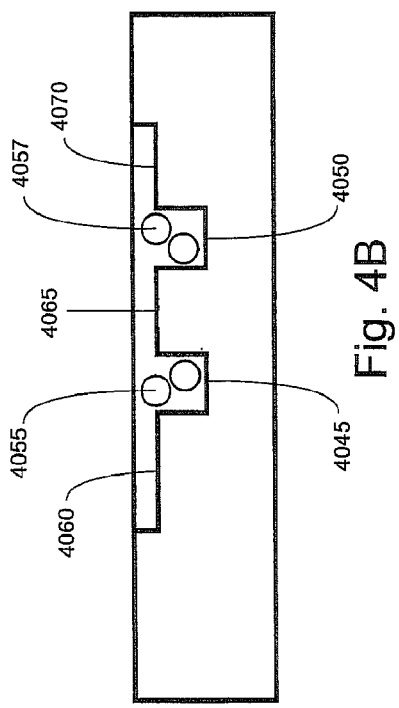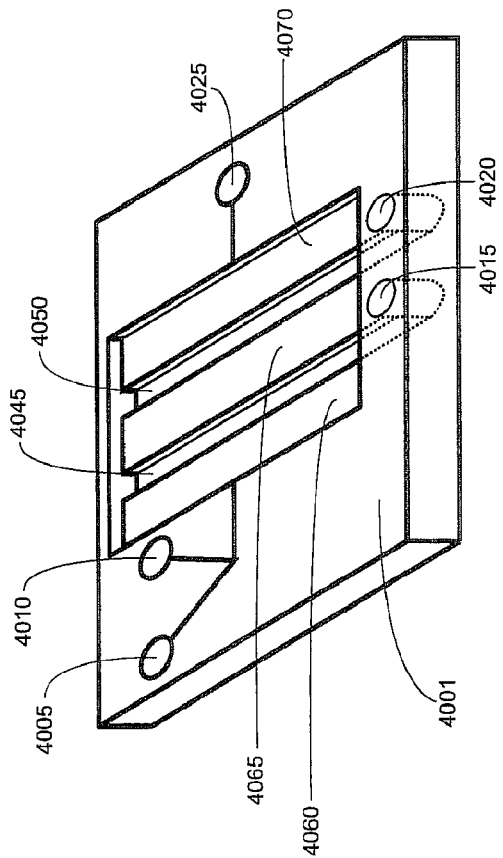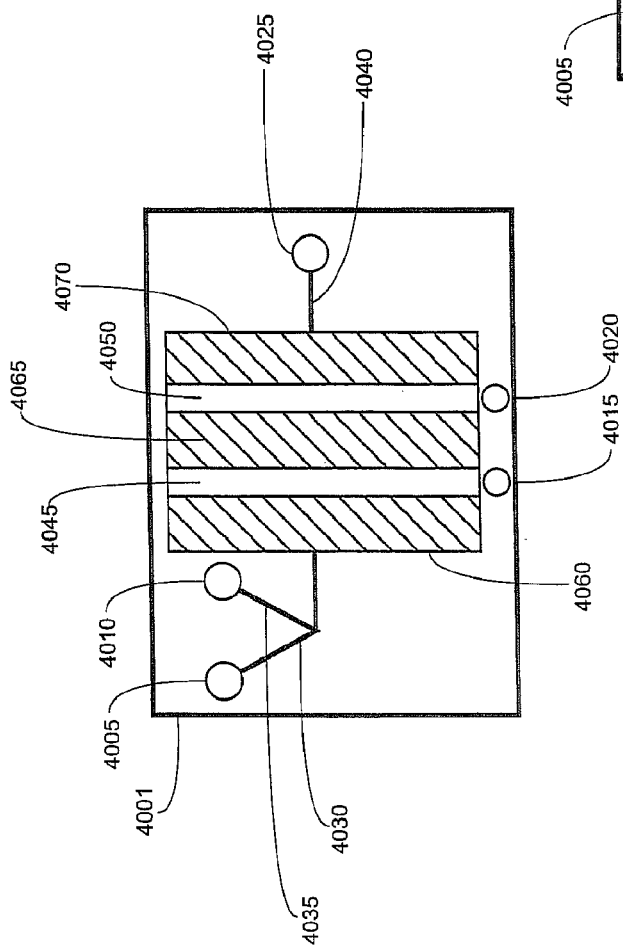
Fig. 4A
Fig. 4B
Fig. 4C

MANIPULATION OF MICROPARTICLES IN MICROFLUIDIC SYSTEMS

CROSS-REFERENCE TO RELATED APPLICATIONS

This application is a continuation of U.S. patent application Ser. No. 11/928,808 (now abandoned), filed Oct. 30, 2007, which is a divisional of U.S. patent application Ser. No. 10/606,201 (now abandoned), filed Jun. 25, 2003, which is a continuation of U.S. patent application Ser. No. 09/510,626, filed Feb. 22, 2000, now U.S. Pat. No. 6,632,655, which claims benefit of and priority to U.S. Ser. No. 60/121,223, filed Feb. 23, 1999 by Mehta et al.; U.S. Ser. No. 60/127,825, filed Apr. 5, 1999, by Mehta et al.; U.S. Ser. No. 60/128,643, filed Apr. 9, 1999, by Mehta et al.; co-filed PCT application PCT/US00/04522, filed Feb. 22, 2000; co-filed U.S. application U.S. Ser. No. 09/510,205 (now U.S. Pat. No. 6,613,513), filed Feb. 22, 2000; and co-filed PCT application PCT/US00/04486, filed Feb. 22, 2000. Each of these applications is incorporated herein by reference in its entirety for all purposes.

STATEMENT REGARDING FEDERALLY SPONSORED RESEARCH OR DEVELOPMENT

The present invention was made with government funding from the United States National Institute of Standards and Technology (NIST), through the Advanced Technology Program (ATP) under Grant No. 70NANB8H4000, and the United States government may have certain rights in the invention.

FIELD OF THE INVENTION

The invention is in the field of microfluidics and microarray technology. Apparatus, methods and integrated systems for detecting molecular interactions are provided. The apparatus include microscale arrays which are movable or fixed in a microfluidic system. The systems are capable of performing integrated manipulation and analysis in a variety of biological, biochemical and chemical experiments, including, e.g., DNA sequencing. Applications to chemical and biological systems, e.g., nucleic acid sequencing, enzyme kinetics, diagnostics, compound screening, and the like are provided.

BACKGROUND OF THE INVENTION

The development of microfluidic technologies by the inventors and their co-workers has provided a fundamental paradigm shift in how artificial biological and chemical processes are performed. In particular, the inventors and their co-workers have provided microfluidic systems which dramatically increase throughput for biological and chemical methods, as well as greatly reducing reagent costs for the methods. In these microfluidic systems, small volumes of fluid (e.g., on the order of a few nanoliters to a few microliters) are moved through microchannels (e.g., in glass or polymer microfluidic devices) by electrokinetic or pressure-based mechanisms. Fluids can be mixed, and the results of the mixing experiments determined by monitoring a detectable signal from products of the mixing experiments.

Complete integrated systems with fluid handling, signal detection, sample storage and sample accessing are available. For example, Parce et al. "High Throughput Screening Assay Systems in Microscale Fluidic Devices" WO 98/00231 and Knapp et al. "Closed Loop Biochemical Analyzers" (WO 98/45481; PCT/US98/06723) provide pioneering technology for the integration of microfluidics and sample selection and manipulation. For example, in WO 98/45481, microfluidic apparatus, methods and integrated systems are provided for performing a large number of iterative, successive, or parallel fluid manipulations. For example, integrated sequencing systems, apparatus and methods are provided for sequencing nucleic acids (as well as for many other fluidic operations, e.g., those benefiting from automation of iterative fluid manipulation). This ability to iteratively sequence a large nucleic acid (or a large number of nucleic acids) provides for increased rates of sequencing, as well as lower sequencing reagent costs. Applications to compound screening, enzyme kinetic determination, nucleic acid hybridization kinetics and many other processes are also described by Knapp et al.

As an alternative to microfluidic approaches, small scale array based technologies can also increase throughput of screening, sequencing, and other chemical and biological methods, providing robust chemistries for a variety of screening, sequencing and other applications. Fixed solid-phase arrays of nucleic acids, proteins, and other chemicals have been developed by a number of investigators. For example, U.S. Pat. No. 5,202,231, to Drmanac et al. and, e.g., in Drmanac et al. (1989) Genomics 4:114-128 describe sequencing by hybridization to arrays of oligonucleotides. Many other applications of array-based technologies are commercially available from e.g., Affymetrix, Inc. (Santa Clara, Calif.), Hyseq Technologies, Inc. (Sunnyvale, Calif.) and others. Example applications of array technologies are described e.g., in Fodor (1997) "Genes, Chips and the Human Genome" FASEB Journal. 11:121-121; Fodor (1997) "Massively Parallel Genomics" Science. 277:393-395; Chee et al. (1996) "Accessing Genetic Information with High-Density DNA Arrays" Science 274:610-614; and Drmanac et al. (1998) "Accurate sequencing by hybridization for DNA diagnostics and individual genomics." Nature Biotechnology 16: 54-58.

The present invention is a pioneering invention in the field of microfluidics and mobile array technologies, coupling the fluid handling capabilities of microfluidic systems with the robust chemistries available through array technologies (e.g., solid phase chemistries) to facilitate laboratory and industrial processes. Many applications and variations will be apparent upon complete review of this disclosure.

SUMMARY OF THE INVENTION

The present invention provides microfluidic arrays. The arrays include particle sets (or "packets") which can be mobile or fixed in position, e.g., within a microfluidic system. The particle sets can include fixed chemical components or can be modifiable. The arrays are used in a wide variety of assays, as chemical synthesis machines, as nucleic acid or polypeptide sequencing devices, as affinity purification devices, as calibration and marker devices, as molecular capture devices, as molecular switches and in a wide variety of other applications which will be apparent upon further review.

In one implementation, the invention provides microfluidic devices comprising one or more array(s) of particles. The device includes a body structure having a microscale cavity (e.g., microchannel, microchannel network, microwell, microreservoir or combination thereof) disposed within the body structure. Within the microscale cavity, an ordered array of a plurality of sets of particles (each particle set is constituted of similar or identical particle "members" or "types") constitute the array. The array is optionally mobile (e.g., flowable in a microfluidic system, with flow being in either the same or in a different direction relative to fluid flow) or can be fixed (e.g., having flowable reagents flowed across the system).

The arrays of the invention include a plurality of particle sets. The precise location of the particle sets within the arrays is not critical, and can take many configurations. In one simple embodiment, particle sets abut in channels. For example, 2, 3, 4, 5, 6, 7, 8, 9, 10, 100, 1,000, 10,000, 100,000 or more particle sets can abut in a single channel. Alternatively, non-abutting sets of particles dispersed within a microfluidic device can also be used, e.g., where the spatial location of each set of particles is known or can be determined. Fluidic reagents and particles are optionally flowed through the same or through different microchannels (or other microfluidic structures such as wells or chambers). For example, fluidic reagents are optionally flowed from a first channel into a second channel which includes particle sets of the array.

Particles (alternatively "microparticles") of the arrays of the invention can be essentially any discrete material which can be flowed through a microscale system. Example particles include beads and biological cells. For example, polymer beads, silica beads, ceramic beads, clay beads, glass beads, magnetic beads, metallic beads, inorganic beads, and organic beads can be used. The particles can have essentially any shape, e.g., spherical, helical, irregular, spheroid, rod-shaped, cone-shaped, disk shaped, cubic, polyhedral or a combination thereof. Particles are optionally coupled to reagents, affinity matrix materials, or the like, e.g., nucleic acid synthesis reagents, peptide synthesis reagents, polymer synthesis reagents, nucleic acids, nucleotides, nucleobases, nucleosides, peptides, amino acids, monomers, cells, biological samples, synthetic molecules, or combinations thereof. Particles optionally serve many purposes within the arrays, including acting as blank particles, dummy particles, calibration particles, sample particles, reagent particles, test particles, and molecular capture particles, e.g., to capture a sample at low concentration. Additionally the particles are used to provide particle retention elements. Particles are sized to pass through selected microchannel regions (or other microscale elements). Accordingly, particles will range in size, depending on the application, e.g., from about 0.1 to about 500 microns in at least one cross-sectional dimension.

In one aspect, the microfluidic system comprises an intersection of at least two microchannels. At least one member of the particle array is transported within a first of the at least two channels to a point proximal to or within the channel intersection. At least one of the reagents is transported through a second of the at least two intersecting microchannels to a point proximal to or within the channel intersection. The at least one member of the particle array and the at least one reagent are contacted proximal to or within the channel intersection.

Methods of sequencing nucleic acids are provided. In the methods, a first set of particles comprising at least one set of nucleic acid templates is provided, e.g., in a first microfluidic channel. A train of reagents (i.e., an ordered or semi-ordered arrangement of fluidic reagents in a channel) comprising a plurality of sequencing reagents is flowed across the first set of particles, or the first set of particles is flowed through the reagent train, depending on the application. This results in contacting the at least one set of nucleic acid templates with the plurality of sequencing reagents. Signals resulting from exposure of the first set of particles to the reagent train are selected, thereby providing a portion of sequence of the nucleic acid template. For example, the reagent train can include a polymerase, a sufurylase, an apyrase, an inorganic phosphate, ATP, a thermostable polymerase, luciferin, luciferase, an endonuclease, an exonuclease, $Mg^{++}$, a molecular crowding agent, a buffer, a dNTP, a dNTP analog, a fluorescent nucleotide, a chain terminating nucleotide, a reversible chain terminating nucleotide, a phosphatase, a reducing agent, an intercalator, a salt, DTT, BSA, a detergent (e.g., Triton® or Tween®), chemicals to inhibit or enhance EO flow (e.g., polyacrylamide), or other sequencing reagent. One preferred use for the arrays of the invention is sequencing by "synthesis" or "incorporation," e.g., pyrosequencing. For example, the reagent train or array optionally include reagents for sequencing nucleic acid templates by pyrosequencing. A variety of other sequencing approaches are described herein.

Steps in the methods herein can be performed repeatedly or reiteratively for chemistries such as sequencing that involve repetitive synthesis and/or analysis steps. As reagents are depleted e.g., in the reagent train noted above, the method further optionally includes flowing a second train of reagents comprising a plurality of sequencing reagents across the first set of particles, or flowing the first set of particles through the second reagent. Alternatively, reagents are flowed in excess for a period of time, after which the channel(s) are rinsed, e.g., with a buffer before flowing a second reagent.

To further avoid contamination between repetitions or steps, methods are provided for loading and unloading reagents from a microfluidic device using a pair of split reagent wells and a pair of split waste wells.

Integrated systems and methods for performing fluidic analysis of sample materials in a microfluidic system having a particle array are also provided. For example, an integrated microfluidic system is provided which has a microfluidic device with the particle array, a material transport system, and a fluidic interface in fluid communication with the particle array. The interface samples a plurality of materials from one or a plurality of sources of materials and introduces the materials into contact with the particle array.

In the integrated methods, a first material from the plurality of materials is sampled with the fluidic interface. The first material is introduced into contact with at least one member of the particle array, whereupon the first sample material and at least a first member of the particle array react. A reaction product of the first sample material and the particle array is then analyzed and a second material (which may be the same as or different than the first material) is selected, based upon the reaction product. The second material is contacted with the particle array, where the second material and at least a second member of the particle array react. A second reaction product of the second material and the particle array is analyzed, thereby providing a fluidic analysis of the first and second materials.

For example, in sequencing applications, the first material can include a first DNA sequencing template, a first sequencing primer, or a first sequencing reagent while the second material can include a second DNA template, a second sequencing primer, or a second sequencing reagent. The array, in this example, includes a first mixture of reagents having DNA sequencing reagents or DNA templates. The first reaction product includes products of a DNA sequencing reaction (e.g., primer extension, sequencing by incorporation, e.g., by the pyrosequencing reaction or the like). A second sequencing primer is selected for inclusion in the second mixture of reagents based upon the products of the DNA sequencing reaction. Optionally, a third material is selected based upon the results of the analysis of the second reaction product. The third material is optionally introduced into proximity with the array, whereupon the third material and the array react. As above, the third reaction product is analyzed. This process is optionally reiterated several times (e.g., easily 10 times or more, often 100-1,000 times or more). Indeed, the process can be repeated thousands of times in a single experiment, e.g., to sequence a long stretch of DNA, or the like. Ordinarily, the integrated system includes a computer for performing or assisting in selection of the second material. The integrated system can also include fluid handling elements, e.g., electrokinetic or pressure flow controllers.

Systems for optimizing or performing a desired chemical reaction are provided. The system includes a microfluidic device which includes a microscale cavity having a particle array disposed therein. The particle array includes a plurality of particle sets. The system includes an electrokinetic or pressure based fluid direction system for transporting a selected volume of a first reactant to the array, or for reconfiguring the position of the array or for reconfiguring the arrangement of array members, or for loading array members (e.g., constituting a plurality of array sets) into the microscale cavity. The system also includes a control system, e.g., including a computer, which instructs the fluid direction system to deliver a first selected volume of first reactant to the array, or for moving members of the array into proximity with the first reactant, where contacting or mixing of the first reactant and at least one member of the array produces a first chemical reaction product. The control system optionally directs a plurality of mixings of the first reactant and the array (e.g., by electrokinetic and/or pressure based manipulation of reagent or array member as described herein), wherein a reaction condition selected from: temperature, pH, and time is systematically varied in separate mixings reactions. The system typically includes a detection system for detecting the first chemical reaction product e.g., as set forth above and supra. Other optional elements include a temperature control element for controlling temperature of reaction of the first and second element, a source of acid, a source of base and a source of reactants, reagents, array members, or the like.

In one aspect, the system instructs the fluid direction system to contact a second selected volume of the first or a second reactant with the array. This contact produces a second chemical reaction product.

The particles of the arrays optionally include a tag and one or more of the particle modification reagents comprising an anti-tag ligand. A "tag" is a component that can be detected, directly or indirectly (e.g., by binding to a detectable element). Exemplar tag and anti-tag ligands include nucleic acids; nucleic acid binding molecules, amidin, biotin, avidin, streptavidin, antibodies, antibody ligands, carbohydrate molecules, carbohydrate molecule binding reagents, proteins, protein binding molecules, organic molecules, organic molecule binding reagents, receptors, receptor ligands, etc. The particle modification reagent can also include a functional domain, e.g., independently selected from those noted for the tag and tag ligand. For example, in one embodiment, the one or more particle modification reagent has a nucleic acid having a biotin or avidin attached thereto.

Wash buffers, heat application, or an electric pulse are optionally used to strip components from arrays, thereby changing the array members. New components can be added to the array members following such washing. For example one or more particle modification reagents can be removed from one or more of the particle sets following washing, to provide one or more stripped particle sets. At least one additional particle modification reagent can be flowed across the one or more stripped particle set, thereby producing an additional particle set.

Many additional aspects of the invention will be apparent upon review including uses of the devices and systems of the invention, methods of manufacture of the devices and systems of the invention, kits for practicing the methods of the invention and the like. For example, kits comprising any of the devices or systems set forth above, or elements thereof, in conjunction with packaging materials (e.g., containers, sealable plastic bags etc.) and instructions for using the devices, e.g., to practice the methods herein, are also contemplated. Methods of Manufacture and manufactured devices comprising arrays or array members are set forth in detail herein.

BRIEF DESCRIPTION OF THE FIGURES

FIG. 2, panels A and B provide side view schematics of a microchannel and particle retention region arrangement.

FIG. 4, panels A, B, and C provide top view and expanded view schematics of an example microfluidic system comprising array elements.

DEFINITIONS

Figure 1A:
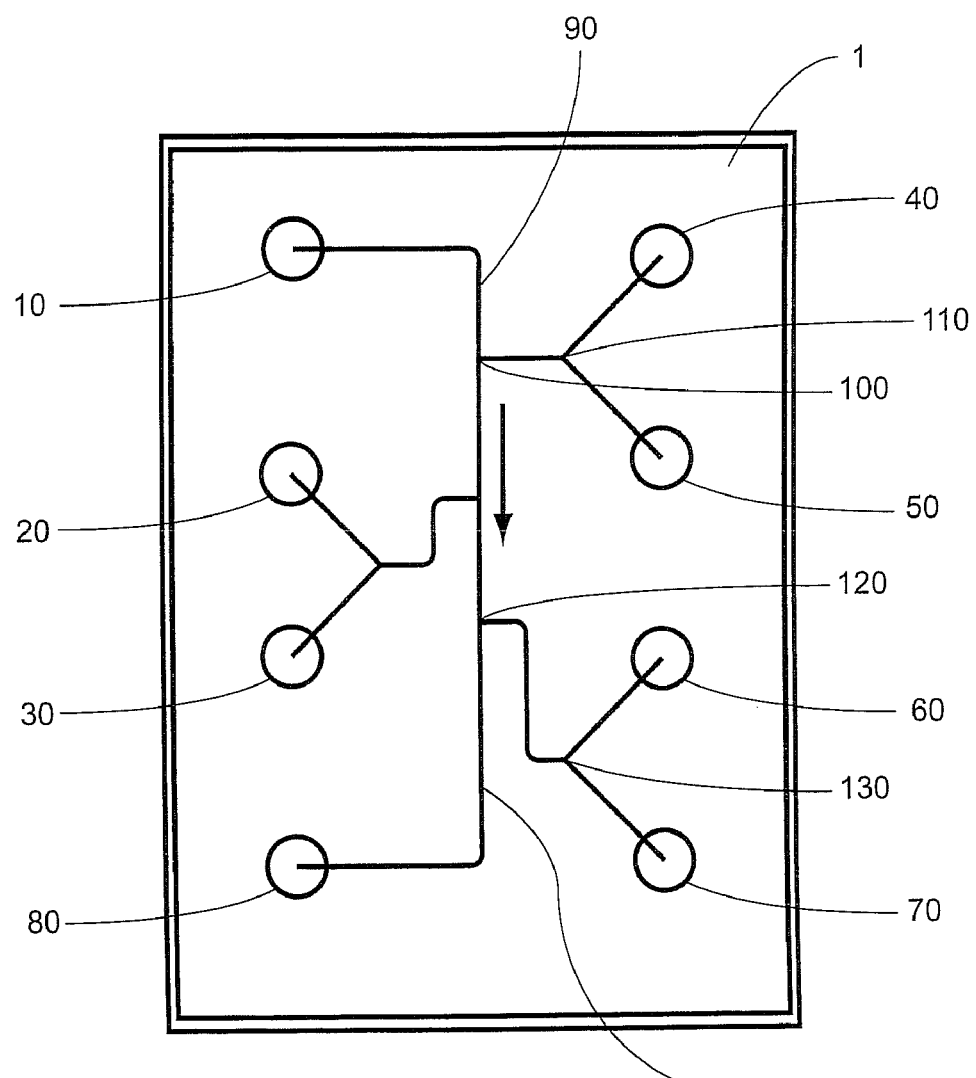
FIG. 1, panels A and B, is a schematic top view and expanded view of an example microfluidic system comprising array elements.

Unless indicated to the contrary, the following definitions supplement those in the art.

"Microfluidic," as used herein, refers to a system or device having fluidic conduits or chambers that are generally fabricated at the micron to submicron scale, e.g., typically having at least one cross-sectional dimension in the range of from about 0.1 µm to about 500 µm. The microfluidic system of the invention is fabricated from materials that are compatible with the conditions present in the particular experiment of interest. Such conditions include, but are not limited to, pH, temperature, ionic concentration, pressure, and application of electrical fields. The materials of the device are also chosen for their inertness to components of the experiment to be carried out in the device. Such materials include, but are not limited to, glass, quartz, silicon, and polymeric substrates, e.g., plastics, depending on the intended application.

A "microscale cavity" is a conduit or chamber having at least one dimension between about 0.1 and 500 microns.

A "microchannel" is a channel having at least one microscale dimension, as noted above. A microchannel optionally connects one or more additional structure for moving or containing fluidic or semi-fluidic (e.g., gel- or polymer solution-entrapped) components.

An "ordered array of a plurality of sets of particles" is an array of particle sets (each particle set is constituted of similar or identical particle "members" or "types") having a spatial arrangement. The spatial arrangement of particle sets can be selected or random. In a preferred embodiment, the spatial arrangement is selected. The arrangement can be known or unknown. In a preferred embodiment, the spatial arrangement of particle sets is known.

A "set" of particles is a group or "packet" of particles having similar or identical constituents.

A "particle movement region" is a region of a microscale element in which particles are moved. A "fluid movement region" is a region of a microscale element in which fluidic components are moved. As discussed supra, fluidic and particulate elements are moved by any of a variety of forces, including capillary, pressure, electrokinetic and the like.

A "particle retention region" is a region of a microscale element in which particles can be localized, e.g., by placing a physical barrier or porous matrix within or proximal to the retention region, by application of magnetic or electric fields, by application of pressure, or the like. For example, a porous matrix optionally comprises a fixed set of particles, e.g., particles about 100 µm to about 200 µm in cross-sectional dimension, within a microchannel.

A "microwell plate" is a substrate comprising a plurality of regions which retain one or more fluidic components.

A "pipettor channel" is a channel in which components can be moved from a source to a microscale element such as a second channel or reservoir. The source can be internal or external to a microfluidic device comprising the pipettor channel.

Two components are "physically associated" when they are in direct or indirect contact.

A particle array is "mobile" when a plurality of sets of the array can be moved in a selected or selectable manner, e.g., by electrokinetic, pressure-based or capillary fluid movement systems, or a combination of movement systems.

A "serial" stream of components, e.g., reagents is a train of reagents, is an ordered linear arrangement of the components.

A "parallel" set of components is an array of components which are in a plurality of linear arrangements, e.g., separate linear arrangements, of the components.

A "particle modification reagent" is a reagent that binds to or chemically alters one or more component that is physically associated with the particle.

DETAILED DESCRIPTION

The present invention provides microfluidic arrays. The array components can be mobile or fixed. They can also be of a selected type or type switchable, and can incorporate any of a wide variety of chemical or biochemical components. The arrays are broadly useful as tools for screening assay components, biopolymer sequencing, drug screening, assay normalization, as miniaturized chemical and biochemical synthesis machines, as molecular switches, as fluidic logic circuits and a variety of other applications that will become apparent upon complete review of this disclosure. The arrays can be components of integrated systems.

Methods of performing a plurality of chemical reactions in a microscale device are an aspect of the invention. In the methods, an array within a microfluidic system (e.g., having a body structure with a microscale interior cavity, etc. as described above) is provided. One or more liquid reagent is flowed into the interior cavity and into contact with particle sets of the array. The liquid reagent chemically reacts with one or more of the plurality of particles, thereby providing a chemical reaction in the microscale device.

Optionally, one or more of the plurality of sets of particles of the array (or the entire array or a substantial portion of) is moved into or through an intersection of at least two channels present in a microfluidic system. Mixing can occur in the intersections of channels, or within chambers, channels, wells, reservoirs, or the like. Thus, in the methods of the invention, at least one of the plurality of sets of particles can be moved through at least one of the at least two channels into an intersection of the at least two channels, while (separately or simultaneously) flowing the liquid reagent through a second of the at least two channels into the channel intersection, where the liquid reagent flows into contact with at least one set of particles of the array. In one aspect, the cavity comprises a main channel having a plurality of intersecting side channels, forming a plurality of channel intersections between the main channel and each of the intersecting side channels. The methods optionally include transporting at least one of the plurality of sets of particles in the main channel into at least two of the plurality of channel intersections.

Similarly, in one aspect, the method includes transporting at least one fluidic reagent through at least one of the side channels into at least one of the plurality of channel intersections, where the reagent flows into at least one of the plurality of sets of particles in the main channel. Alternatively, one or more of the particle sets of the array is flowed through a single microchannel and various reagents, e.g., liquid reagents, are optionally flowed through the particles or the particles are flowed through the reagent. The liquid reagent is optionally flowed through a capillary fluidly coupled to the single microchannel, e.g., a capillary that sips fluid from a microwell plate into a microfluidic device, e.g., a single channel or multichannel device.

Methods also optionally include moving particles (or reagents) into the interior cavity. For example, in one embodiment, the interior cavity has a broad channel with narrow channels within the broad channel. The narrow channels are deeper in at least one dimension than the broad channel. A plurality of sets of particles are transported into one or more of the narrow channels to form the array. Optionally, a liquid reagent is also (subsequently or previously) transported through the broad channel and the narrow channel and into contact with the plurality of sets of particles. For example, a liquid reagent is optionally sipped from a microtiter plate by a capillary fluidly coupled to a microfluidic device, in which device the liquid reagent contacts one or more particle set. Microparticles are also optionally brought into a microfluidic device through a sipper capillary attached to a microfluidic device. Exemplar liquid reagents include those described above such as nucleic acid sequencing reagents.

One preferred use for the arrays of the invention is nucleic acid or protein sequencing (or sequencing monomer elements of any polymer). For example the methods of the invention optionally include sequencing by hybridization, sequencing by synthesis or incorporation, sequencing by photobleaching, sequencing by intercalation, specific detection of nucleic acid polymorphisms, specific detection of a nucleic acid, diagnosing or predicting prognosis of a disease or infectious condition associated with presence or absence of a nucleic acid in a biological sample, diagnosing or predicting prognosis of a disease or infectious condition associated with presence or absence of a protein in a biological sample, serial or parallel hybridization between multiple liquid reagents and members of the array, and serial or parallel detection of results of multiple hybridization reactions between liquid reagents and members of the array.

Methods of contacting samples and reagents in a microfluidic system are also provided. In these methods, a plurality of members of a particle array which includes a plurality of samples is transported to a selected location within the microfluidic system. Simultaneously, separately or sequentially, the reagents are also transported within the microfluidic system such that members of the particle array and the reagents are contacted. Members of the particle array and the reagents are optionally repeatedly transported sequentially or simultaneously within the microfluidic system. In microfluidic systems having one or more emission detectors, the method optionally includes transporting the plurality of particle members past the one or more emission detectors, before, during, or after contacting the plurality of particle members with one or more of the reagents.

Array Configurations

As noted, the devices and systems of the invention typically include a body structure having a microscale cavity (e.g., microchannel, microchannel network, microwell, microreservoir or combination thereof) disposed within the body structure. Within the microscale cavity, an ordered array of a plurality of sets of particles constitute the array. The array is optionally mobile (e.g., flowable in a microfluidic system) or can be fixed (e.g., having flowable reagents flowed across the system). A fixed array of particles optionally comprises a porous barrier to capture or retain other solid phase components, e.g., another set of particles.

Mobile Arrays

The arrays of the invention are optionally mobile. Arrays comprise particle sets such as beads, microspheres, cells, fluidly transportable substrates, or the like. The particles are optionally moved by flowing fluids comprising the particles through or to a desired location, e.g., within a microfluidic system. Particles or reagents can be moved within microfluidic arrays by any of a variety of techniques, including fluidic pressure, atmospheric pressure, capillary force, gravity, electrokinesis, electric and magnetic fields, and centripetal or centrifugal force.

The inventors and their co-workers have provided a variety of microfluidic systems in which the arrays of the invention can be constructed. For example, Ramsey WO 96/04547 provides a variety of microfluidic systems. See also, Ramsey et al. (1995), Nature Med. 1(10):1093-1096; Kopf-Sill et al. (1997) "Complexity and performance of on-chip biochemical assays," SPIE 2978:172-179 February 10-11; Bousse et al. (1998) "Parallelism in integrated fluidic circuits," SPIE 3259: 179-186; Chow et al. U.S. Pat. No. 5,800,690; Kopf-Sill et al. U.S. Pat. No. 5,842,787; Parce et al., U.S. Pat. No. 5,779,868; Parce, U.S. Pat. No. 5,699,157; U.S. Pat. No. 5,852,495 (J. Wallace Parce) issued Dec. 22, 1998; U.S. Pat. No. 5,869,004 (J. Wallace Parce et al.) issued Feb. 9, 1999, U.S. Pat. No. 5,876,675 (Colin B. Kennedy) issued Mar. 2, 1999; U.S. Pat. No. 5,880,071 (J. Wallace Parce et al.) issued Mar. 9, 1999; U.S. Pat. No. 5,882,465 (Richard J. McReynolds) issued Mar. 16, 1999; U.S. Pat. No. 5,885,470 (J. Wallace Parce et al.) issued Mar. 23, 1999; U.S. Pat. No. 5,942,443 (J. Wallace Parce et al.) issued Aug. 24, 1999; U.S. Pat. No. 5,948,227 (Robert S. Dubrow) issued Sep. 7, 1999; U.S. Pat. No. 5,955,028 (Calvin Y. H. Chow) issued Sep. 21, 1999; U.S. Pat. No. 5,957,579 (Anne R. Kopf-Sill et al.) issued Sep. 28, 1999; U.S. Pat. No. 5,958,203 (J. Wallace Parce et al.) issued Sep. 28, 1999; U.S. Pat. No. 5,958,694 (Theo T. Nikiforov) issued Sep. 28, 1999; and U.S. Pat. No. 5,959,291 (Morten J. Jensen) issued Sep. 28, 1999; Parce et al. WO 98/00231; Parce et al. WO 98/00705; Chow et al. WO 98/00707; Parce et al. WO 98/02728; Chow WO 98/05424; Parce WO 98/22811; Knapp et al., WO 98/45481; Nikiforov et al. WO 98/45929; Parce et al. WO 98/46438; Dubrow et al., WO 98/49548; Manz, WO 98/55852; WO 98/56505; WO 98/56956; WO 99/00649; WO 99/10735; WO 99/12016; WO 99/16162; WO 99/19056; WO 99/19516; WO 99/29497; WO 99/31495; WO 99/34205; WO 99/43432; and WO 99/44217; U.S. Pat. No. 5,296,114; and e.g., EP 0 620 432 A1; Seiler et al. (1994) Mitt Gebiete Lebensm. Hyg. 85:59-68; Seiler et al. (1994) Anal. Chem. 66:3485-3491; Jacobson et al. (1994) "Effects of Injection Schemes and Column Geometry on the Performance of Microchip Electrophoresis Devices" Anal. Chem. 66: 66.1107-1113; Jacobsen et al. (1994) "Open Channel Electrochromatography on a Microchip" Anal. Chem. 66:2369-2373; Jacobsen et al. (1994) "Precolumn Reactions with Electrophoretic Analysis Integrated on Microchip" Anal. Chem. 66:4127-4132; Jacobsen et al. (1994) "Effects of Injection Schemes and Column Geometry on the Performance of Microchip Electrophoresis Devices." Anal. Chem. 66:1107-1113; Jacobsen et al. (1994) "High Speed Separations on a Microchip." Anal. Chem. 66:1114-1118; Jacobsen and Ramsey (1995) "Microchip electrophoresis with sample stacking" Electrophoresis 16:481-486; Jacobsen et al. (1995) "Fused Quartz Substrates for Microchip Electrophoresis" Anal. Chem. 67: 2059-2063; Harrison et al. (1992) "Capillary Electrophoresis and Sample Injection Systems Integrated on a Planar Glass Chip." Anal. Chem. 64:1926-1932; Harrison et al. (1993) "Micromachining a Miniaturized Capillary Electrophoresis-Based Chemical Analysis System on a Chip." Science 261: 895-897; Harrison and Glavania (1993) "Towards Miniaturized Electrophoresis and Chemical System Analysis Systems on Silicon: An Alternative to Chemical Sensors." Sensors and Actuators 10:107-116; Fan and Harrison (1994) "Micromachining of Capillary Electrophoresis Injectors and Separators on Glass Chips and Evaluation of Flow at Capillary Intersections. Anal. Chem. 66: 177-184; Effenhauser et al. (1993) "Glass Chips for High-Speed Capillary Electrophoresis Separations with Submicrometer Plate Heights" Anal. Chem. 65:2637-2642; Effenhauser et al. (1994) "High-Speed Separation of Antisense Oligonucleotides on a Micromachined Capillary Electrophoresis Device." Anal. Chem. 66:2949-2953; and Kovacs EP 0376611 A2.

In general, these microfluidic systems can be adapted for use in the present invention, i.e., by introducing arrays into the microfluidic systems, e.g., for the assays set forth herein. A variety of array component introduction approaches for introducing array elements into microfluidic systems are noted herein.

Movement of Particles within Microfluidic Systems

The microfluidic devices which include arrays also can include other features of microscale systems, such as fluid transport systems which direct particle movement within the array channel, incorporating any movement mechanism set forth herein (e.g., fluid pressure sources for modulating fluid pressure in the array channel, electrokinetic controllers for modulating voltage or current in the array channel, gravity flow modulators, magnetic control elements for modulating a magnetic field within the array channel, or combinations thereof). The microscale cavity can also include fluid manipulation elements such as a parallel stream fluidic converter, i.e., a converter which facilitates conversion of at least one serial stream of reagents into parallel streams of reagents for parallel delivery of reagents to a reaction site within the microscale cavity. For example, a capillary is optionally used to sip a sample or samples from a microtiter plate and to deliver it to one of a plurality of channels, e.g., parallel reaction or assay channels. In addition, particle sets are optionally loaded into one or more channels of a microfluidic device through one sipper fluidly coupled to each of the one or more channels and to a sample or particle source, such as a microwell plate. Indeed, one advantage of the present system is the ability to provide parallel streams of reagents to samples fixed on arrays. This is particularly advantageous, because the volumetric accuracy requirements for delivery of reagents is often less than the volumetric requirements for samples. A wide variety of integrated microfluidic systems comprising serial to parallel fluid manipulation are described in Bousse et al., "Parallelism in integrated fluidic circuits," SPIE 3259: 179-186 (1998) and in CLOSED LOOP BIOCHEMICAL ANALYZERS; WO 98/45481 and the references therein.

Electrokinetic Controllers

One method of achieving transport or movement of particles through microfluidic channels is by electrokinetic material transport. "Electrokinetic material transport systems," as used herein, includes systems that transport and direct materials within a microchannel and/or chamber containing structure, through the application of electrical fields to the materials, thereby causing material movement through and among the channel and/or chambers, i.e., cations will move toward a negative electrode, while anions will move toward a positive electrode. For example, movement of fluids toward or away from a cathode or anode can cause movement of particles suspended within the fluid (or even particles over which the fluid flows). Similarly, the particles can be charged, in which case they will move toward an oppositely charged electrode (indeed, in this case, it is possible to achieve fluid flow in one direction while achieving particle flow in the opposite direction). In this embodiment, the fluid can be immobile or flowing.

In general, electrokinetic material transport and direction systems include those systems that rely upon the electrophoretic mobility of charged species within the electric field applied to the structure. Such systems are more particularly referred to as electrophoretic material transport systems. For electrophoretic applications, the walls of interior channels of the electrokinetic transport system are optionally charged or uncharged. Typical electrokinetic transport systems are made of glass, charged polymers, and uncharged polymers. The interior channels are optionally coated with a material which alters the surface charge of the channel.

A variety of electrokinetic controllers are described, e.g., in Ramsey WO 96/04547, Parce et al. WO 98/46438 and Dubrow et al., WO 98/49548, as well as a variety of other references noted herein.

To provide appropriate electric fields, the system generally includes a voltage controller that is capable of applying selectable voltage levels, simultaneously, to each of the reservoirs, including the ground. Such a voltage controller is optionally implemented using multiple voltage dividers and multiple relays to obtain the selectable voltage levels. Alternatively, multiple independent voltage sources are used. The voltage controller is electrically connected to each of the reservoirs via an electrode positioned or fabricated within each of the plurality of reservoirs. In one embodiment, multiple electrodes are positioned to provide for switching of the electric field direction in a microchannel, thereby causing the analytes to travel a longer distance than the physical length of the microchannel. Use of electrokinetic transport to control material movement in interconnected channel structures was described, e.g., in WO 96/04547 to Ramsey. An exemplary controller is described in U.S. Pat. No. 5,800,690. Modulating voltages are concomitantly applied to the various reservoirs to affect a desired fluid flow characteristic, e.g., continuous or discontinuous (e.g., a regularly pulsed field causing the sample to oscillate direction of travel) flow of labeled components toward a waste reservoir. Particularly, modulation of the voltages applied at the various reservoirs can move and direct fluid flow through the interconnected channel structure of the device.

Other Particle and Fluid Movement Approaches

Other methods of transport are also available for situations in which electrokinetic methods are not desirable. For example, sample introduction and reaction are optionally carried out in a pressure-based system to avoid electrokinetic biasing during sample mixing and high throughput systems typically use pressure induced sample introduction. Pressure based flow is also desirable in systems in which electrokinetic transport is also used. For example, pressure based flow is optionally used for introducing and reacting reagents in a system in which the products are electrophoretically separated. In the present invention particle arrays are optionally loaded using electrokinetic fluid control and other reagents are flowed through the particle arrays under pressure.

Pressure is optionally applied to microscale elements, e.g., to a channel, region, or reservoir, to achieve fluid movement using any of a variety of techniques. Fluid flow and flow of materials suspended or solubilized within the fluid, including cells or particle sets, is optionally regulated by pressure based mechanisms such as those based upon fluid displacement, e.g., using a piston, pressure diaphragm, vacuum pump, probe or the like to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, i.e., a plunger fitted into a material reservoir, for forcing material through a channel or other conduit, or is a combination of such forces.

In some embodiments, a vacuum source is applied to a reservoir or well at one end of a channel to draw a fluidic material through the channel. For example, a vacuum source is optionally placed at a reservoir in the present devices for drawing fluid into or through a channel, e.g., through a porous particle retention element, e.g., a particle set. Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

Hydrostatic, wicking and capillary forces are also optionally used to provide fluid pressure for continuous fluid flow of materials such as enzymes, substrates, modulators, or protein mixtures. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al. in U.S. Pat. No. 6,416,642. In these methods, an adsorbent material or branched capillary structure is placed in fluidic contact with a region where pressure is applied, thereby causing fluid to move towards the adsorbent material or branched capillary structure. The capillary forces are optionally used in conjunction with the electrokinetic or pressure-based flow in the present invention. The capillary action pulls material through a channel. For example a wick is optionally added to draw fluid through a porous matrix fixed in a microscale channel or capillary.

Mechanisms for reducing adsorption of materials during fluid-based flow are described in "PREVENTION OF SURFACE ADSORPTION IN MICROCHANNELS BY APPLICATION OF ELECTRIC CURRENT DURING PRESSURE-INDUCED FLOW" filed May 11, 1999 by Parce et al., application Ser. No. 09/310,027 (now U.S. Pat. No. 6,458, 259). In brief, adsorption of components, proteins, enzymes, markers and other materials to channel walls or other microscale components during pressure-based flow can be reduced by applying an electric field such as an alternating current to the material during flow. Alternatively, flow rate changes due to adsorption are detected and the flow rate is adjusted by a change in pressure or voltage.

Mechanisms for focusing labeling reagents, enzymes, modulators, and other components into the center of microscale flow paths, which is useful in increasing assay throughput by regularizing flow velocity, e.g., in pressure based flow, is described in "FOCUSING OF MICROPARTICLES IN MICROFLUIDIC SYSTEMS" by H. Garrett Wada et al., filed May 17, 1999, application 60/134,472. In brief, sample materials are focused into the center of a channel by forcing fluid flow from opposing side channels into the main channel comprising the cells, or by other fluid manipulation.

In an alternate embodiment, microfluidic systems can be incorporated into centrifuge rotor devices, which are spun in a centrifuge. Fluids and particles travel through the device due to gravitational and centripetal/centrifugal pressure forces.

Fluid flow or particle flow in the present devices and methods is optionally achieved using any one of the above techniques, alone or in combination.

Particle Retention Regions and Other Specific Configurations

As noted, the particle sets of the arrays of the invention can be fixed in place, or mobile. For example, the microscale cavity can have a first microchannel which includes a particle movement region and a particle retention region. The particle retention region typically includes at least one set of the plurality of sets of particles disposed within the particle retention region, although it can include more than one set. The particle "retention" area or region optionally includes a region of increased or decreased microchannel depth or width or other physical barrier (groove, mesh, net, matrix, etc.), an electromagnetic field, a porous matrix (e.g., sieving matrices are optional components of microfluidic systems, as described below), or other means of inhibiting particle movement in or adjacent to the region.

For example, in embodiments where the microfluidic cavity comprising the array has a first microchannel, the microchannel is optionally configured to include at least one reagent flow region and at least one particle capture region. The at least one particle capture region optionally has an increased or decreased depth or width relative to the at least one reagent flow region, or is bounded by a region of increased or decreased depth or width. For example, in one embodiment, the devices include regions of width (or depth) sufficient to permit passage of particles, where the particle capture region is insufficient in dimension to permit free passage of the particles. For example, where particles larger than 3-4 microns are used, a channel region having a cross sectional dimension smaller than 3-4 microns blocks flow of the particles, while still permitting flow of fluids. Preferred particle size ranges from about 0.1 microns to about 50 microns; accordingly, in this embodiment, a physical barrier which does not permit passage of a selected particle within this range of particle sizes can be used as a particle capture element. In one aspect, a "particle capture region" is bounded on at least one side by such particle capture elements. In another example, the reagent flow region comprises a cross-sectional dimension comprising passage of selected particles and the particle retention or capture region abuts a narrow channel region comprising a dimension sufficiently small to inhibit movement of a selected particle through the narrow channel. Such narrow channel regions are typically less than about 10 µm, more typically less than 5 µm. Preferable narrow channel dimensions are about 5 µm or smaller or about 3 µm or smaller.

In other embodiments, the particle capture region, e.g., in a capillary or microchannel, comprises a device to capture a set of particles, e.g., chemically coated microspheres or other chemically coated solid phase objects, e.g., for a sequential chemistry assay. The device typically comprises a physical barrier, e.g., a porous barrier with a defined pore size, that captures solid phase objects having a larger mean diameter than the pore size. The upstream end of the capillary or microchannel is typically inserted in a reagent, e.g., a liquid reagent, and the downstream end is typically coupled to a vacuum source or electrokinetic controller which transports the reagents across the bed of the captured solid phase. The first reagent brought into the channel is typically the solid phase in a suitable buffer and subsequent reagents follow sequentially, e.g., sequencing regents. For example, DNA coated microspheres are optionally captured in a particle retention area for sequencing by synthesis, wherein subsequent reagents comprise dNTPs brought in one at a time, e.g., with sufficient rinsing between nucleotides. Other applications include DNA probes and the like. The captured solid phase is typically captured in the particle retention area, e.g., by a physical barrier. Such barriers are optionally formed by a fixed particle set, by a sintered glass frit, e.g., a preformed frit that has been inserted into the channel or a frit that has been fabricated integral to the capillary or channel. Alternative barriers, include a frit, e.g., a fixed set of particles, formed from epoxy coated microspheres, e.g., providing an appropriate pore size. The fixed set of particles, e.g., epoxy coated microspheres, form a porous barrier which captures other particle sets or packets. For example, a set of particles is optionally flowed through a capillary, e.g., with glue or epoxy. The capillary is centrifuged to flow the glue or epoxy resin over the particles. Excess glue is then removed, leaving a fixed particle matrix which is optionally used to capture or retain flowing or mobile beads, e.g., chemically coated beads.

Other materials used to form the barrier include, but are not limited to, glass, plastic, and other materials comprising an appropriate pore size. The barrier or frit is optionally contained in a housing, which housing is optionally a capillary or a machined or molded plastic or glass unit.

The flow region can be in the same plane or transverse to the particle capture region. In typical embodiments, the microfluidic device comprising the microscale cavity includes a plurality of microchannels, which are optionally intersecting or non intersecting and which optionally fluidly connect with reservoirs, wells or the like. The microfluidic device can include, or be coupled to (e.g., through a channel, microchannel, sipper capillary, pipettor, pressure pipettor, electropipettor, etc.), external sources of reagents or particles, permitting loading of the particles, or reagents which interact with the particles. Thus, in one embodiment, the device comprises a loading channel region (or particle loading channel region) coupled to a source of at least a first selected particle type or reagent coupled to the microscale cavity. For example, the source of particle type or reagent can be a microwell plate external to the body structure having at least one well with the selected particle type or reagent, a well disposed on the surface of the body structure comprising the selected particle type or reagent, a reservoir disposed within the body structure comprising the selected particle type or reagent; a container external to the body structure comprising at least one compartment comprising the selected particle type or reagent, or a solid phase structure comprising the selected particle type or reagent.

The particle loading channel region is optionally fluidly coupled to one or more of: a pipettor channel with a port external to the body structure, an electropipettor channel with a port external to the body structure, a sipper capillary, e.g., external to the body structure, fluidly coupled to one or more microwell plates, a pipettor channel with a port internal to the body structure, an internal channel within the body structure fluidly coupled to a well on the surface of the body structure, an internal channel within the body structure fluidly coupled to a well within the body structure, or the like.

The ordered array optionally includes a plurality of sample sets associated with the plurality of particle sets, where each sample set is physically associated with one or more of the plurality of particle sets. In addition, the ordered array optionally includes a plurality of reagent sets associated with the plurality of particle sets, where each reagent set is physically associated with one or more of the plurality of particle sets. These reagent and particle sets are optionally associated with each other, typically such that each reagent set and each particle set is physically associated with one or more of the plurality of particle sets. Manufacturing methods for making the arrays, microfluidic devices, integrated systems and the like are also provided.

In addition to the aspects set forth above, in one specific set of methods, a plurality of particle sets is flowed through a first microscale channel having a particle flow region having a height to width aspect ratio greater than 1.

In another set of manufacturing embodiments, a first particle set is flowed through the particle flow region and the first particle set is fixed in a first location in the channel, resulting in a first fixed particle set, e.g., forming a particle retention area to capture or retain other sets of particles. A second particle set is flowed through the particle flow region to a region abutting the first fixed particle set, where the first fixed particle set blocks further flow of the second particle set in the direction of flow, resulting in a second fixed particle set. In some embodiments, a third particle set through the particle flow region to a region abutting the second fixed particle set, wherein the second fixed particle set blocks further flow of the third particle set in the direction of flow, resulting in a third fixed particle set. In some embodiments, the first particle set is fixed in a particle retention region, which inhibits movement of selected particles from the particle retention region e.g., by a physical barrier to movement of the particles that is proximal to or within the particle retention region, a magnetic field proximal to or within the particle retention region, a chemical particle capture moiety that is proximal to or within the particle retention region or the like.

In one aspect, the first particle set is fixed in a particle retention region, which abuts the particle flow region. The particle retention region has a decreased or increased height to width aspect ratio as compared to the particle flow region, which decreased or increased height to width aspect ratio, in combination with the dimensions of the particle flow region, creates a physical barrier at the point where the dimensions vary and inhibits movement of the first particle set from the particle retention region. Alterations in the aspect ratio can also be used to provide regions of faster or slower particle flow, depending on the shape of the particles. In another aspect, the particle retention area is formed by a set of particles, e.g., epoxy coated particles, which has been fixed in position in the channel, e.g., in a housing or by glue or epoxy. Alternatively, a sintered glass frit or other porous matrix is placed in the channel or fabricated within the channel to form a barrier.

In another set of manufacturing embodiments, methods of making a microfluidic particle array are provided. In the methods, a microfluidic device comprising a microscale cavity is provided. One or more particle sets are flowed into the microscale cavity. One or more particle modification reagents are flowed into contact with the one or more particle sets, thereby producing a plurality of particle sets comprising the microfluidic particle array.

Further understanding of specific configurations is developed by consideration of the following specific embodiments.

Figure 1B:
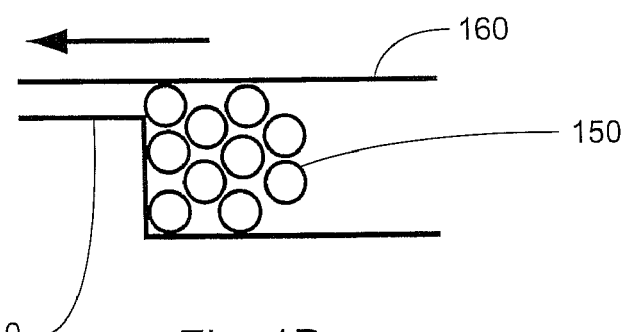

FIG. 1 provides microfluidic device 1 comprising reagent wells 10-30, additional wells 40-70 and waste well 80. The wells are fluidly connected to microchannel 90 comprising intersections 100 and 120. Additional wells 40-70 are fluidly coupled to intersections 100-130. Channel constriction 140 provides a bead capture area. As shown in detail, constriction 140 traps beads/particles 150 in particle retention region 160. In one example of this embodiment, the particles are between about 10 and about 4 microns, while particle retention region 160 is about 15 microns and constriction 140, e.g., a narrow channel region, is about 3 microns in diameter. Alternatively, the particles are larger than about 12 microns and particle retention region 160 is about 20 microns to about 50 microns and constriction 140 is about 3 microns to about 12 microns. For particles larger than about 15 microns, constriction region 140 is less than about 15 microns. Various particle sizes are used with various constriction measurements. Typically, the constriction is smaller than the particles of interest. An additional embodiment utilizing only one channel is provided in FIG. 14. Channel or capillary 1405 is optionally coupled to a sipper capillary that draws reagents, e.g., from a microwell plate, and through the capillary, e.g., through a pressure or electrokinetic controller.

FIG. 2, Panel A, provides microfluidic device 201 comprising channel 210. In a region (e.g., a bottom region) of channel 210 several particle retention regions 220-250 retain particle sets 260-290. In this simple embodiment, particle sets 260-290 constitute an array, or a portion of an array. Particle sets 260-290 optionally comprise particle members which are of smaller dimension than channel 210. In this configuration, particle sets 260-290 are optionally magnetic and held in place by application of an appropriate magnetic field. In other embodiments, channel 210 is of sufficiently narrow dimension that members of particle sets 260-290 cannot exit retention regions 220-250. This embodiment is depicted in FIG. 2B. Effective channel dimensions can be altered during operation by addition of a matrix or size-exclusion gel to the channel.

Figure 3B:
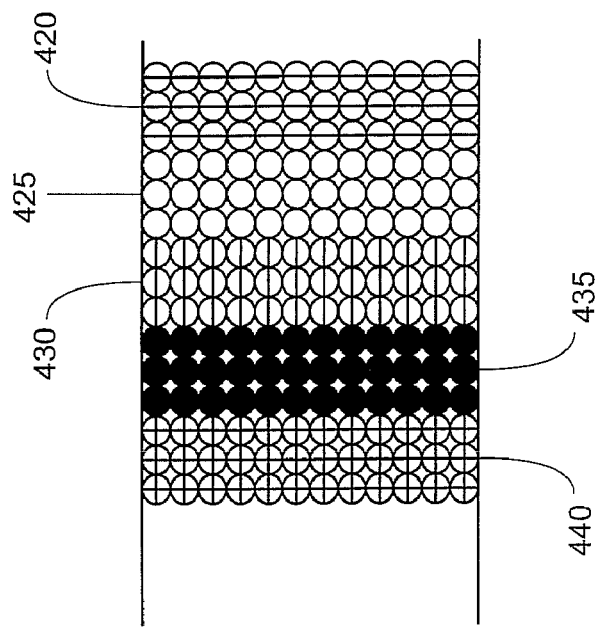
FIG. 3, panels A and B, is a top view and expanded view schematic of an example microfluidic system comprising array elements.
Figure 3A:
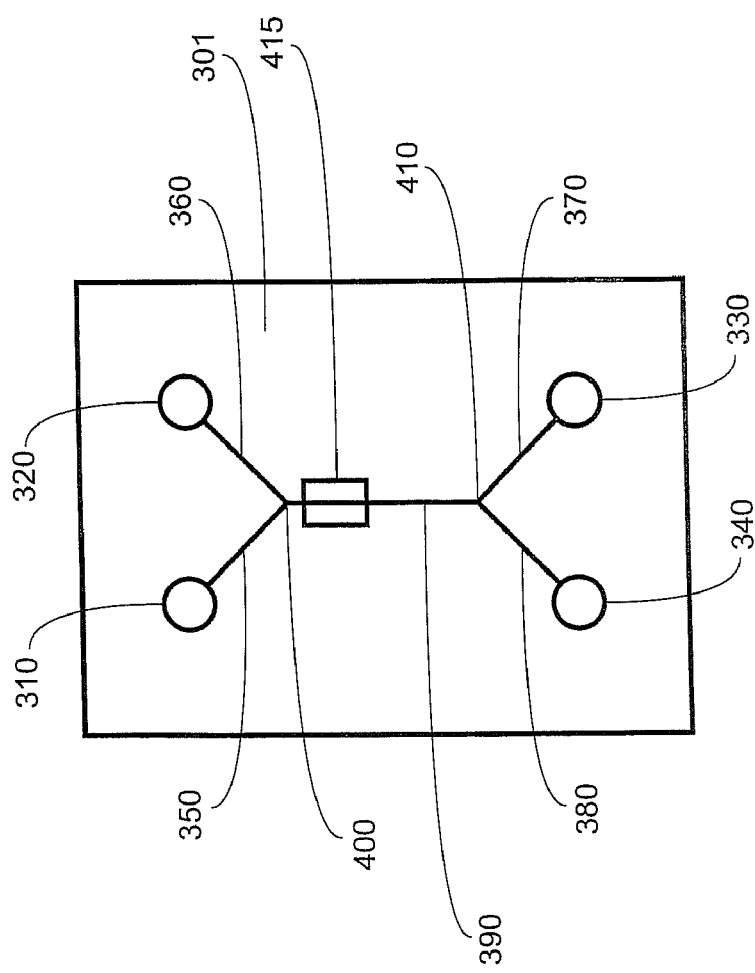

FIG. 3, panels A and B provide an additional aspect of the invention. The channels and particles used are typically smaller than the ones shown. An expanded view is used for ease of illustration. Microfluidic device 301 comprises wells 310-340. The wells are fluidly connected through a network of channels comprising channels 350-390 and intersections 400-410. Channel region 415 comprises particle sets 420-440. These particle sets can be immobile or mobile. For example, the particles are optionally held in place by a particle retention element, e.g., a porous barrier. Particle sets 420-440 are optionally the same size and/or shape or different sizes and/or shapes. In addition, each particle set optionally comprises a different number of particles.

FIG. 4, panels A, B and C show an additional embodiment (the channel dimensions are shown larger than typical channel dimensions for ease of illustration). Microfluidic device 4001 comprises wells 4005-4025. The wells are fluidly connected through channels 4030-4040 and through double-depth channels 4045-4050 and single depth wide channel regions 4060-4070. Double-depth channel regions 4045-4050 act as particle retention regions by trapping particles sets 4055-4057. Reagents can be passed across the trapped particle sets by flowing the reagents through single-depth wide channel regions 4060-4070. In one aspect, packets of particles are aligned to form trains of particles in double depth channels 4045-4050.

Figure 5:
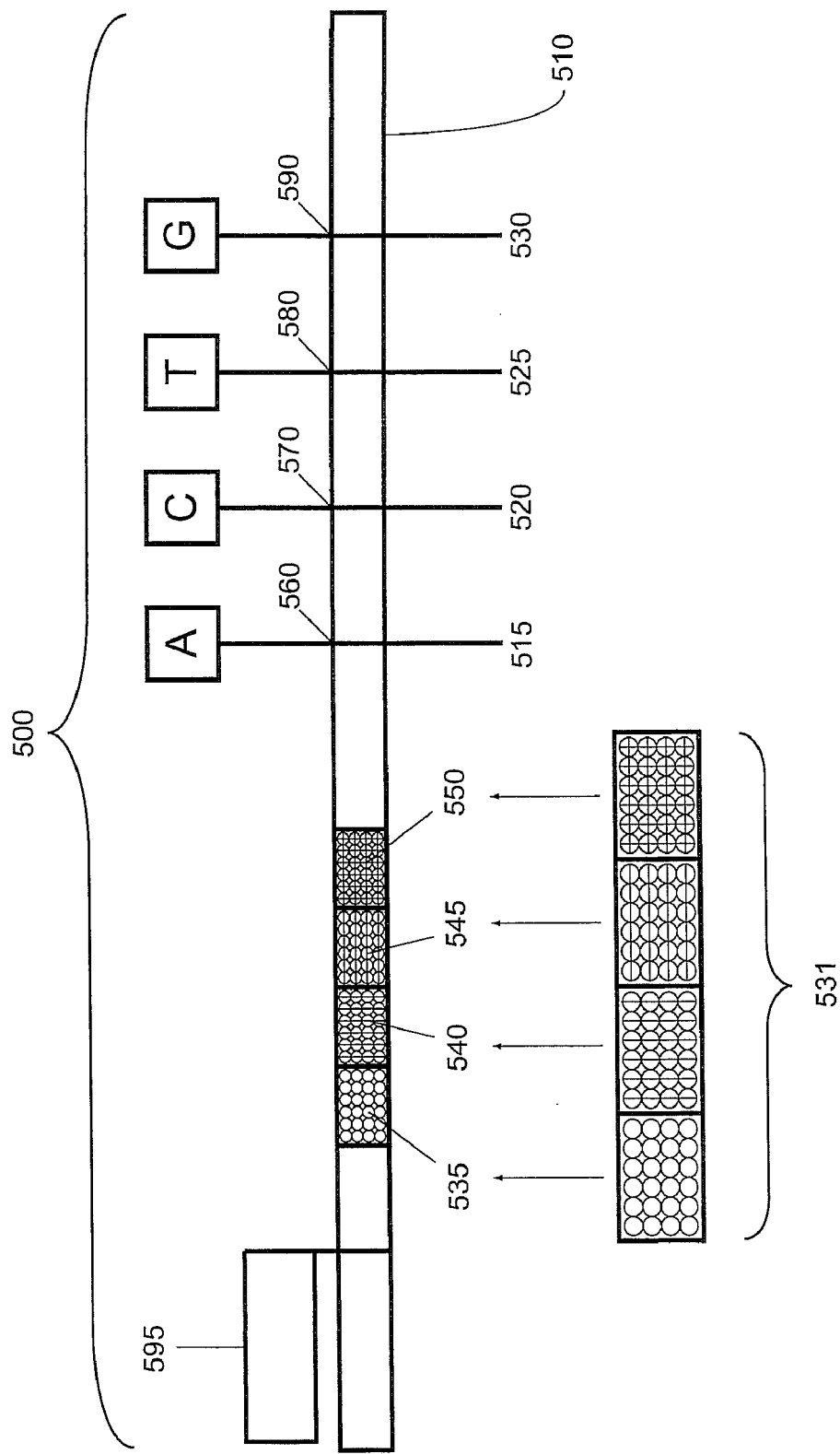
FIG. 5 is a side-view schematic of a main channel with reagent introduction channels for sequencing nucleic acids.

FIG. 5 shows an embodiment adapted to sequencing. Microfluidic device 500 comprises main channel 510 and reagent introduction channels 515-530 (as depicted, these are coupled to reagents for separate sequencing reactions, e.g., comprising A, G, C, or T nucleotides. Sample train 531 comprising a plurality of samples, e.g., particle sets 535-550, is passed back and forth through intersections 560-590. Reagent from channels 515-530 is flowed across each sample (or selected samples) in train 531 as the train passes the corresponding coupled intersection. Particle retention element 595 is an optional element.

Figure 14:
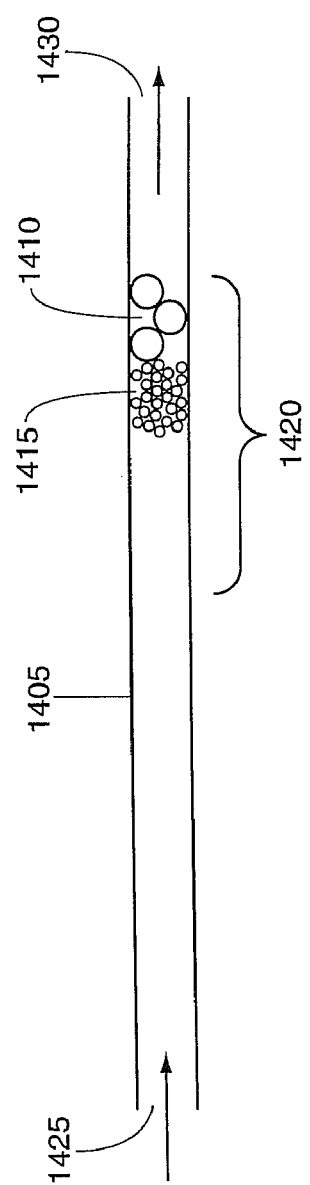
FIG. 14 is a side view of a capillary or microchannel containing a porous barrier formed from a plurality of particles which captures or retains a solid phase reaction element, e.g., another set of particles.

FIG. 14 shows an additional device embodiment adapted to sequencing. Capillary 1405 (which is optionally a channel in a microfluidic device) comprises particle retention element 1410 and particle set 1415. Particle retention element 1410 comprises a particle set that is fixed or immobilized in capillary 1405, thus creating particle retention region 1420 in capillary 1405. In a sequencing reaction, a set of particles, e.g., coated with a DNA template, is optionally flowed through capillary 1405 from inlet region 1425. For example, inlet region 1425 is optionally fluidly coupled to a sipper capillary, which during operation is fluidly coupled to a microwell plate. The set of DNA coated particles flows through capillary 1405 and is held or retained against particle retention element 1410, causing the set of DNA particles to become fixed in capillary 1405, such as particle set 1415. Sequencing reagents are then optionally flowed across particle set 1415 and optionally rinsed from the channel between introductions of different reagents. Particle retention element 1410 forms a porous barrier, which stops particle set 1415, thus allowing, e.g., a series of reagents to be flowed across the DNA template and then rinsed away if desired, e.g., four different nucleotides are serially flowed across the template coated particle set 1415 and unincorporated nucleotides are optionally rinsed away between steps. At the same time, the pore size of particle retention element 1410 has a pore size allowing, e.g., liquid reagents through so they are optionally rinsed out of capillary 1405, e.g., into a waste reservoir proximal to downstream region 1430.

Figure 15:
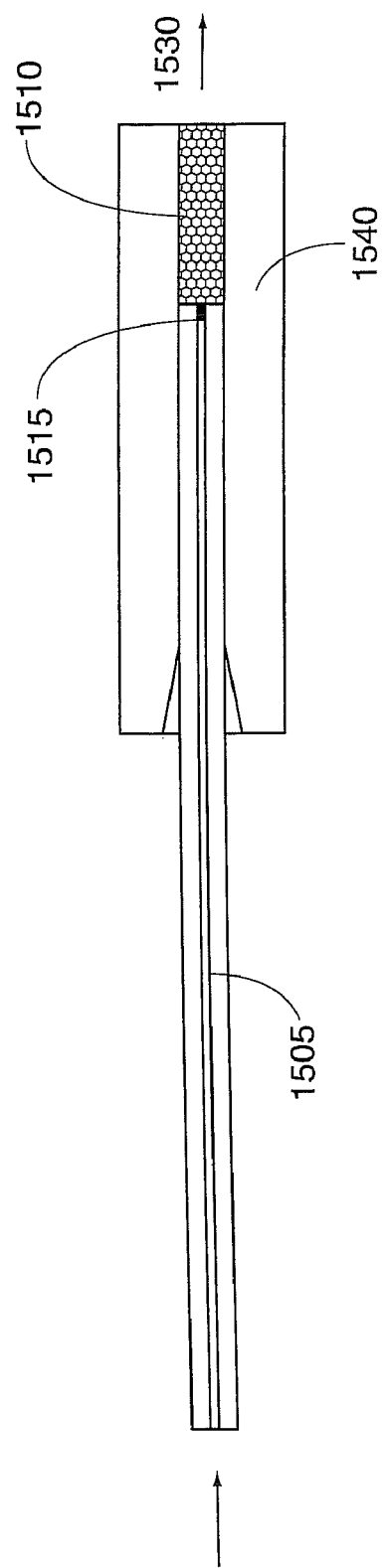
FIG. 15 is a side view of a capillary or microchannel in a housing, which housing comprises a porous barrier.

An alternate version of a particle retention element is shown in FIG. 15. Particle retention element 1510 is sealed within housing 1540. Particle sets and/or liquid reagents are flowed through capillary 1505. Particle sets with a mean diameter greater than the pore size of the particle retention element are stopped in capillary retention region 1515 by particle retention element 1510 and liquid reagents and particle sets with a smaller mean diameter than the pore size of particle retention area are flowed past particle retention area 1515, e.g., by a vacuum fluidly coupled to downstream capillary region 1530. In another embodiment, centrifugal force is used to draw reagents through capillary 1505.

Figure 16:
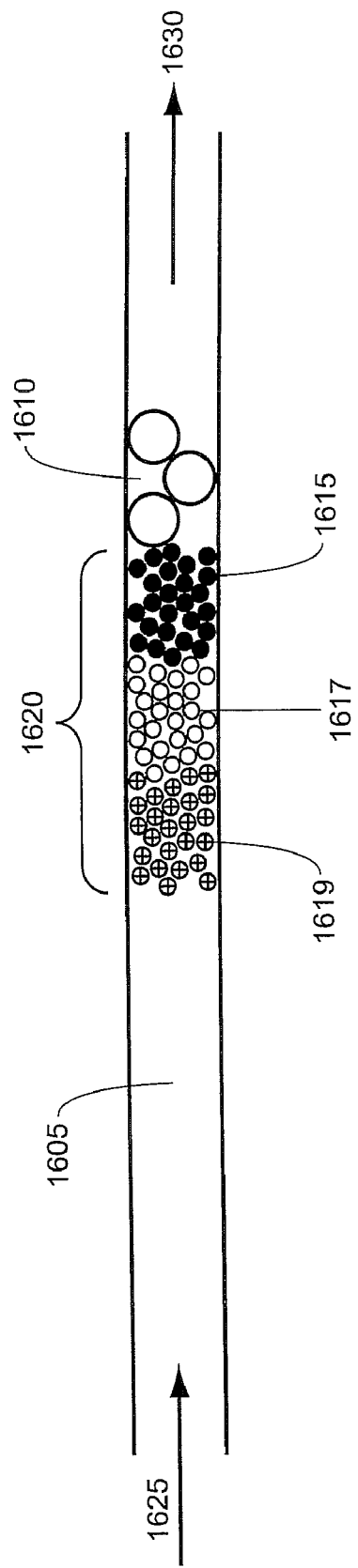
FIG. 16 is a side view of a capillary or microchannel comprising an integral or formed porous barrier made from a set of particles. The porous barrier is used, e.g., to capture multiple packets, i.e., sets of particles.

Alternatively, multiple solid phase components are flowed through and retained by a particle retention element. FIG. 16 shows particle retention element 1610 serving as a barrier to particle set 1615, which serves as a barrier to particle set 1617, which serves as a barrier to particle set 1619. Three particle sets are thus stacked in capillary 1605. Particle sets 1615, 1617, and 1619 optionally have the same mean diameter or different mean diameters. Particle retention element 1610 comprises a set of particles which when fixed within capillary 1605 forms a porous barrier to the movement of other particle sets. Liquid reagents are optionally flowed through capillary 1605 to contact particle sets 1615, 1617, and 1619. The liquid reagents are optionally introduced from a microwell plate via a sipper capillary fluidly coupled to upstream region 1625. The liquid reagents flow across and through particle sets 1615, 1617, and 1619 and react, e.g., with a DNA template and primer on the particles, and flow through particle retention element 1610, e.g., pulled by a vacuum fluidly coupled to downstream capillary region 1630.

Figure 6:
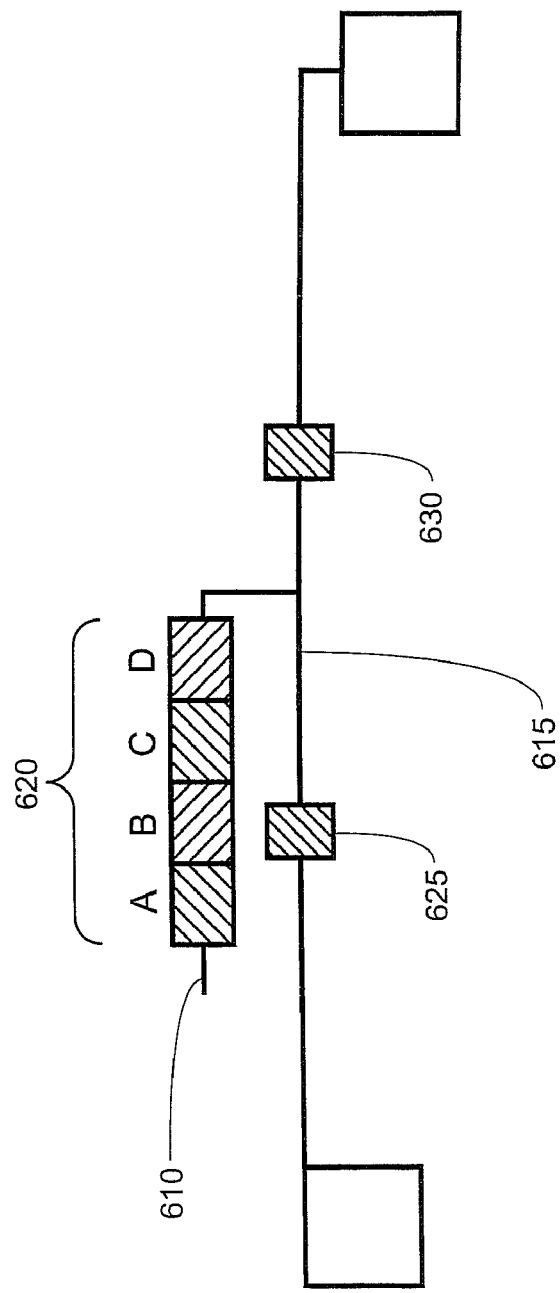
FIG. 6 is a schematic of a sipper for reagent/array train introduction into microfluidic devices.

FIG. 6 shows an embodiment adapted to high-throughput methods. In particular, a "sipper" (e.g., an electropipettor), e.g., sipper 610, draws one or more sets of beads or reagents ABCD and dispenses it into channel 615 or into multiple channels, e.g., parallel assay channels, where the sets are sent as packet 620 across target beads or reagent sites, e.g., regions 625 or 630. This is faster than sipping beads or reagents individually and passing them across the relevant reaction site.

Figure 7:
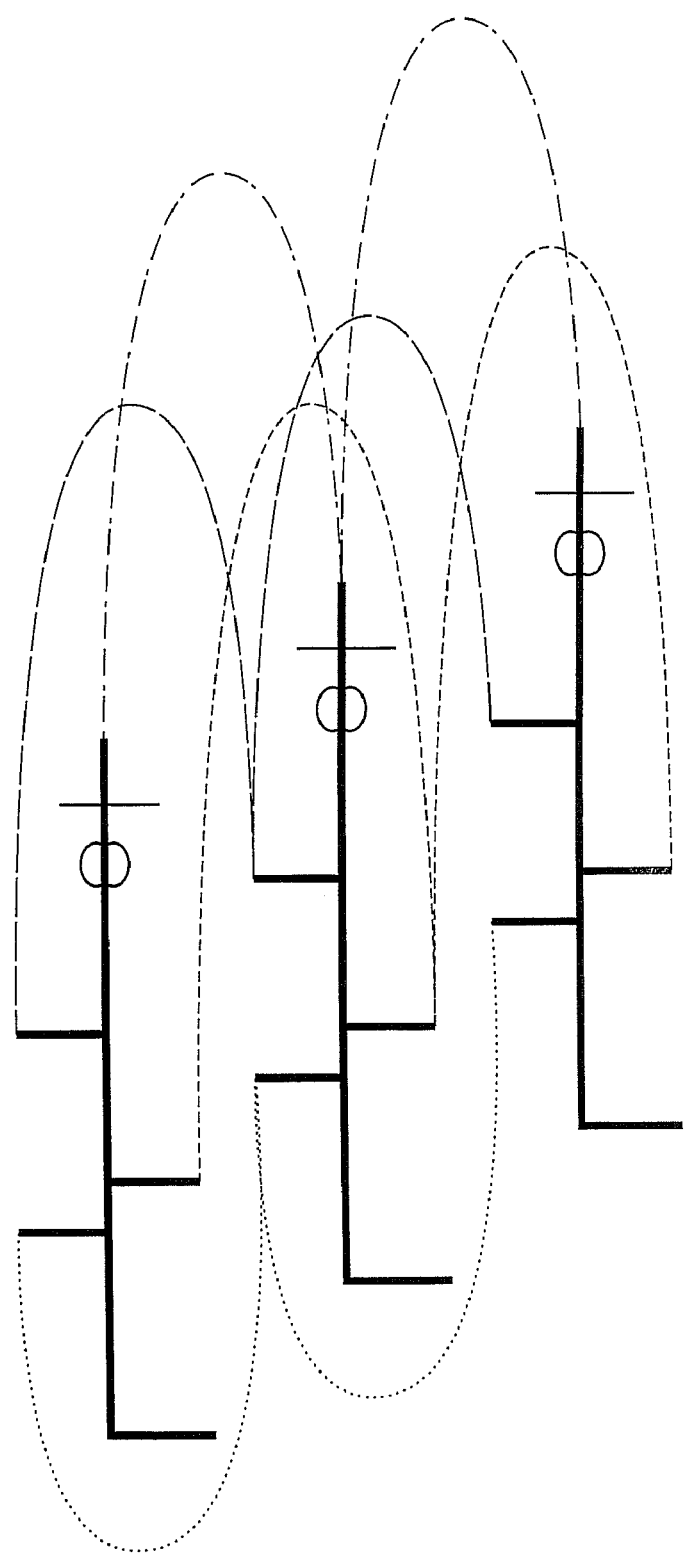
FIG. 7 is a schematic of a multiplexing arrangement useful for DNA sequencing.

FIG. 7 shows a multiplexing arrangement useful for DNA sequencing. The bold straight lines represent fluid channels connected to a sipper channel. The dotted lines represent electrical wires or pressure conduits connecting each of the reagent lines to a single controller. In this example, 3 sipper channels and 12 electrodes or pressure ports require only 4 controllers, instead of the more typical 12. An example of an assay using this arrangement is DNA sequencing, in which DNA samples are on beads, one per sipper channel. The side channels have different nucleotides that are passed over the beads sequentially. All of the bead samples will have the same reagent stream pass across them. For example, multiple DNA samples, e.g., three different DNA templates, are simultaneously sequenced using only four controllers, one for each reagent line and one for the main line. Alternatively, introduction of reagents from a sipper capillary fluidly coupled to a microwell plate and to each of the main reaction channels in FIG. 7 allows the DNA samples to be sequenced using only one controller coupled to each of the reaction channels.

Figure 8:
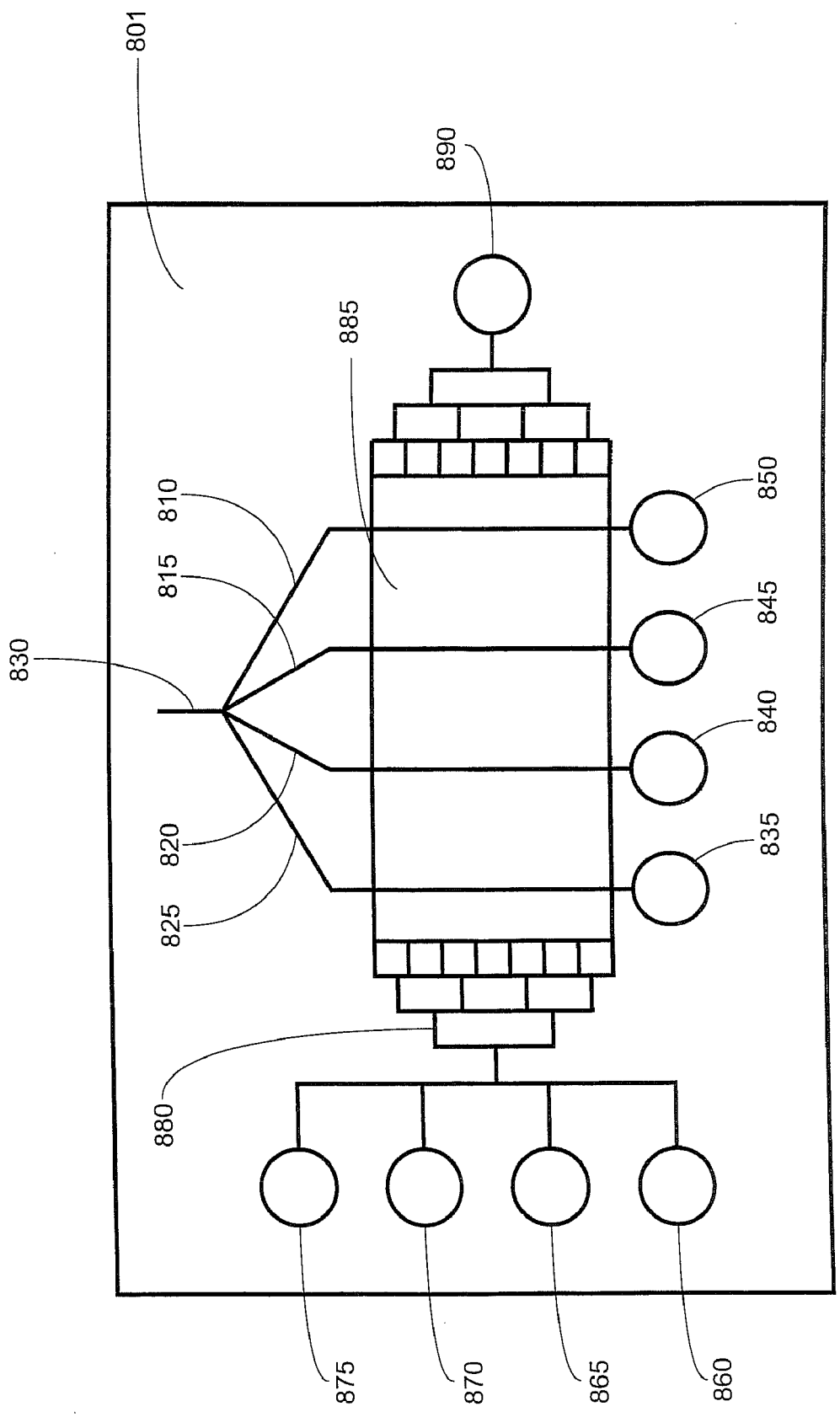
FIG. 8 is a schematic showing a device with pipettor access to a particle library.

FIG. 8 shows access to a particle library using one or more sippers. In particular, body 801 comprises particle channels 810-825 connected to sipper channel 830 which accesses a particle library (e.g., particle sets on a microwell plate). Packets of particles (e.g., comprising nucleic acid templates for sequencing) are directed (e.g., by electrokinesis or pressure-based mechanisms) into channels 810-825 to provide an array of particle sets. For example, an electrical potential or a vacuum is optionally applied at one or more of wells 835-850. Similarly, reagents (e.g., sequencing reagents) are flowed from any of wells 860-875 through fine channel network 880 and into broad channel 885, across the particle sets within channels 810-825, where the reagents interact with the particles in the channels. Alternatively, an individual channel is used in place of fine channel network 880. The particles are first flowed within fine channel network 880 to provide more even flow of reagents into broad channel 885. Waste reagents are flowed into waste well 890. Flow is provided by applying electrical or pressure potentials at one or more of wells 860-875 and 890. Although illustrated for clarity as a single sipper channel arrangement, multiple sipper channels interconnected to microfluidic structures can also be used, e.g., for simultaneous and/or parallel access to samples or fluidic reagents. Alternatively, a train of reagents is flowed from a microwell plate into sipper 830 and directly into each of channels 810-825.

Figure 9A:
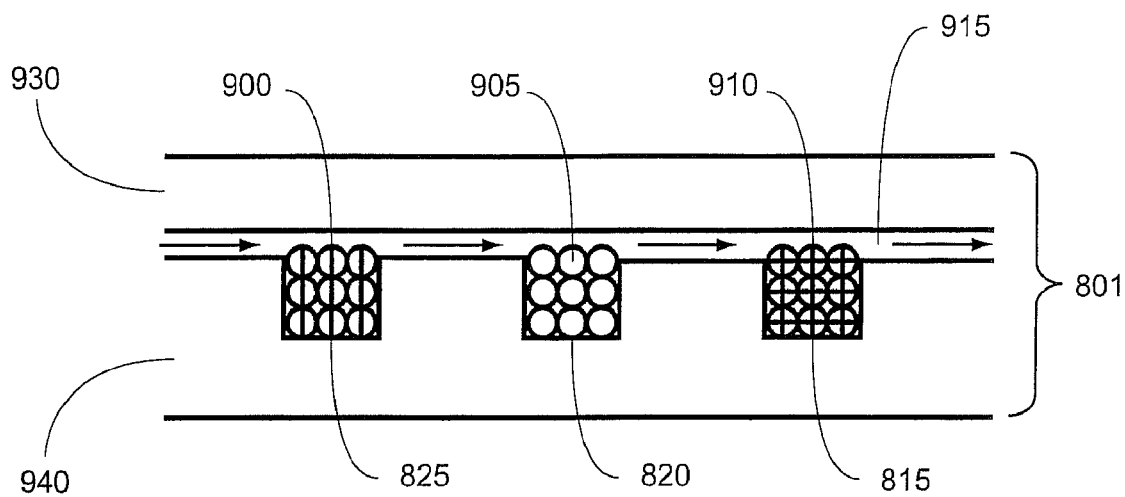
FIG. 9, panels A and B, provide a schematic of a device with particle packets in channels having reagent flow across the top of the particles. Panel A is a cross section. Panel B is a top view.
Figure 9B:
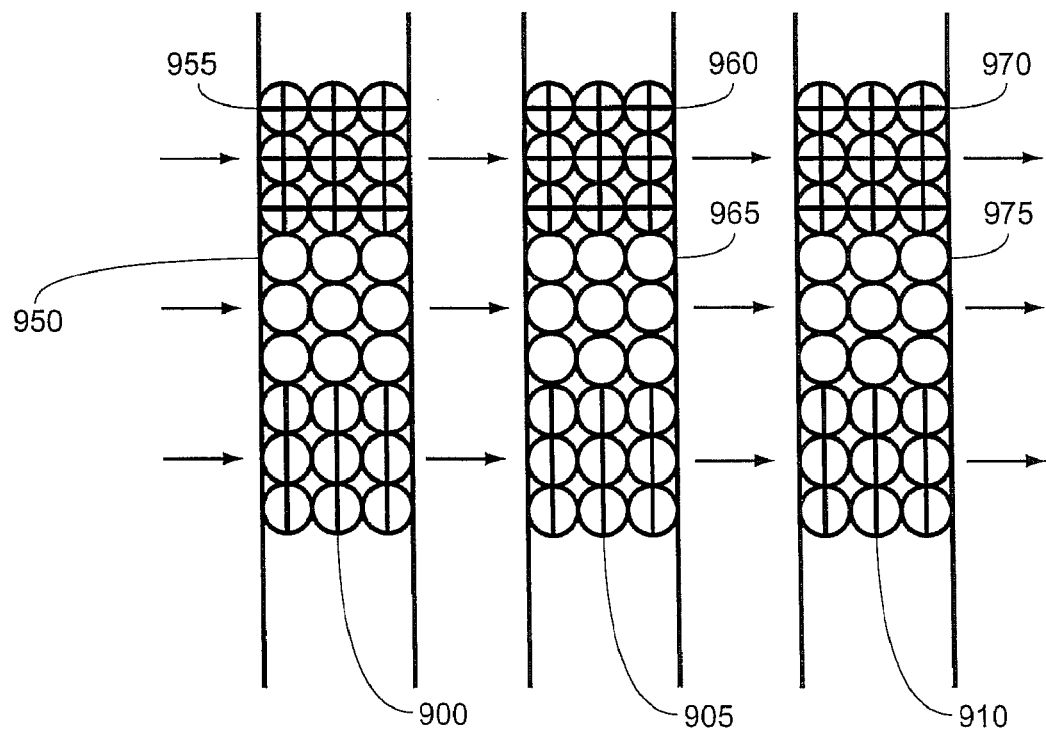

FIG. 9A shows an expanded cross-sectional view of particle packets within deep channels having an intersecting broad shallow channel. In particular, particle sets 900-910 are shown in channels 815-825, i.e., the view is a cross section of a portion of FIG. 8 comprising the channels. Flow of reagents is through broad channel 915, across particle sets 900-910. As depicted, body 801 comprises upper layer 930 and lower layer 940. FIG. 9B shows essentially the same elements in an expanded top view, additionally depicting particle packets 950-975.

Figure 10:
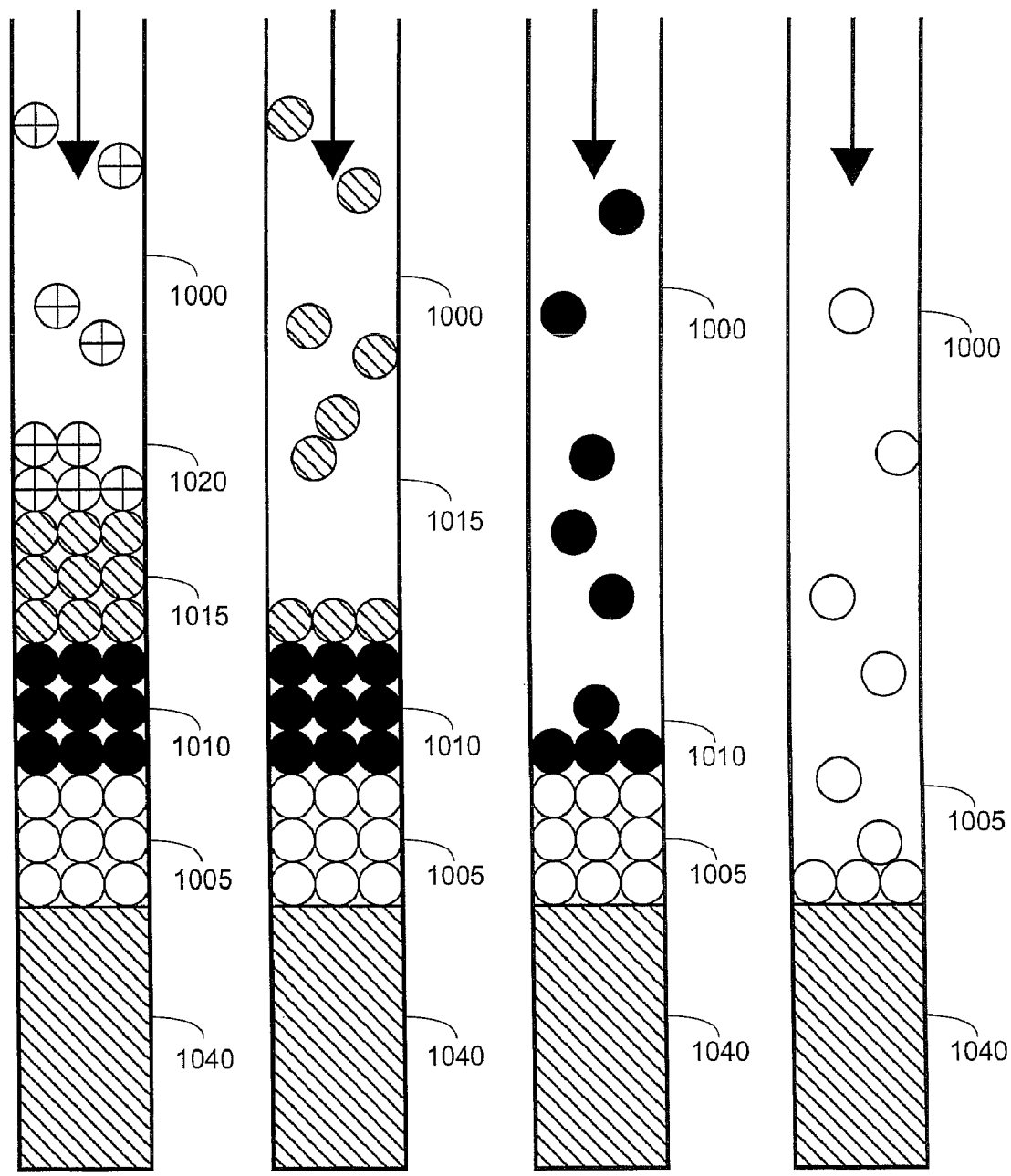
FIG. 10 is a schematic illustration of a top view of a device showing loading of bead packets.

FIG. 10 shows sequential loading of particle sets or packets into a channel. Particle set 1005 is flowed through channel 1000 until blocked by particle retention element 1040. Over time, particle sets 1010-1020 are accessed from a particle library, with each particle set abutting the previously loaded particle set(s). Particle sets 1005-1020 are optionally the same or different sizes. Particle retention element 1040 is optionally a sintered glass frit, glass, plastic, a fixed set of particles, e.g., epoxy coated particles, or the like. Typically, particle retention element 1040 is a porous barrier that has a pore size smaller than the mean diameter of the particle sets of interest, e.g., particle sets 1005-1020.

Figure 11A:
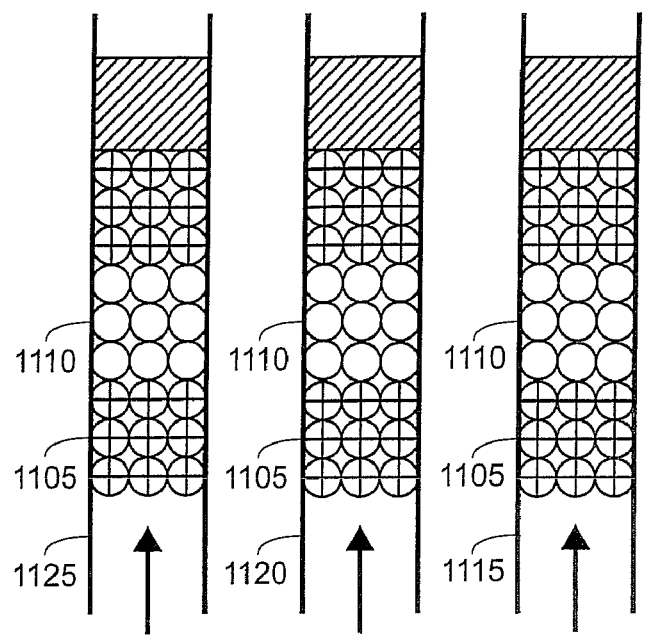
FIG. 11, panels A, B and C, show schematic illustrations of alternate bead packet loading embodiments. Panel A is a top view. Panel B is a top view. Panel C is a top view.
Figure 11B:
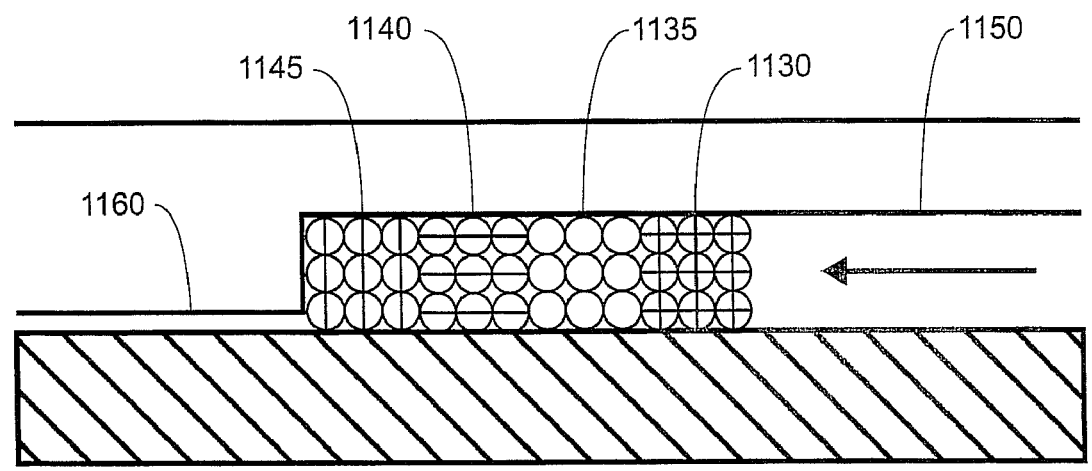
Figure 11C:
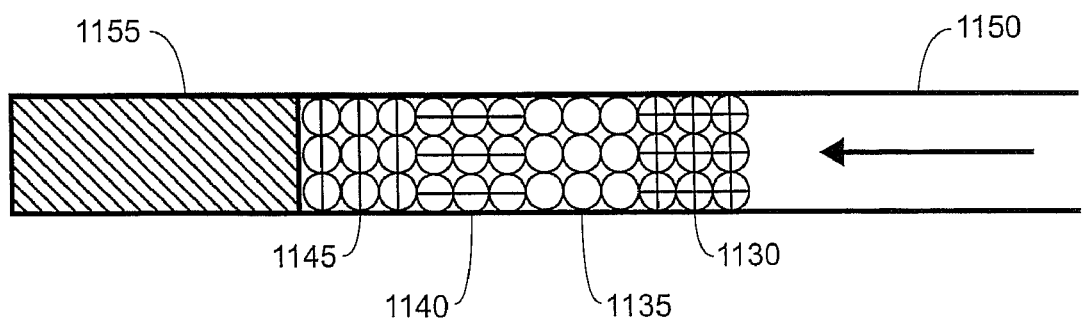

FIG. 11, panel A, shows a parallel particle array in which sample particle sets 1105 are separated by blank particle sets 1110 in channels 1115-1125. Panel B shows particle sets 1130-1145 in particle retention region 1150 abutting narrow channel region 1160. Panel C depicts an alternate embodiment in which particle sets 1130-1145 are held in particle retention region 1150 which abuts physical barrier 1155.

Figure 12:
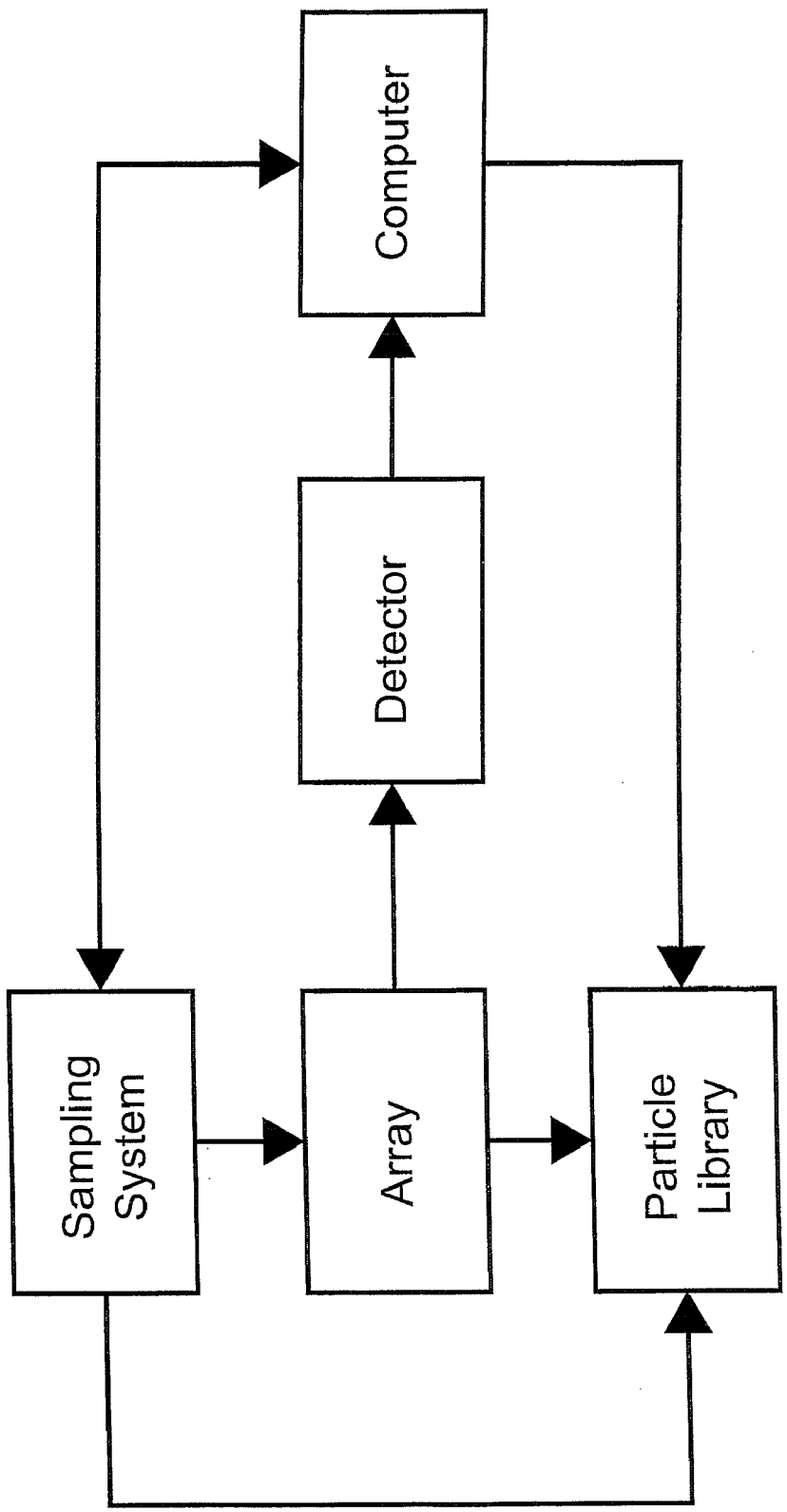
FIG. 12 is a schematic of a system comprising a computer, detector, array, sampling system, and particle library.
Figure 13:
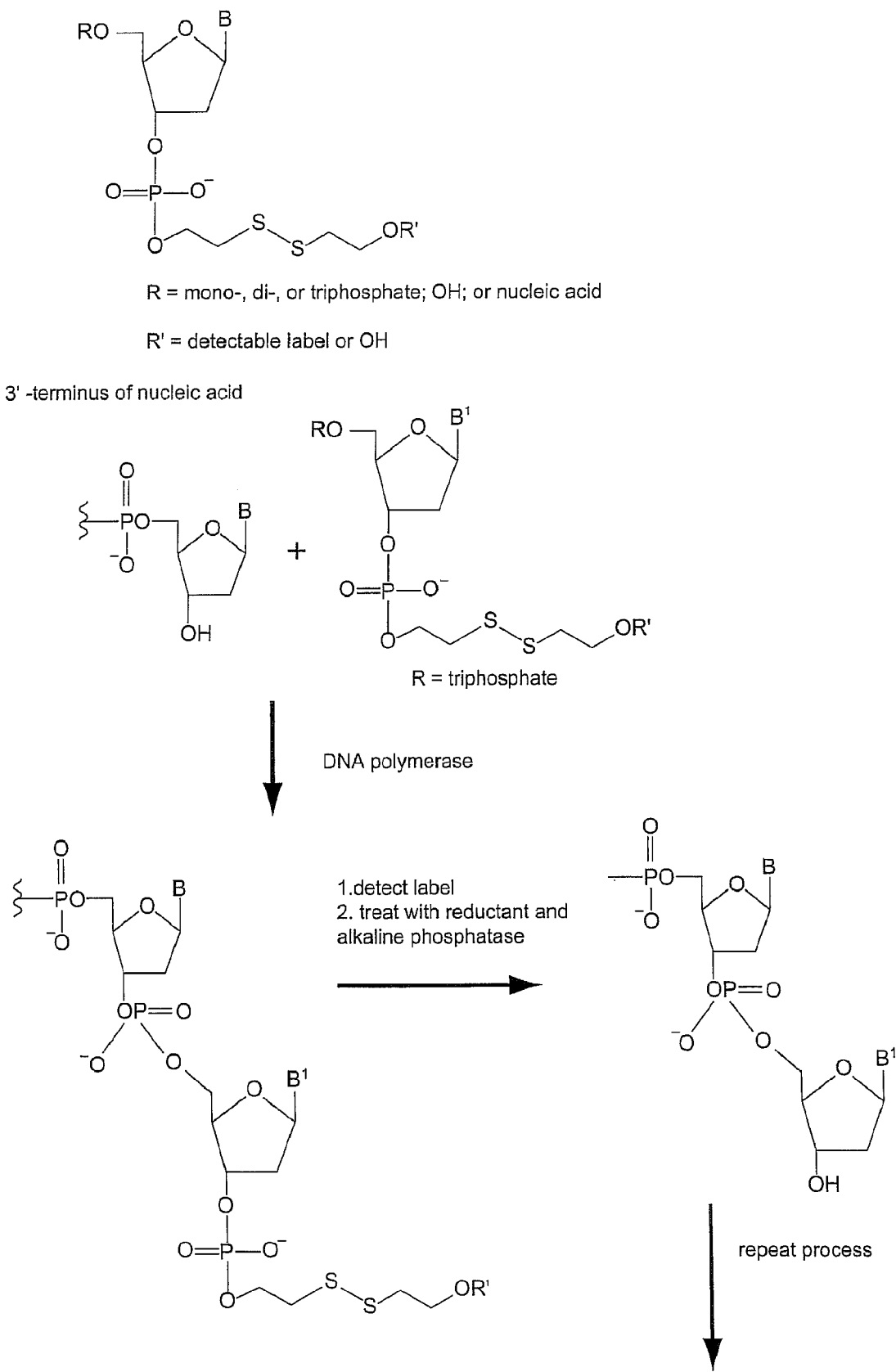
FIG. 13 is a schematic of a reversible terminator labeling strategy.

FIG. 12 shows a schematic integrated system of the invention. A computer or other microprocessing device directs materials from a sample system to an array for analysis. If appropriate to the assay, array members are directed from a particle library to the array to comprise or modify the array. The selection of particle members is optionally in response to an assay signal from the array. In general, assay signals are directed from the array to a detector which detects the signals. The signal information is converted to a digital format and sent to the computer, which reads and/or stores the information. Optionally, the information is used to select additional samples by or from the sampling system and/or additional particle sets from the particle library.

For example, during operation of the integrated system illustrated in FIG. 12, an array is formed by accessing a particle library, following an instruction set provided by the computer. The computer directs flow of fluidic (or particulate) reagents to the array through the sampling system (e.g., a system comprising a sipper channel which contacts and sips fluid from a relevant source of material, e.g., a micro titer plate). The fluidic reagents interact with the array members, providing a detectable signal. The signal is detected by the detector and converted into digital information which is stored and/or manipulated by the computer. Optionally, the digital information is used to provide the logical basis for selecting additional array or fluidic or particulate reagents from the particle library and/or through the sampling system. In these cases, the computer selects the additional array or fluidic or particulate reagent(s) and directs flow to the array and or modification or movement of the array.

Particle Stacking

As noted above, the particle retention region can take any of a number of forms in the present invention. For example, in one embodiment, a first set of particles is flowed into a microfluidic region (e.g., channel region, chamber, etc.) having a region with sufficiently small dimension to inhibit movement of the first particle set. The first particle set stacks against the small dimensioned region of the channel. Subsequently, a second, third, fourth . . . nth set of particles can be moved into the channel, where they will stack against, e.g., the first particle set. Even though the second . . . nth particle sets can be small enough to pass through the small dimensioned region of the channel, they are retained by stacking against the first particle set. Thus, the first particle set acts as a matrix preventing passage of subsequent particle sets. In this embodiment, each set of stacked particles is larger in diameter than the typical voids between the particles of the adjacent set. Thus, large retention particles can be trapped in a region of a microfluidic device and medium sized particles can then be stacked next to the large particles, where the medium sized particles are larger in dimension than the voids between the large particles. Subsequently, small particles can be stacked next to the medium sized particles, where the small particles are larger in diameter than the voids between the medium sized particles. Optionally, the small particles can be smaller than the voids between the large particles, as they will be blocked from downstream flow by the medium sized particles. Even smaller particles can be stacked next to the small particles, etc. Of course, large particles can also be stacked next to fixed or otherwise retained small particles, as long as the large particles cannot pass between the voids of the stacked or fixed small particles.

For example, beads having a cross-section of about 100 μm to about 200 μm are optionally used to form a fixed porous matrix or barrier in a microchannel. The porous matrix is optionally used to capture or retain smaller particles, e.g., particles comprising a cross-section of about 30 μm to about 80 μm, e.g., a 40 μm particle set. Even smaller particles, e.g., particles having a cross-section less than 30 μm, e.g., about 5 μm to about 11 μm, are then captured and retained, e.g., by the second particle set, i.e., the 40 μm particle set.

There are several advantages to embodiments where particle sets are retained by other particle sets, rather than simply by e.g., physical dimensions of the microfluidic system in which the particles are flowed. For example, the particle retention region is switchable in these configurations, providing for dynamic construction and removal of the arrays and of the particle retention region (advantages of switchable arrays are set forth supra, including, e.g., creation of "smart" and "programmable" particle arrays). Another advantage to this configuration is that particles of extremely small dimensions can be used in the second . . . nth position, which increases the diversity of particle types which are accessible by this approach.

Small particles also have properties which are, themselves, advantageous for some embodiments. For example, several small particles have significantly more surface area than a single large particle that occupies the same volume as the smaller particles. This increase in surface area allows attachment/association of a greater number of molecules to the particle, increasing the density of the molecules of interest in the array. This is useful, e.g., for detecting assay signals which result from interaction with the molecules of interest, i.e., for increasing the signal-to-noise ratio of assay signals in the assay.

For example, in one embodiment, a linear array of beads is made in a microfluidic channel by stacking beads of a diameter larger than the depth of the downstream channel created by a shelf, raised area, narrowed area, or other constriction within the channel (or other microfluidic structural element such as a chamber, cavity or the like). The size of the beads determines the surface area and binding capacity of the beads. The available binding capacity of the array is increased by stacking beads of a smaller diameter adjacent to the larger diameter beads, such that the diameter of the smaller diameter beads is larger than the voids between the larger diameter beads. For example, in one embodiment, a selected set of 4.4 micron beads have surface area of, roughly, $1.286*10^{12}$ $um^2/g$ and the spaces between the beads are approximately 1.8 microns. Packing beads of 2.5 microns next to the 4.4 micron beads provides about 1.7 times as much surface area per unit volume as the 4.4 micron beads. This procedure is optionally repeated with increasing surface area as the adjacent bead packages become smaller and smaller.

In a similar aspect, magnetic particles or affinity particles can be used to create particle retention regions for non-magnetic/non affinity particles. In these embodiments, the first particle set (which is, e.g., a magnetic particle (i.e., a particle which generates a magnetic field or which is attracted to a magnetic field), or an affinity particle) is flowed into the particle retention region where it is retained by magnetic or affinity forces (e.g., covalent or non-covalent chemical bonding between the particle or molecules disposed on the particle and a region of the relevant microfluidic system). Second, third . . . nth particle sets are flowed into contact with the fixed particle, where the fixed particle acts as a retention element to block flow of the fixed particles. As above, small particles are typically stacked next to fixed or otherwise retained larger particles, e.g., where the small particles cannot pass between the voids of the stacked or fixed larger particles (of course, the small particles can be magnetic or affinity particles, with larger particles stacking against the fixed smaller particles as well).

As described supra, particles can be essentially any size or shape. In embodiments where arrays are made by stacking of adjacent sets of particles, it is desirable for sets to be of sufficient diameter that they cannot flow between adjacent particle sets. Thus, in one typical aspect, the smallest dimension of a set of particles is larger than the voids between the adjacent downstream particle set.

Number and Types of Array Members

The number of ordered sets constituting the array depends on the selected application. For example, as discussed in more detail herein, one exemplar array for sequencing nucleic acids comprises about 2, 3, or 4 sets of particles (e.g., beads, cells, microspheres, etc.). In other implementations, 5, 10, 50, 100, 500, 1000, 5,000, 10,000, 50,000 or even 100,00 or more different sets of particles can be present in the arrays. The precise number of particles in an array depends on the intended use of the array. For example, larger arrays are especially useful, e.g., in screening molecular libraries against one or more targets bound to the member particles of the particle sets. Smaller arrays can be used as to screen a smaller number of targets, as is common, e.g., in diagnostic applications, where one or a few targets (e.g., nucleic acids corresponding to various disease states, such as altered levels or altered types of oncogene products, p53, presence of infectious organisms (HIV and other viruses, bacteria, etc.) are desirably screened.

The array components (i.e., particles) of the arrays of the invention can be essentially any discreet material which can be flowed through a microscale system. Example particles include beads and biological cells. For example, polymer beads (e.g., polystyrene, polypropylene, latex, nylon and many others), silica or silicon beads, clay or clay beads, ceramic beads, glass beads, magnetic beads, metallic beads, inorganic compound beads, and organic compound beads can be used. An enormous variety of particles are commercially available, e.g., those typically used for chromatography (see, e.g., the 1999 Sigma "Biochemicals and Reagents for Life Sciences Research" Catalog from Sigma (Saint Louis, Mo.), e.g., pp. 1921-2007; The 1999 Suppleco "Chromatography Products" Catalogue, and others), as well as those commonly used for affinity purification (e.g., Dynabeads™ from Dynal, as well as many derivatized beads, e.g., various derivatized Dynabeads™ (e.g., the various magnetic Dynabeads™, which commonly include coupled reagents) supplied e.g., by Promega, the Baxter Immunotherapy Group, and many other sources).

A wide variety of particles useful in the present invention include those used as components of sieving and molecular partition matrixes in the art. Many such matrixes are available, and can be used to constitute particle arrays in the apparatus of the invention. For example, a variety of sieving matrixes, partition matrixes and the like are available from Supelco, Inc. (Bellefonte, Pa.; see, e.g., the 1997 (or later) Suppleco catalogue). Common matrixes which are useful in the present invention include those generally used in low pressure liquid chromatography, gel electrophoresis and other liquid phase separations. Matrix materials designed primarily for non-liquid phase chromatography are also useful in certain contexts, as the materials often retain particulate characteristics when suspended in fluids. For a discussion of electrophoresis matrixes see, e.g., Weiss (1995) Ion Chromatography VCH Publishers Inc.; Baker (1995) Capillary Electrophoresis John Wiley and Sons; Kuhn (1993) Capillary Electrophoresis: Principles and Practice Springer Verlag; Righetti (1996) Capillary Electrophoresis in Analytical Biotechnology CRC Press; Hill (1992) Detectors for Capillary Chromatography John Wiley and Sons; Gel Filtration: Principles and Methods (5th Edition) Pharmacia; Gooding and Regnier (1990) HPLC of Biological Macromolecules Methods and Applications (Chrom. Sci. Series, volume 51) Marcel Dekker and Scott (1995) Techniques and Practices of Chromatography Marcel Dekker, Inc.

Commercially available low pressure liquid chromatography media suitable as particulate material (i.e., material for making particle sets) in a variety of applications include, e.g., non-ionic macroreticular and macroporous resins which adsorb and release components based upon hydrophilic or hydrophobic interactions, such as Amberchrom resins (highly cross-linked styrene/divinylbenzene copolymers suitable for separation of peptides, proteins, nucleic acids, antibiotics, phytopharmacologicals, and vitamins); the related Amberlite XAD series resins (polyaromatics and acrylic esters) and amberchroms (polyaromatic and polymethacrylates) (manufactured by Rohm and Haas, available through Suppleco); Diaion (polyaromatic or polymethacrylic beads); Dowex (polyaromatics or substituted hydrophilic functionalized polyaromatics) (manufactured by Dow Chemical, available through Suppleco); Duolite (phenol-formaldehyde with methanolic functionality), MCI GEL sephabeads, supelite DAX-8 (acrylic ester) and Supplepak (polyaromatic) (all of the preceding materials are available from Suppleco). For a description of uses for Amberlite and Duolite resins, see, Amberlite/Duolite Anion Exchange Resins (Available from Suppleco, 1997 Cat No. T412141). Gel filtration chromatography matrixes are also suitable, including sephacryl, sephadex, sepharose, superdex, superose, toyopearl, agarose, cellulose, dextrans, mixed bead resins, polystyrene, nuclear resins, DEAE cellulose, Benzyl DEA cellulose, TEAE cellulose, and the like (Suppleco).

Gel electrophoresis media comprising particulate material useful in making particle sets include silica gels such as Davisil Silica, E. Merck Silica Gel, Sigma-Aldrich Silica Gel (all available from Suppleco) in addition to a wide range of silica gels available for various purposes as described in the Aldrich catalogue/handbook (Aldrich Chemical Company (Milwaukee, Wis.)). Preferred gel materials include agarose based gels, various forms of acrylamide based gels (reagents available from, e.g., Suppleco, SIGMA, Aldrich, SIGMA-Aldrich and many other sources) colloidal solutions such as protein colloids (gelatins) and hydrated starches.

A variety of affinity media for purification and separation of molecular components are also available, including a variety of modified silica gels available from SIGMA, Aldrich and SIGMA-Aldrich, as well as Suppleco, such as acrylic beads, agarose beads, Mono beads, cellulose, sepharose, sepharose CL, toyopearl or the like chemically linked to an affinity ligand such as a biological molecule. A wide variety of activated matrixes, amino acid resins, avidin and biotin resins, carbohydrate resins, dye resins, glutathione resins, hydrophobic resins, immunochemical resins, lectin resins, nucleotide/coenzyme resins, nucleic acid resins, and specialty resins are available, e.g., from Suppleco, SIGMA, Aldrich or the like. See also, Hermanson et al. (1992) Immobilized Affinity Ligand Techniques Academic Press.

Other particulate media commonly used, e.g., in chromatography are also adaptable to the present invention, including activated aluminas, carbopacks, carbosieves, carbowaxes, chromosils, DEGS, Dexsil, Durapak, Molecular Sieve, OV phases, porous silica, chromosorb series packs, HayeSep series, Porapak series, SE-30, Silica Gel, SP-1000, SP-1200, SP-2100, SP-2250, SP-2300, SP2401, Tenax, TCEP, supelcosil LC-18-S and LC-18-T, Methacrylate/DVBm, polyvinylalcohols, napthylureas, non-polar methyl silicone, methylpolysiloxane, poly(ethylene glycol)biscyanopropyl polysiloxane and the like.

Ion exchange chromatography resins comprising particulate material are commercially available, including from EM Separations (Gibbstown, N.J.), BioSepra (Marlborough, Mass.), Polymer Laboratories (Amherst, Mass.), Perspective Biosystems (Cambridge, Mass.), Toso Haas (Montgomeryville, Pa.) and Pharmacia (Uppsala, Sweden).

As noted herein, the definition for particles as intended herein includes both biological and non-biological particle material. Thus, cells are included within the definition of particles for purposes of the present invention.

Cell based microfluidic assays are described in a variety of publications by the inventors and their co-workers, including, Parce et al. "High Throughput Screening Assay Systems in Microscale Fluidic Devices" WO 98/00231 and Knapp et al. "Closed Loop Biochemical Analyzers" (WO 98/45481; PCT/US98/06723). It is expected that one of skill is fully able to culture cells and introduce them into microfluidic systems. In addition to Parce et al. and Knapp et al., many references are available for the culture and production of many cells, including cells of bacterial, plant, animal (especially mammalian) and archebacterial origin. See e.g., Sambrook, Ausubel, and Berger (all supra), as well as Freshney (1994) Culture of Animal Cells, a Manual of Basic Technique, third edition Wiley-Liss, New York and the references cited therein, Humason (1979) Animal Tissue Techniques, fourth edition W.H. Freeman and Company; Ricciardelli, et al., (1989) *In Vitro Cell Dev. Biol.* 25:1016-1024; Payne et al. (1992) Plant Cell and Tissue Culture in Liquid Systems John Wiley & Sons, Inc. New York, N.Y. (Payne); Gamborg and Phillips (eds) (1995) Plant Cell, Tissue and Organ Culture; Fundamental Methods Springer Lab Manual, Springer-Verlag (Berlin Heidelberg N.Y.) (Gamborg); and Atlas and Parks (eds) The Handbook of Microbiological Media (1993) CRC Press, Boca Raton, Fla. (Atlas). Additional information for plant cell culture is found in available commercial literature such as the Life Science Research Cell Culture Catalogue (1998) from Sigma-Aldrich, Inc (St Louis, Mo.) (Sigma-LSRCCC) and, e.g., the Plant Culture Catalogue and supplement (1997) also from Sigma-Aldrich, Inc (St Louis, Mo.) (Sigma-PCCS). One particularly preferred use for cell-based microfluidic assays is to screen binding and/or internalization of cell ligands, e.g., cell receptor ligands, drugs, co-factors, etc. This screening is considerably facilitated by arraying different cell sets into arrays of cells, which can then have reagent trains comprising any factor to be tested for in vitro cellular activity flowed across the cell sets. Of course, cells can also be present in reagent trains and passed into contact with other array members.

Cells can exist as sets of particles in a variety of formats in the present invention. For example, cells can be fixed to solid supports such as beads or other microparticles. Thus, arrays of the invention can include heterogeneous particles comprising solid supports and cells or other components of interest. Cells can also be trapped using strategies similar to those described herein for particles generally, i.e., by physical trapping mechanisms. In addition, as cells comprise surface proteins and other molecules, it is convenient to fix cell binding molecules (cell receptor ligands, cell wall binding molecules, antibodies, etc.) either to regions of the channels of the microfluidic device, or to particles which are then fixed or localized in position by the methods described herein.

The array particles can have essentially any shape, e.g., spherical, helical, spheroid, rod-shaped, cone-shaped, cubic, polyhedral, or a combination thereof (of course they can also be irregular, as is the case for cell-based particles). In addition, the particles can be a variety of sizes. Typically, the particles are about 0.1 µm to about 500 µm. Alternatively, the particles are about 0.5 µm to about 50 µm or about 1 µm to about 20 µm. Particles are optionally coupled to reagents, affinity matrix materials, or the like, e.g., nucleic acid synthesis reagents, peptide synthesis reagents, polymer synthesis reagents, nucleic acids, nucleotides, nucleobases, nucleosides, peptides, amino acids, monomers, cells, biological samples, synthetic molecules, or combinations thereof. Particles optionally serve many purposes within the arrays, including acting as blank particles, dummy particles, calibration or marker particles, capture devices for low concentration reagents, sample particles, reagent particles and test particles.

Linking Chemistries

The particles within the arrays of the invention can present a solid or semi-solid surface for any of a variety of linking chemistries, allowing the incorporation of biological and chemical components of interest into the particle members of the arrays. A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that may be employed include papers, ceramics, such as glass, metals, metalloids, semiconductive materials, cements, or the like. In addition, substances that form gels, such as proteins (e.g., gelatins), lipopolysaccharides, silicates, agarose and are also optionally used.

A wide variety of linking chemistries are available for linking molecules to a wide variety of solid or semi-solid particle support elements. These chemistries can be performed in situ (i.e., in the microfluidic system, by flowing appropriate reagents, e.g., nucleic acids, proteins, and samples present in low concentrations, into contact with the particles, or vice-versa), or outside of a microfluidic environment, e.g., prior to introduction of the particles into the microfluidic system. It is impractical and unnecessary to describe all of the possible known linking chemistries for linking molecules to a solid support. It is expected that one of skill can easily select appropriate chemistries, depending on the intended application.

In one preferred embodiment, the particles of the invention comprise silicate elements (e.g., glass or silicate beads). An array of silicon-based molecules appropriate for functionalizing surfaces are commercially available. See, for example, Silicon Compounds Registry and Review, United Chemical Technologies, Bristol, Pa. Additionally, the art in this area is very well developed and those of skill will be able to choose an appropriate molecule for a given purpose. Appropriate molecules can be purchased commercially, synthesized de novo, or it can be formed by modifying an available molecule to produce one having the desired structure and/or characteristics.

The substrate linker attaches to the solid substrate through any of a variety of chemical bonds. For example, the linker is optionally attached to the solid substrate using carbon-carbon bonds, for example via substrates having (poly)trifluorochloroethylene surfaces, or siloxane bonds (using, for example, glass or silicon oxide as the solid substrate). Siloxane bonds with the surface of the substrate are formed in one embodiment via reactions of derivatization reagents bearing trichlorosilyl or trialkoxysilyl groups. The particular linking group is selected based upon, e.g., its hydrophilic/hydrophobic properties where presentation of an attached polymer in solution is desirable. Groups which are suitable for attachment to a linking group include amine, hydroxyl, thiol, carboxylic acid, ester, amide, isocyanate and isothiocyanate. Preferred derivatizing groups include aminoalkyltrialkoxysilanes, hydroxyalkyltrialkoxysilanes, polyethyleneglycols, polyethyleneimine, polyacrylamide, polyvinylalcohol and combinations thereof.

By way of example, the reactive groups on a number of siloxane functionalizing reagents can be converted to other useful functional groups:

1. Hydroxyalkyl siloxanes (Silylate surface, functionalize with diborane, and H2O2 to oxidize the alcohol);
    a. allyl trichlorosilane→→3-hydroxypropyl
    b. 7-oct-1-enyl trichlorchlorosilane→→8-hydroxyoctyl
2. Diol (dihydroxyalkyl) siloxanes (silylate surface and hydrolyze to diol)
    a. (glycidyl trimethoxysilane→→(2,3-dihydroxypropyloxy)propyl
3. Aminoalkyl siloxanes (amines requiring no intermediate functionalizing step)
    a. 3-aminopropyl trimethoxysilane→aminopropyl
4. Dimeric secondary aminoalkyl siloxanes
    a. bis(3-trimethoxysilylpropyl)amine→bis(silyloxylpropyl)amine. See, for example, Leyden et al., Symposium on Silylated Surfaces, Gordon & Breach 1980; Arkles, Chemtech 7, 766 (1977); and Plueddemann, Silane Coupling Reagents, Plenum, N.Y., 1982. These examples are illustrative and do not limit the types of reactive group interconversions which are useful in conjunction with the present invention. Additional starting materials and reaction schemes will be apparent to those of skill in the art.

The components which can be attached to a derivatized particle surface include peptides, nucleic acids, mimetics, large and small organic molecules, polymers and the like. For example, moieties bearing a permanent charge or a pH dependent charge are useful in practicing the present invention. For example, the charged group can be a carboxylate, quaternary amine or protonated amine that is a component of an amino acid that has a charged or potentially charged side chain. The amino acids can be either those having a structure which occurs naturally or they can be of unnatural structure (i.e., synthetic). Useful naturally occurring amino acids include, arginine, lysine, aspartic acid and glutamic acid. Surfaces utilizing a combination of these amino acids are also of use in the present invention. Further, peptides comprising one or more residues having a charged or potentially charged side chain are useful coating components and they can be synthesized utilizing arginine, lysine, aspartic acid, glutamic acid and combinations thereof. Useful unnatural amino acids are commercially available or can be synthesized utilizing art-recognized methodologies. In those embodiments in which an amino acid moiety having an acidic or basic side chain is used, these moieties can be attached to a surface bearing a reactive group through standard peptide synthesis methodologies or easily accessible variations thereof. See, for example, Jones, Amino Acid and Peptide Synthesis, Oxford University Press, Oxford, 1992. In addition, nucleic acids attached to a particle surface are optionally sequenced or used as a calibration particle or marker.

Linking groups can also be placed on the particles of the invention. Linking groups of use in the present invention can have a range of structures, substituents and substitution patterns. They can, for example be derivatized with nitrogen, oxygen and/or sulfur containing groups which are pendent from, or integral to, the linker group backbone. Examples include, polyethers, polyacids (polyacrylic acid, polylactic acid), polyols (e.g., glycerol), polyamines (e.g., spermine, spermidine) and molecules having more than one nitrogen, oxygen and/or sulfur moiety (e.g., 1,3-diamino-2-propanol, taurine). See, for example, Sandler et al. Organic Functional Group Preparations 2nd Ed., Academic Press, Inc. San Diego 1983. A wide range of mono-, di- and bis-functionalized poly(ethyleneglycol) molecules are commercially available and will prove generally useful in this aspect of the invention. See, for example, 1997-1998 Catalog, Shearwater Polymers, Inc., Huntsville, Ala. Additionally, those of skill in the art have available a great number of easily practiced, useful modification strategies within their synthetic arsenal. See, for example, Harris, Rev. Macromol. Chem. Phys., C25(3), 325-373 (1985); Zalipsky et al., Eur. Polym. J., 19(12), 1177-1183 (1983); U.S. Pat. No. 5,122,614, issued Jun. 16, 1992 to Zalipsky; U.S. Pat. No. 5,650,234, issued to Dolence et al. Jul. 22, 1997, and references therein.

In a preferred embodiment of the invention, the coupling chemistries for coupling materials to the particles of the invention are light-controllable, i.e., utilize photo-reactive chemistries. The use of photo-reactive chemistries and masking strategies to activate coupling of molecules to substrates, as well as other photo-reactive chemistries is generally known (e.g., for semi-conductor chip fabrication and for coupling bio-polymers to solid phase materials). The use of photo-cleavable protecting groups and photo-masking permits type switching of both mobile and fixed array members, i.e., by altering the presence of substrates present on the array members (i.e., in response to light). Among a wide variety of protecting groups which are useful are nitroveratryl (NVOC)-methylnitroveratryl (Menvoc), allyloxycarbonyl (ALLOC), fluorenylmethoxycarbonyl (FMOC), -methylnitro-piperonyloxycarbonyl (MeNPOC), —NH-FMOC groups, t-butyl esters, t-butyl ethers, and the like. Various exemplary protecting groups (including both photo-cleavable and non-photocleavable groups) are described in, for example, Atherton et al., (1989) Solid Phase Peptide Synthesis, IRL Press, and Greene, et al. (1991) Protective Groups In Organic Chemistry, 2nd Ed., John Wiley & Sons, New York, N.Y., as well as, e.g., Fodor et al. (1991) Science, 251: 767-777, Wang (1976) J. Org. Chem. 41: 3258; and Rich, et al. (1975) J. Am. Chem. Soc. 97: 1575-1579. The use of these and other photo-cleavable linking groups for nucleic acid and peptide synthesis on solid supports is a well-established methodology.

In one useful variation of these methods, solid phase arrays are adapted for the rapid and specific detection of multiple polymorphic nucleotides. Typically, a nucleic acid probe is chemically linked to a solid support and a target nucleic acid (e.g., an RNA or corresponding amplified DNA) is hybridized to the probe. Either the probe, or the target, or both, can be labeled, typically with a fluorophore. Where the target is labeled, hybridization is detected by detecting bound fluorescence. Where the probe is labeled, hybridization is typically detected by quenching of the label by the bound nucleic acid. Where both the probe and the target are labeled, detection of hybridization is typically performed by monitoring a signal shift such as a change in color, fluorescent quenching, or the like, resulting from proximity of the two bound labels. In some assay formats, the above format is inverted, with expression products being fixed to array members and probes being moved into contact with the array.

In another variation, solid-phase arrays are used to detect samples even at very low concentrations. Particles and particle arrays are very efficient at capturing molecules in a fluid stream. Therefore, they provide suitable molecule capture devices for studying systems in which a sample or reagent is in very low concentration, e.g., in single cell RNA analysis. Typical methods for studying such systems involve DNA arrays having the non-precious reagents, e.g., those available in large or adequate quantities and concentrations, spread out in defined locations across a substrate. The precious or low concentration sample, e.g., cell contents or amplification product, is typically diffused across the array, e.g., to find a hybridization partner. By attaching the precious or low concentration sample to a particle or particle array, it can be placed in a defined location and then non-precious samples are optionally flowed across the array, allowing detection of the sample at very low concentrations. For example, a few cells are optionally flowed through a capillary comprising a particle array, e.g., beads, e.g., hybridized with a capture reagent. The cells are lysed and the mRNA from the cells is captured on the particles. The capillary is then optionally used to flow reagents across the particles, e.g., hybridization reagents that bind, e.g., specifically, to the mRNA of interest, if it is present. The capillary is rinsed after each exposure and any resulting hybridization is detected, e.g., by fluorescence detection. Alternatively, the captured molecule is amplified and the product captured, e.g., immediately or in about the same vicinity to enhance the signal before bringing hybridization or probe reagents across the capture area. In other aspects, different probe reagents comprising different fluorophores are mixed to detect several components at once. Alternatively, capillary or channel surfaces are used to capture the low concentration molecule instead of particles.

In other aspects, the particles of the present invention are used as marker particles or calibration particles. For example, charged beads, e.g., to which a dye is attached, are optionally used as markers in capillary electrophoresis, especially when very low mobility is required. For example, a marker that flows slower than any sample is optionally used. Alternatively, a neutral particle or bead is used with an attachment, functional group, or linker that is charged. Typical molecules for use on the particles include, but are not limited to, molecules that are similar to the sample of interest. For example, a nucleic acid is preferably used in electrophoresis of nucleic acids. A typical DNA or RNA molecule attached to such a marker or calibration bead comprises about 10 thousand base-pairs to about 20 thousand base pairs, e.g., a 17 thousand base pair nucleic acid. The marker particle or bead is used, for example, to determine the position of one or more member of an array. For example, the marker is optionally used to determine the position of an array member that has captured a low concentration sample as described above. The particle or bead typically comprises a charged moiety or particle and a label moiety, e.g., a fluorescent dye or a charged label moiety. The label moiety is optionally detected, e.g., by fluorescence, to determine and calibrate positions of array members.

In one embodiment of this concept, an array of probes are synthesized on solid support particles constituting array members. Using typical array masking technologies and photoprotective chemistry, it is possible to generate ordered arrays of nucleic acid probes with large numbers of probes. In the embodiments of the present invention, even photomasking is unnecessary, making photoprotective chemistry particularly useful. In particular, the array members can be flowed past a light source in a selected order in the presence of selected reagents, permitting selective addition of components to the array, without actually performing chip masking. Of course, however, chip masking strategies can also be used, i.e., array members can be fixed in place and selectively exposed to light. Either method is used, for example, to place a precious sample, e.g., a sample that is only available in small amounts, in a defined location and detect it at very low concentrations.

In brief, a combinatorial strategy allows for the synthesis of arrays containing a large number of different elements such as fixed nucleic acids, using a minimal number of synthetic steps. For instance, in general in solid-phase masking technologies, it is possible to synthesize and attach all possible DNA 8-mer oligonucleotides ($4^8$, or 65,536 possible combinations) using only 32 chemical synthetic steps. In general, these procedures provide a method of producing $4^n$ different oligonucleotide probes on an array using only 4n synthetic steps. Alternatively, due to the high-throughput reaction speeds of microfluidic systems, it is possible to perform large numbers of reactions with linear or parallel fluidic manipulations in feasibly short periods of time.

As noted, light-directed combinatorial synthesis of oligonucleotide arrays on glass array members is performed with automated phosphoramidite chemistry and, optionally, chip masking techniques similar to photoresist technologies in the computer chip industry. Typically, a glass surface is derivatized with a silane reagent containing a functional group, e.g., a hydroxyl (for nucleic acid arrays) or amine group (for peptide or peptide nucleic acid arrays) blocked by a photolabile protecting group. Photolysis through a photolithographic mask, or by selective flow, e.g., in a microfluidic system past a light source, is used selectively to expose functional groups which are then ready to react with incoming photoprotected elements (e.g., for nucleic acids, 5'-photoprotected nucleoside phosphoramidites). The photoprotected elements react with those sites which are illuminated (and thus exposed by removal of the photolabile blocking group). Thus, e.g., phosphoramidites only add to those areas selectively exposed from the preceding step. These steps are repeated until the desired array of sequences has been synthesized on the array particle. Combinatorial synthesis of different molecules at different locations on the array is determined by the pattern of illumination during synthesis, relative to the array (again, the array can be mobile or fixed in the present invention) and the order of addition of coupling reagents. Monitoring of hybridization of target elements to the array is typically performed with fluorescence microscopes, laser scanning microscopes, CCD arrays or the like.

Although light-directed coupling chemistries are preferred, and described above in some detail for exemplary purposes, these are not the only feasible routes to producing arrays with a variety of different particle members. The use of microfluidic fluid movement to move reagents into contact with array members can also be used. In particular, solid surfaces are derivatized as noted above in preparation for addition of components such as nucleotide synthesis reagents, peptides, or the like. Between coupling steps, protective groups can be used as noted above. Instead of photoprotective cleavage, other cleavage agents can be used, depending on the nature of the reaction, e.g., acids, bases, or the like. Indeed, because it is possible to flow only desired reagents into contact with selected array members, it is not necessary to use blocking groups at all. The elimination of blocking groups is one of the many advantages of the present invention over standard solid phase synthesis techniques.

Array Templates

The array or reagents contacting the array can involve template hybridization reagents or the like, including a first nucleic acid which is fully or partially complementary to a second nucleic acid complexed with a particle set of the array, a first protein which specifically hybridizes to one or more component with a particle set of the array, a first antibody which specifically hybridizes to one or more component with a particle set of the array, a hybridization buffer, a blocking reagent, and a labeled probe nucleic acid. The methods optionally comprise flowing liquid reagents into contact with one or more array member and detecting the resulting hybridization of the liquid reagent to the array member.

Sequencing and PCR in Microfluidic Systems

In a preferred embodiment of the invention, the microarrays of the invention are used for sequencing nucleic acids. The devices of the invention optionally include reagents (which may be part of the array or flowed into contact with the array, e.g. in a reagent train) for performing a biological or chemical assay. The liquid reagent or array can include a nucleic acid sequencing reagent such as a liquid solution comprising a nucleotide, a liquid solution comprising a polymerase, a liquid solution comprising a dNTP, a ddNTP, a dNTP analog, or a fluorescent dNTP, a liquid solution comprising a sufurylase, a liquid solution comprising an apyrase, a liquid solution comprising inorganic phosphate, a liquid solution comprising ATP, a liquid solution comprising a thermostable polymerase, a liquid solution comprising an endonuclease, a liquid solution comprising an exonuclease, a liquid solution comprising a phosphatase, a liquid solution comprising an intercalator, a liquid solution comprising a reducing agent, a liquid solution comprising $Mg^{++}$, a liquid solution comprising a molecular crowding agent, e.g., PEG, a liquid solution comprising a buffer, a liquid solution comprising a salt, a salt, DTT, BSA, a detergent (e.g., triton or tween), chemicals to inhibit or enhance electroosmotic flow (e.g., polyacrylamide) or the like.

Standard Chain Termination Sequencing

Most DNA sequencing today is still carried out by chain termination methods of DNA sequencing. The most popular chain termination methods of DNA sequencing are variants of the dideoxynucleotide mediated chain termination method of Sanger. See, Sanger et al. (1977) Proc. Nat. Acad. Sci., USA 74:5463-5467. For a simple introduction to dideoxy sequencing, see, Current Protocols in Molecular Biology, F. M. Ausubel et al., eds., Current Protocols, a joint venture between Greene Publishing Associates, Inc. and John Wiley & Sons, Inc., (Supplement 38, current through 1998) (Ausubel), Chapter 7. Thousands of laboratories employ dideoxynucleotide chain termination techniques. Commercial kits containing the reagents most typically used for these methods of DNA sequencing are available and widely used. These methods of DNA sequencing are adaptable to the arrays of the invention. In particular, array members can comprise e.g., template nucleic acids, e.g., chemically coupled or hybridized to particle surfaces. Reagent trains comprising sequencing reagents are passed across the template nucleic acids (e.g., using electrophoresis, or electroosmotic or pressure-based reagent flow) where they contact the templates. Reaction products can be analyzed directly, or following dissociation and electrophoresis within the microfluidic system.

In addition to the Sanger methods of chain termination, new PCR exonuclease digestion methods have also been developed for DNA sequencing. Direct sequencing of PCR generated amplicons by selectively incorporating boronated nuclease resistant nucleotides into the amplicons during PCR and digestion of the amplicons with a nuclease to produce sized template fragments has been performed (Porter et al. (1997) Nucleic Acids Research 25(8):1611-1617). In the methods, 4 PCR reactions on a template are performed, in each of which one of the nucleotide triphosphates in the PCR reaction mixture is partially substituted with a 2' deoxynucleoside 5'-∀[P-borano]-triphosphate. The boronated nucleotide is stochastically incorporated into PCR products at varying positions along the PCR amplicon in a nested set of PCR fragments of the template. An exonuclease which is blocked by incorporated boronated nucleotides is used to cleave the PCR amplicons. The cleaved amplicons are then separated by size using polyacrylamide gel electrophoresis, providing the sequence of the amplicon. An advantage of this method is that it requires fewer biochemical manipulations than performing standard Sanger-style sequencing of PCR amplicons. These methods are similarly adaptable to the arrays and microfluidic systems of the invention. In particular, PCR can be performed by heating and cooling all or part of a microfluidic system.

It is expected that one of skill is familiar with fundamental sequencing methodologies applicable to the present invention. Examples of techniques for making and sequencing nucleic acids, and instructions sufficient to direct persons of skill through most standard cloning and other template preparation exercises are found in Berger and Kimmel, Guide to Molecular Cloning Techniques, Methods in Enzymology volume 152 Academic Press, Inc., San Diego, Calif. (Berger); Sambrook et al. (1989) Molecular Cloning—A Laboratory Manual (2nd ed.) Vol. 1-3, Cold Spring Harbor Laboratory, Cold Spring Harbor Press, NY, (Sambrook); and Current Protocols in Molecular Biology, F. M. Ausubel et al., eds., Current Protocols, a joint venture between Greene Publishing Associates, Inc. and John Wiley & Sons, Inc., (1997, supplement 37) (Ausubel). Basic procedures for cloning and other aspects of molecular biology and underlying theoretical considerations are also found in Lewin (1995) Genes V Oxford University Press Inc., NY (Lewin); and Watson et al. (1992) Recombinant DNA Second Edition Scientific American Books, New York. Product information from manufacturers of biological reagents and experimental equipment also provide information useful in known biological methods. Such manufacturers include the Sigma Chemical Company (Saint Louis, Mo.); New England Biolabs (Beverly, Mass.); R&D systems (Minneapolis, Minn.); Pharmacia LKB Biotechnology (Piscataway, N.J.); CLONTECH Laboratories, Inc. (Palo Alto, Calif.); ChemGenes Corp., (Waltham Mass.) Aldrich Chemical Company (Milwaukee, Wis.); Glen Research, Inc. (Sterling, Va.); GIBCO BRL Life Technologies, Inc. (Gaithersberg, Md.); Fluka Chemica-Biochemika Analytika (Fluka Chemie AG, Buchs, Switzerland); Invitrogen (San Diego, Calif.); Perkin Elmer (Foster City, Calif.); and Strategene; as well as many other commercial sources known to one of skill.

In one aspect, the generation of large nucleic acids is useful in practicing the invention, e.g., as templates fixed to array members, e.g., for sequencing long regions of nucleic acids, or for monitoring expression products by hybridization of biological materials to the fixed templates. It will be appreciated that such templates are particularly useful in some aspects where the methods and devices of the invention are used to sequence large regions of DNA, e.g., for genomics types of applications. An introduction to large clones such as YACs, BACs, PACs and MACs as artificial chromosomes is provided by Monaco and Larin (1994) Trends Biotechnol 12 (7): 280-286.

The construction of nucleic acid libraries of template nucleic acids is described in the above references. YACs and YAC libraries are further described in Burke et al. (1987) Science 236:806-812. Gridded libraries of YACs are described in Anand et al. (1989) Nucleic Acids Res. 17, 3425-3433, and Anand et al. (1990) Nucleic Acids Res. Riley (1990) 18:1951-1956 Nucleic Acids Res. 18(10): 2887-2890 and the references therein describe cloning of YACs and the use of vectorettes in conjunction with YACs. See also, Ausubel, chapter 13. Cosmid cloning is also well known. See, e.g., Ausubel, chapter 1.10.11 (supplement 13) and the references therein. See also, Ish-Horowitz and Burke (1981) Nucleic Acids Res. 9:2989-2998; Murray (1983) Phage Lambda and Molecular Cloning in Lambda II (Hendrix et al., eds) 395-432 Cold Spring Harbor Laboratory, NY; Frischauf et al. (1983) J. Mol. Biol. 170:827-842; and, Dunn and Blattner (1987) Nucleic Acids Res. 15:2677-2698, and the references cited therein. Construction of BAC and P1 libraries is well known; see, e.g., Ashworth et al. (1995) Anal Biochem 224 (2): 564-571; Wang et al. (1994) Genomics 24(3): 527-534; Kim et al. (1994) Genomics 22(2): 336-9; Rouquier et al. (1994) Anal Biochem 217(2): 205-9; Shizuya et al. (1992) Proc Natl Acad Sci USA 89(18): 8794-7; Kim et al. (1994) Genomics 22 (2): 336-9; Woo et al. (1994) Nucleic Acids Res 22(23): 4922-31; Wang et al. (1995) Plant (3): 525-33; Cai (1995) Genomics 29 (2): 413-25; Schmitt et al. (1996) Genomics 1996 33(1): 9-20; Kim et al. (1996) Genomics 34(2): 213-8; Kim et al. (1996) Proc Natl Acad Sci USA (13): 6297-301; Pusch et al. (1996) Gene 183(1-2): 29-33; and, Wang et al. (1996) Genome Res 6(7): 612-9.

In general, where the desired goal of a sequencing project is the sequencing of a genome or expression profile of an organism, a library of the organism's cDNA or genomic DNA is made according to standard procedures described, e.g., in the references above. Individual clones are isolated and sequenced, and overlapping sequence information is ordered to provide the sequence of the organism. See also, Tomb et al. (1997) Nature 539-547 describing the whole genome random sequencing and assembly of the complete genomic sequence of *Helicobacter pylori*; Fleischmann et al. (1995) Science 269:496-512 describing whole genome random sequencing and assembly of the complete *Haemophilus influenzae* genome; Fraser et al. (1995) Science 270:397-403 describing whole genome random sequencing and assembly of the complete *Mycoplasma genitalium* genome and Bult et al. (1996) Science 273:1058-1073 describing whole genome random sequencing and assembly of the complete *Methanococcus jannaschii* genome.

Recently, Hagiwara and Curtis (1996) Nucleic Acids Research 24(12):2460-2461 developed a "long distance sequencer" PCR protocol for generating overlapping nucleic acids from very large clones to facilitate sequencing, and methods of amplifying and tagging the overlapping nucleic acids into suitable sequencing templates. The methods can be used in conjunction with shotgun sequencing techniques to improve the efficiency of shotgun methods typically used in whole organism sequencing projects. As applied to the present invention, the techniques are useful for identifying and sequencing genomic nucleic acids using the arrays of the present invention. In particular, one or more component of the PCR reactions, YACs, vectorettes, or the like used in the long distance sequencer method are fixed to an array, and the array performed in a microfluidic system by flowing other components of the long distance sequencer method into contact with the fixed component on the array. This method particularly benefits from the use of arrays due to the need to organize several reactions simultaneously for the long distance sequencer method. Products can be assayed in parallel or sequentially, facilitating the selection of subsequent reaction components.

Sequencing by Incorporation/Synthesis

In a preferred embodiment, the present invention provides for sequencing by synthesis or incorporation. A number of basic sequencing by incorporation methods are known, e.g., as set forth in Hyman U.S. Pat. No. 4,971,903; Malemede U.S. Pat. No. 4,863,849; Cheeseman U.S. Pat. No. 5,302,509, and Canard U.S. Pat. No. 5,798,210. Generally, any detectable event associated with incorporation of a nucleotide can be used to monitor sequencing reactions. In sequencing by incorporation methods, incorporation of nucleotide reagents into nucleic acids (typically by a using a polymerase to extend a primer hybridized to a complementary template nucleic acid) is monitored to provide an indication of the sequence of a template nucleic acid. This can be performed by selectively adding reagents comprising labels such as bases comprising fluorescent moieties, e.g., four detectably different fluorescent moieties, to e.g., a member of an array set and monitoring incorporation of the label into the nucleic acid.

A variety of nucleotides which have fluorescent labels can be added in a base specific fashion by a polymerase. For example, Hawkins et al. U.S. Pat. No. 5,525,711 describe pteridine nucleotide analogs for use in fluorescent DNA probes. These analogs can be incorporated by, e.g., Taq polymerase, sequenase, DNA polymerase Klenow fragment, or the like.

In both sequencing methodologies and elsewhere herein, it will be recognized that fluorescent labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily derivatized for coupling to a biological molecule (Bruchez et al. (1998) Science, 281: 2013-2016). Similarly, highly fluorescent quantum dots (e.g., zinc sulfide-capped cadmium selenide) have been covalently coupled to biomolecules for use in ultrasensitive biological detection (Warren and Nie (1998) Science, 281: 2016-2018). The use of quantum dots as labels in the present invention is particularly useful, both in direct sequencing application and more generally as a labeling methodology for any system set forth herein.

In certain aspects, it is useful to reduce the fluorescence of labeled nucleic acids before adding additional labels to the nucleic acids, e.g., to reduce background fluorescence between cycles of label addition. This can be accomplished, e.g., by interspersing cycles of photobleaching between labeling steps to reduce fluorescence of previously labeled components. For example, nucleic acid template molecules are optionally attached to the surface of a microfluidic channel or to an array member, e.g., a bead or set of beads. A primer is bound to the template, e.g., by flowing the primer across the nucleic acid template. Other sequencing reagents, e.g., a polymerase and a series of nucleotides are flowed across the template, e.g., incorporating a nucleotide. For example, a solution comprising at least one of the four standard nucleotides, at least a portion of which nucleotides are labeled nucleotides, is flowed across the template. The channel is then washed, removing any unincorporated nucleotides. If a nucleotide was incorporated, a fluorescence signal associated with the incorporated nucleotide is detected, thus determining the identity of the added nucleotide and providing a portion of the sequence. The template nucleic acid is then photobleached to reduce the background level of fluorescence before repeating the procedure with another nucleotide.

In one preferred sequencing by incorporation method, label is produced indirectly, i.e., incorporation of nucleotide reagents is measured by production of a detectable label in a coupled signal reaction, e.g., when sequencing by pyrophosphate methods.

Polymerase reactions sometimes show incorporation of non-complementary bases at a low frequency, particularly when the bases are present in excess, or when complementary bases are not present. In one aspect, non-incorporatable nucleotides (e.g., analogues which lack moieties which provide for coupling to the phosphate backbone) are added to increase the fidelity of a polymerase reaction, by competing with the non-complementary bases. In addition, the non-incorporatable nucleotides reduce polymerase processivity, which is desirable, e.g., in reactions where a complementary residue is not present in the reaction mixture.

In one aspect, chain termination is reversible. See also, Cheeseman U.S. Pat. No. 5,302,509 and Canard U.S. Pat. No. 5,798,210. In one method of sequencing by synthesis, a "reversible" label is used. In particular, a terminating base comprising a label is added by a polymerase as in standard chain termination methods. The label is cleavable, e.g., by photolysis, or by exposure to heat or to one or more chemicals, e.g., a reducing agent and/or a phosphatase. Base-specific incorporation of the label is first detected and then the label is cleaved and washed from the array. Alternatively, the label; is cleaved, washed from the array and then detected. The array is then exposed to nucleotides comprising a label and the process is repeated. Sequence information is provided by assessing which nucleotides comprising a label are incorporated and compiling the information. The typical four nucleotides are optionally added in series or they are all added together in one solution. In the latter case, the four nucleotides each have a detectably different label, which is used to identify the nucleotide incorporated.

Examples of reversible chain terminating nucleotides include, but are not limited to, nucleotides with 3'-phosphate blocking groups, e.g., comprising a disulfide, and nucleotides with 3'-carbamate blocking groups. Example of such compounds include, but are not limited to compounds having the following formulas:

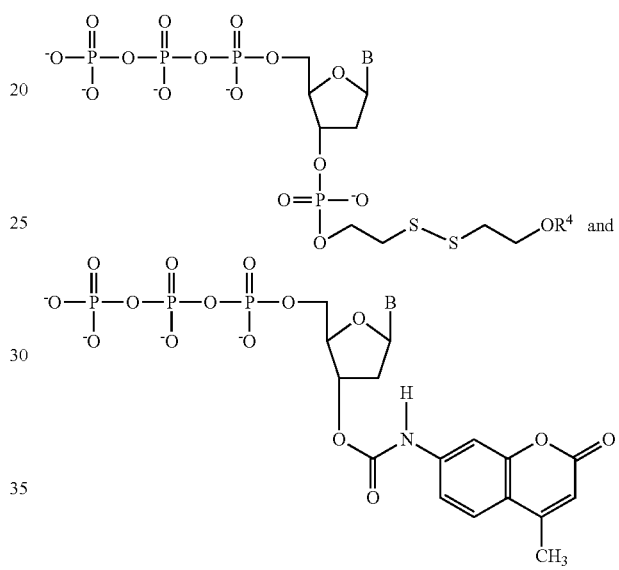

wherein B comprises a nitrogenous base and $R^4$ typically comprises a label moiety, e.g., a fluorescent label moiety. These nucleotides are added to a growing nucleotide chain by a polymerase, e.g., taq polymerase, and then the blocking group is removed to provide a 3'-OH group, to which another nucleotide is optionally added as sequencing continues.

Removal of the phosphate blocking group comprises reducing the disulfide linkage with a suitable reducing agent, e.g., including, diborane and other boron-containing reductants, dithiothreitol, and enzymes such as reductases specific for the disulfide group. The cleavage of the disulfide results in a molecule having the following formula:

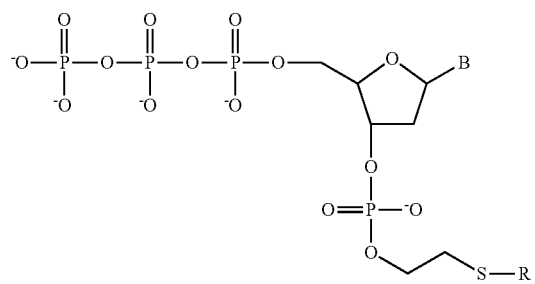

which is typically unstable and spontaneously degrades, e.g., through nucleophilic attack, providing a 3'-phosphate group.

The phosphate group is then cleaved, e.g., using an alkaline phosphatase. Cleavage of the 3'-phosphate group leaves an extendable 3'-OH group.

Removal of the carbamate typically comprises reduction of the carbamate linkage, thus producing an unblocked 3'-OH group, which is optionally extended, e.g., by addition of another dNTP.

Ribonucleic acid base monomers comprising removable labels having a disulfide linker group at the 3'-hydroxyl group are optionally prepared by normal solid or solution phase phosphoramidite chemistry, optionally in a microfluidic system. As the 3'-hydroxyl is effectively blocked by the conjugated linker arm, these monomers can then be used as a terminating residue in standard dideoxy chain termination, or can be used as reversible terminators in sequencing by synthesis protocols as noted above. The free hydroxy terminus of the linker arm is preferably derivatized with a detectable label such as a fluorescent or chemiluminescent dye or a radioactive isotope. Methods for preparing linker arms that can be incorporated into monomers or nucleic acid oligomers are discussed below in the context of nucleic acid oligomers. It is, however, understood that this is by way of example. One of skill will recognize that a linker that is appropriate for incorporation into a nucleic acid oligomer synthesis is also optionally utilized to derivatize a nucleic acid monomer.

At least two methods can be utilized to prepare nucleic acids with a disulfide linker having a detectable moiety at one terminus of the linker. In the first method, the disulfide moiety, preferably supplied by an agent such as 2-hydroxyethyl disulfide is mono-functionalized at one hydroxy terminus with a detectable group. The remaining hydroxy group is converted to a phosphoramidite. This linker arm-detectable agent conjugate can then be incorporated into a normal nucleic acid synthetic cycle.

A second method, exemplified below, allows a trityl protected linker to be tethered to a growing nucleic acid chain. The trityl group is subsequently removed in a normal nucleic acid deprotection cycle and the liberated hydroxy group is conjugated to another base or to a detectable moiety.

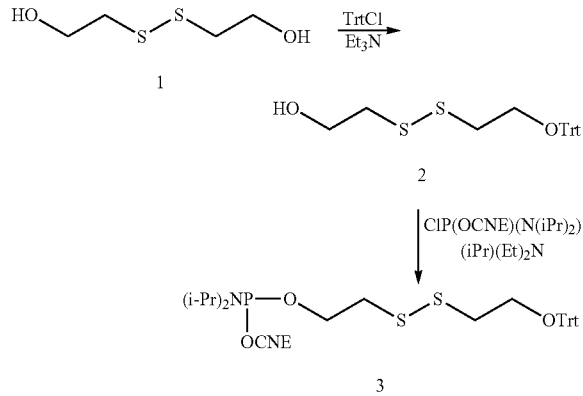

Synthesis of monotrityl-2-hydroxyethyl disulfide (2)

2-hydroxyethyl disulfide (1, Aldrich Chemical Co.) is monotritylated by the action of tritychloride and a base such as triethylamine. The reaction is weighted towards production of the monotrityl derivative by using a substantial stoichiometric excess (3-5 fold) of 2-hydroxyethyl disulfide relative to tritylchloride. The reaction is typically carried out in ethyl acetate of a chlorinated hydrocarbon at room temperature. The monotritylated product will exhibit markedly different chromatographic behavior than both unreacted tritylchloride and the ditritylated derivative. Thus, the monotritylated derivative can be easily purified by, for example, silica gel chromatography, optionally in a microfluidic system.

Synthesis of monotrityl-2-hydroxyethyl
disulfide-2-cyanoethyldiisopropyl-phosphoramidite
(3)

The purified monotrityl 2-hydroxyethyl disulfide is converted to a phosphoramidite appropriate for inclusion into solid phase nucleic acid synthesis as follows. The montrityl compound is contacted with 2-cyanoethyldiisopropylchlorophosphoramidite in the presence of an organic base such as diisopropylethylamine. As the reaction proceeds, amine hydrochloride is produced and precipitates from the reaction medium. When the reaction is complete, the solid is removed by filtration and the organic layer is washed with water at approximately neutral pH. The solvent is removed by evaporation and the crude product is purified by silica gel chromatography to provide the desired product.

In one embodiment, the phosphoramidite derivative is brought into solution in, for example, acetonitrile and placed into a reactant vessel on an art-recognized nucleic acid synthesis apparatus. The disulfide linker arm is added to the growing chain at any desired point in the synthesis. The use of the phosphoramidite derivative allows the disulfide linker to be added in a manner identical to any other nucleic acid base phosphoramidite. Following the addition of the disulfide linker, the trityl group is removed using a standard deprotection cycle and, if desired, chain elongation can then proceed.

In any of the embodiments herein which comprise fixation of targets to array members, the targets can be related (e.g., sequence fragments of a single clone) or unrelated. In embodiments where the sequences are related, the system optionally includes a microprocessor for compiling overlapping sequence information.

Direct Sequencing—Real Time Pyrophosphate

One recent approach to sequencing by synthesis is set forth in Ronaghi et al. (1998) "A Sequencing Method Based on Real Time Pyrophosphate" Science 281:363-364 (See also, Nyren and Uhlen (1996) Anal. Biochem. 242:84-89 and (1993) 208:171-175 and Canard U.S. Pat. No. 5,798,509). In this method, four nucleotides are added stepwise to a template nucleic acid hybridized to a primer. In the applications of the present invention, templates are optionally fixed to one or more particle members of the arrays. A polymerase adds a nucleotide to the primer based upon standard base-pairing rules and standard polymerase activity. The addition of a nucleotide to the primer results in the release of an inorganic pyrophosphate from the nucleotide. An ATP sulfurylase enzyme is used to convert the inorganic pyrophosphate into ATP or an ATP analogue (e.g., comprising a sulfur atom). A luciferase enzyme releases light in the presence of the ATP, providing an indication as to when a nucleotide is added to the primer. To remove excess ATP from the system, an apyrase is added to degrade the ATP into AMP+2PPi between dNTP addition cycles. The apyrase also degrades any nucleotide from the system which is not added to the primer. Any or all of these reagents can be present in a reagent train which passes over particle members comprising template, or, alternatively can be themselves fixed to array members, where a reagent train comprising the template is passed across the array members. As described above, chemistries for fixing either nucleic acids or proteins (or both) to any of a variety of array members is well known. Optionally, the dATP for incorporation into growing nucleic acids is α-thio dATP which can be incorporated by polymerase, but not by luciferase, thus reducing background signal production in the assay.

Indeed, one advantage of the present invention is that it makes the reaction outlined by Ronaghi et al. much more practical. In the Ronaghi et al. reference, due to the use of relatively crude enzyme fractions and fluidic inefficiencies, signal to noise ratios gradually decreased as the reaction proceeded (due in part to incomplete washing of reactants and products between steps), making it difficult to read longer nucleic acid templates. In contrast, using the present invention, it is possible to isolate completely the relevant reagents, and to wash them from the templates using microfluidic fluid movement.

One additional aspect of the present invention is a new pyrophosphate sequencing reaction. In this new sequencing reaction, PPi is converted to a thio analogue form of ATP with a sulfurylase. The ATP is combined with glucose and converted to glucose-6-phosphate+NADP and ADP. Glucose-6-phosphate dehydrogenase is used to produce NADPH+6 phosphoglutamate. The ADP is converted into ATP by addition of phosphoenoyl pyruvate (PEP) and a phosphokinase enzyme. ATP formation can be monitored with luciferase. Preferably, NADPH formation can be monitored by monitoring fluorescence. In essence, as long as PEP is present in the reaction, this set of reactions provides a signal amplification cycle by producing additional ATPs. This is helpful in luciferase mediated signals, because luciferase produces a relatively low level of detectable signal, e.g., as compared to fluorescence.

Maxam Gilbert Sequencing

In addition to chain termination and coupled enzymatic methods, chemical nucleic acid degradation methods have been in use for specialized applications; see, Maxam and Gilbert (1980) in Grossman and Moldave (eds.) Academic Press, New York, Methods in Enzymology 65:499-560. As with the sequencing methodologies noted above, the Maxam Gilbert method is entirely amenable to use with the arrays of the invention. In particular, the template can be fixed to an array (covalently or non-covalently) and selectively degraded by the Maxam Gilbert degradation method. Reaction products can be viewed concurrent with degradation, or following degradation (i.e., downstream of the reaction). Indeed, one advantage of the present invention over standard Maxam Gilbert methods is that extremely small quantities of reagent can be used. One of skill will appreciate that some of the reagents in the Maxam Gilbert method are highly toxic and/or explosive, making working with large quantities of these reagents (i.e., as in standard methods) somewhat problematic.

Sequencing by Hybridization

Sequencing by hybridization to complementary oligonucleotides has also been developed e.g., in U.S. Pat. No. 5,202,231, to Drmanac et al.; Drmanac et al. (1989) Genomics 4:114-128 and, e.g., Drmanac et al. (1998) "Accurate sequencing by hybridization for DNA diagnostics and individual genomics" Nature Biotechnology 16: 54-58. Methods of detecting genetic differences by hybridization are described e.g., in Fodor (1997) "Genes, Chips and the Human Genome" FASEB Journal. 11:121-121; Fodor (1997) "Massively Parallel Genomics" Science. 277:393-395; Chee et al. (1996) "Accessing Genetic Information with High-Density DNA Arrays" Science 274:610-614, and in a variety of other publications.

The arrays of the present invention are particularly well suited to sequencing and/or detection of differences at the nucleic acid level, by hybridization methods. In particular, either probe or target nucleic acids (or both in multiplexed assays) are fixed to array members. Either probes, or target members, or both, are flowed sequentially, simultaneously or in parallel into contact. Typically, either the probe or target member are labeled to facilitate detection of any hybridization event. Alternatively, nucleic acids can simply be hybridized to and denatured from the array, with detection occurring downstream from the hybridization event (e.g., where the detection and hybridization are timed to provide meaningful information regarding the hybridization). Downstream detection can be performed with a labeled probe (which is optionally a component of the array, or of a second fluidly connected array), or by simple detection of the physical presence of the nucleic acid (e.g., detection downstream can be performed by mass spectroscopy).

It is expected that one of skill is thoroughly familiar with the theory and practice of nucleic acid hybridization and probe selection. Gait, ed. Oligonucleotide Synthesis: A Practical Approach, IRL Press, Oxford (1984); W. H. A. Kuijpers Nucleic Acids Research 18(17), 5197 (1994); K. L. Dueholm J. Org. Chem. 59, 5767-5773 (1994); S. Agrawal (ed.) Methods in Molecular Biology, volume 20; and Tijssen (1993) Laboratory Techniques in biochemistry and molecular biology—hybridization with nucleic acid probes, e.g., part I chapter 2 "overview of principles of hybridization and the strategy of nucleic acid probe assays", Elsevier, New York provide a basic guide to nucleic acid hybridization. Hybridization of nucleic acids to nucleic acids fixed to solid substrates is described, e.g., in U.S. Pat. No. 5,202,231, to Drmanac et al.; Drmanac et al. (1989) Genomics 4:114-128 and, e.g., Drmanac et al. (1998) "Accurate sequencing by hybridization for DNA diagnostics and individual genomics" Nature Biotechnology 16: 54-58. Methods of detecting genetic differences by hybridization are described e.g., in Fodor (1997) "Genes, Chips and the Human Genome" FASEB Journal. 11:121-121; Fodor (1997) "Massively Parallel Genomics" Science. 277:393-395; Chee et al. (1996) "Accessing Genetic Information with High-Density DNA Arrays" Science 274:610-614.

These methods of sequencing and assessing genetic difference are adapted to the arrays of the invention by performing hybridization assays in a microfluidic format. In particular, nucleic acids (e.g. either probes or targets) are fixed to an array member e.g., by covalent synthesis strategies as noted supra (e.g. by light directed synthesis and photomasking procedures), or by hybridization to a molecule which captures the nucleic acid, such as a complementary nucleic acid, or antibody specific for DNA or RNA. In addition to the references noted above regarding nucleic acid hybridization, antibodies to, e.g., DNA, RNA and DNA-RNA duplexes are known, as are immunological methods of screening for (and differentiating between) DNA, RNA and RNA-DNA. For example, Coutlee et al. (1989) Analytical Biochemistry 181: 153-162 describe non-isotopic detection of RNA in an enzyme immunoassay using a monoclonal antibody which binds DNA:RNA hybrids. In these assays, hybridization of an RNA target with a biotinylated DNA probe is performed, followed by incubation of the hybridized target-probe duplex on an anti-biotin plate, reaction of the resulting bound duplex with a beta-galactosidase labeled monoclonal antibody specific for RNA-DNA hybrids, and addition of a fluorescent substrate. In another example, a "sandwich" hybridization method is described for non-isotopic detection of e.g., RNA using oligonucleotides (Ishii & Ghosh (1993) Bioconjugate Chem. 4:34-41). In these assays, the RNA target is hybridized to a first complementary oligonucleotide, which is linked to a bead. The RNA target is then hybridized to a second complementary oligonucleotide conjugated to alkaline phosphatase. The RNA target is detected by providing a chemiluminescent alkaline phosphatase substrate. These methods are readily adapted to the present invention, e.g., by providing arrays of such beads in a microfluidic format, as well as downstream, sequential, or simultaneous detection of the alkaline phosphatase reaction.

For example, in one aspect, targets for sequencing are fixed to particles (for example, unsequenced clones can be fixed to particle sets, or specific fragments of such clones can be fixed to particular particle sets. The particle sets are then flowed into e.g., selected portions of a particle retention region. Small labeled probes (e.g., 6-15 mers, typically 6-12 mers) are then flowed into contact with the fixed targets for sequencing under selected hybridization conditions (typically stringent hybridization conditions), and the arrays are monitored for specific binding by the probes. The probes are then washed free of the targets and the process repeated with at least one additional probe. Specific sequences are generated by compiling the sequences of probes bound to the targets. Examples of devices for storing and accessing large sets of small probes in conjunction with a microfluidic system are described, e.g., in "Closed Loop Biochemical Analyzers" WO 98/45481.

Other investigators have also reported immunological detection of DNA:RNA hybrids, including Bogulayski et al. (1986) J. Immunol. Methods 89:123-130; Prooijen-Knegt (1982) Exp. Cell Res. 141:397-407; Rudkin (1976) Nature 265:472-473, and Stollar (1970) PNAS 65:993-1000. Similarly, detection of DNA:DNA hybrids and RNA:RNA hybrids has also been described. See, Ballard (1982) Mol. Immunol. 19:793-799; Pisetsky and Caster (1982) Mol. Immunol. 19:645-650, and Stollar (1970) PNAS 65:993-1000. These methods are similarly adapted to the present invention by fixing one or more component of the assay to one or more array members, flowing other components of the assay into contact with the one or more array members and detecting any resulting signal.

An alternative sequencing method useful in the present invention, e.g., using particle arrays and microfluidic devices, involves the use of an intercalator. A template is sequenced in the presence of an intercalator, e.g., an intercalating nucleic acid dye. Nucleotides are flowed across the template or the template is flowed across a nucleotide solution as described above. Upon addition of a nucleotide to the primer, the intercalator, e.g., a fluorescent or chemiluminescent intercalator, intercalates into the new double stranded region produced by the addition of a nucleotide to the primer. The intercalator is then detected, e.g., by an increase in signal, i.e., a fluorescent signal. The signal is optionally photobleached after detection, as described above, to decrease the background signal before addition of more nucleotides.

Figure 17:
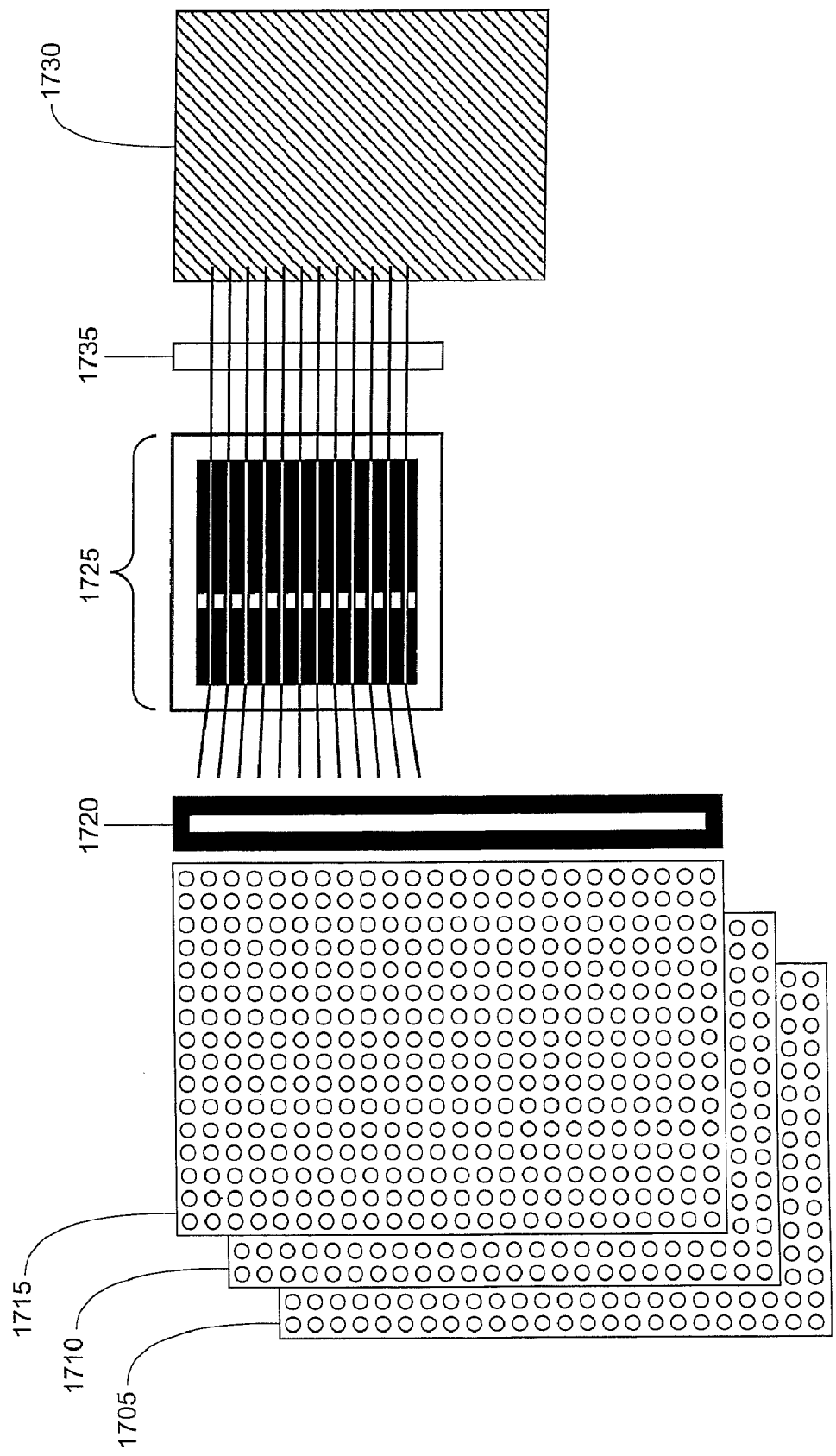
FIG. 17 is a schematic illustrating sequencing by synthesis in a high throughput system.

The above sequencing methods are optionally performed using the microfluidic devices and particle arrays of the invention to provide, e.g., a high throughput system of sequencing. A schematic of such a system is provided in FIG. 17. FIG. 17 shows three 384-well microtiter plates, plates 1705, 1710, and 1715. Each well contains a set of particles comprising a nucleic acid template. Therefore, the system shown optionally comprises 1152 different nucleic acid templates that are optionally sequenced in a high throughput manner. Additional microwell plates and channels are optionally used to provide a greater number of templates. A plate of blank particle sets is also optionally included, e.g., plate 1720. The particle sets are loaded into a set of capillaries or channels as shown by capillary set 1725. For example, 96 particle sets are optionally loaded into each of 12 channels using 12 sipper capillaries or one sipper capillary fluidly coupled to each of the 12 channels. The particle sets are typically retained in the capillary or microchannel by a porous particle retention element, e.g., a sintered glass frit, a set of epoxy coated particles, or the like. Alternative particle retention devices are described above, e.g., narrowed channel dimensions. The particle retention element fixes or retains the particle sets, e.g., particle sets comprising nucleic acid templates, in the channel. The particle sets, e.g., templates, are then optionally exposed to a series or train of reagents. The reagents are typically added through each capillary, e.g., from another set of microwell plates, to perform various assays, e.g., sequencing. A single controller, e.g., controller 1730 is optionally used to control fluid flow through the sipper and channels. One or more detector is used to monitor the particle packets in the channels as various nucleotides are added. Alternatively, detectors are positioned downstream of the channels to monitor the waste products, e.g., to detect a fluorescent label that has since been washed from the channels. For example detection optionally occurs in detection region 1735. Using a system such as that shown in FIG. 17, one particle set is optionally loaded in about one minute. Therefore 96 templates are optionally analyzed, e.g., sequenced, in 1.6 hours. Alternatively, particles with different chemistries are arrayed sequentially in a single capillary and a template is flowed across the array, e.g., for sequencing.

In addition to sequencing by hybridization, essentially similar methods can be used for determination of genetic difference, assays for determining nucleic acid melting points, and the like. Additional details on these procedures are found herein.

PCR

In addition to its applicability to sequencing, PCR is desirably practiced using the arrays of the invention. In particular, PCR templates and/or reagents (e.g., a thermostable polymerase) can be fixed to particles, as described herein and using techniques available in the art. Reagents and/or templates can be passed over arrays, where PCR is performed. This format is especially useful where several PCR products are to be screened simultaneously (or sequentially). A variety of such PCR assays, e.g., for diagnostic applications (e.g., detection of viruses such as HIV, HBV, HCV, etc., detection of infectious organisms (bacteria, parasites, etc.), detection of genetic abnormalities (genetic diseases, cancer, etc.), as well as for research applications (e.g., screening of drugs, drug targets, genes effected in vivo or in vitro by drugs or potential drugs, results of forced evolution methods) as well as many others are well known in the literature and adaptable to the present invention.

Examples of techniques sufficient to direct persons of skill through in vitro amplification methods, including the polymerase chain reaction (PCR) the ligase chain reaction (LCR), Q-replicase amplification and other RNA polymerase mediated techniques (e.g., NASBA) are found in Berger, Sambrook, and Ausubel, as well as Mullis et al., (1987) U.S. Pat. No. 4,683,202; PCR Protocols A Guide to Methods and Applications (Innis et al. eds) Academic Press Inc. San Diego, Calif. (1990) (Innis); Arnheim & Levinson (Oct. 1, 1990) C&EN 36-47; The Journal Of NIH Research (1991) 3, 81-94; (Kwoh et al. (1989) Proc. Natl. Acad. Sci. USA 86, 1173; Guatelli et al. (1990) Proc. Natl. Acad. Sci. USA 87, 1874; Lomell et al. (1989) J. Clin. Chem. 35, 1826; Landegren et al., (1988) Science 241, 1077-1080; Van Brunt (1990) Biotechnology 8, 291-294; Wu and Wallace, (1989) Gene 4, 560; Barringer et al. (1990) Gene 89, 117, and Sooknanan and Malek (1995) Biotechnology 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) Nature 369: 684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

It will be appreciated that these benchtop uses for PCR are adaptable to microfluidic systems. Indeed, PCR amplification is particularly well suited to use in the apparatus, methods and systems of the invention.

Thermocycling amplification methods, including PCR and LCR, are conveniently performed in microscale devices, making iterative fluidic operations involving PCR well suited to use in methods and devices of the present invention (see also, U.S. Pat. Nos. 5,498,392 and 5,587,128 to Willingham et al.).

Thermocycling for PCR and other thermocyclic applications (e.g., the ligase chain reaction, or LCR) can be conducted in microfluidic systems in at least two ways. First, a heat source (external or internal) can be used to thermocycle all or part of a device, thereby heating and cooling the array within the microfluidic system. In a second approach, joule heating is used. Thermocycling in microscale devices, e.g., using joule heating, is described in co-pending application Ser. No. 08/977,528, filed Nov. 25, 1997 (now U.S. Pat. No. 5,965,410). In brief, energy is provided to heat fluids, e.g., samples, analytes, buffers and reagents, in desired locations of the substrates in an efficient manner by application of electric current to fluids in microchannels. Thus, the present invention optionally uses power sources that pass electrical current through the fluid in a channel for heating purposes, as well as for material transport. In exemplary embodiments, the fluid passes through a channel of a desired cross-section (e.g., diameter) to enhance thermal transfer of energy from the current to the fluid. The channels can be formed on almost any type of substrate material such as, for example, amorphous materials (e.g., glass, plastic, silicon), composites, multi-layered materials, combinations thereof, and the like. In general, electric current passing through the fluid in a channel produces heat by dissipating energy through the electrical resistance of the fluid. Power dissipates as the current passes through the fluid and goes into the fluid as energy as a function of time to heat the fluid. The following mathematical expression generally describes a relationship between power, electrical current, and fluid resistance, i.e., POWER=$I^2$R where POWER=power dissipated in fluid; I=electric current passing through fluid; and R=electric resistance of fluid.

The above equation provides a relationship between power dissipated ("POWER") to current ("I") and resistance ("R"). In some of the embodiments, which are directed toward moving fluid in channels, e.g., to provide mixing, electrophoretic separation, or the like, a portion of the power goes into kinetic energy of moving the fluid through the channel. However, it is also possible to use a selected portion of the power to controllably heat fluid in a channel or selected channel regions. A channel region suitable for heating is often narrower or smaller in cross-section than other channel regions in the channel structure, as a smaller cross-section provides higher resistance in the fluid, which increases the temperature of the fluid as electric current passes through. Alternatively, the electric current is increased across the length of the channel by increased voltage, which also increases the amount of power dissipated into the fluid to correspondingly increase fluid temperature.

The introduction of electrical current into fluid causes heat (Joule heating). In the examples of fluid movement herein where thermal effects are not desired, the heating effect is minimal because, at the small currents employed, heat is rapidly dissipated into the chip itself. By substantially increasing the current across the channel, rapid temperature changes are induced that can be monitored by conductivity. At the same time, the fluid can be kept static in the channel by using alternating instead of direct current. Because nanoliter volumes of fluid have tiny thermal mass, transitions between temperatures can be extremely short. Oscillations between any two temperatures above 0° C. and below 100° C. in 100 milliseconds have been performed. Additional applications of joule heating to sequencing methodologies is set forth in "Closed Loop Biochemical Analyzers" (WO 98/45481).

Melting Point Analysis of Nucleic Acids

In an embodiment similar to sequencing by hybridization, the systems, devices arrays and methods of the present invention can be used to detect variations in nucleic acid sequences by determining the strength of the hybridization between the targeted nucleic acid and probes that are putative perfect complements to the target. By identifying the difference in stability between the imperfect and perfect hybrids under conditions of increasing hydrogen bond stress, one can identify those nucleic acids that contain a variation.

In practice, a microfluidic device is configured to accept a sample containing an amplified nucleic acid or polynucleotide sequence of interest, convert it to single-stranded form, facilitate hybridization with a nucleic acid probe, such as an oligonucleotide, and then subject the hybridization mixture to a chemical or temperature gradient that distinguishes between perfectly matched targets and those that differ by at least one base pair (mismatch). Either the probe or the template can be fixed to an array component. In some embodiments, one or more loci or targeted areas of the sample polynucleotide are first amplified by techniques such as PCR or sandwich hybridization. In other embodiments, unamplified polynucleotide is provided to the device and amplified therein.

Hybridization of the probe results in a perfect hybrid with no mismatches when the sample polynucleotide contains the complementary sequence, i.e., no variation, or in a hybrid with mismatches if the sample polynucleotide differs from the probe, i.e., contains a sequence variation. The stability of the imperfect hybrid differs from the perfect hybrid under conditions of increasing hydrogen bond stress. A variety of methods are available for subjecting the hybrids to increasing hydrogen bond stress, sufficient to distinguish between perfectly matched probe/target hybrids and imperfect matches. For example, the hybrids are optionally subjected to a temperature gradient, or alternatively, can be subjected to increasing concentrations of a chemical denaturant, e.g., formamide, urea, and the like, or increasing pH. By monitoring hybridization between one or more array component and one or more unknown nucleic acid, it is possible to determine percent sequence complementarity.

The assay is optionally repeated several times, varying the concentration of denaturant or temperature with each successive assay. By monitoring the level of hybridization, one can determine the concentration of denaturant at which the probe-target hybrid is denatured. This level is then compared to a standard curve, to determine whether one or more variations are present in the nucleic acid.

Other Sequencing Strategies

Other sequencing methods which reduce the number of steps necessary for template preparation and primer selection have been developed. One proposed variation on sequencing technology involves the use of modular primers for use in PCR and DNA sequencing. For example, Ulanovsky and co-workers have described the mechanism of the modular primer effect (Beskin et al. (1995) Nucleic Acids Research 23(15):2881-2885) in which short primers of 5-6 nucleotides can specifically prime a template-dependent polymerase enzyme for template dependent nucleic acid synthesis. A modified version of the use of the modular primer strategy, in which small nucleotide primers are specifically elongated for use in PCR to amplify and sequence template nucleic acids has also been described. The procedure is referred to as DNA sequencing using differential extension with nucleotide subsets (DENS). See, Raja et al. (1997) Nucleic Acids Research 25(4):800-805. These modular primer strategies, for sequencing or PCR, are readily adapted to the present methods and arrays. For example, template or primer nucleic acids can be fixed, directly or indirectly, to the array members of the present invention. The corresponding template or primer is flowed into contact with the array member, along with any other components of the sequencing or PCR reaction (or other reaction, if appropriate) and the reaction performed under appropriate conditions to the reaction. Products are detected e.g., by washing the products from the array and detecting the products at a downstream detector.

Liquid Crystal Assay Systems

In still another embodiment, binding of a protein to a target component such as a nucleic acid can be detected by the use of liquid crystals. Liquid crystals have been used, for example, to amplify and transduce receptor-mediated binding of proteins at surfaces into optical outputs. Spontaneously organized surfaces can be designed so that a protein, upon binding to a nucleic acid hosted on the surface of an array member herein, triggers changes in the orientations of 1- to 20-micrometer-thick films of supported liquid crystals, thus corresponding to a reorientation of ~$10^5$ to $10^6$ mesogens per protein. Binding-induced changes in the intensity of light transmitted through the liquid crystal are easily seen with the naked eye and can be further amplified by using surfaces designed so that protein-nucleic acid binding causes twisted nematic liquid crystals to untwist (see, e.g., Gupta et al. (1998) Science, 279: 2077-2080). This approach to the detection of protein/nucleic acid interactions does not require labeling of the analyte, does not require the use of electroanalytical apparatus, provides a spatial resolution of micrometers, and is sufficiently simple that it is useful in biochemical assays and imaging of spatially resolved chemical libraries.

Diagnostic/Screening Assays

In one aspect of the present invention, diagnostic assays are provided. As discussed supra, assays can take the form of nucleic acid detection or sequencing assays which screen for the presence or absence or type of a nucleic acid. The presence or type of a nucleic acid in a biological sample is an indicator for the presence of, e.g., an infectious organism (e.g., virus, bacteria, fungal cell or the like) in the biological sample. Thus, detection of a nucleic acid provides an indication that, e.g., a patient is infected with such an infectious organism.

Similarly, the presence of certain mRNAs (e.g., mRNAs from oncogene products) and/or specific sequences in genomic DNA are correlated with a variety of disease states, including, e.g., cancer. Thus, any of the various assay formats described herein can be used for the detection of specific nucleic acids which correspond to particular disease states. Many such correlations are well established in the art.

Microfluidic devices are very efficient at capturing molecules in a fluid stream, e.g., in functionalized channels, or on particle sets within the channels. After capturing a particular molecule, e.g., a sample that is present only in small concentrations, the devices are used to detect the molecule, e.g., its presence or type. For example, a number of nucleic acids or cells are optionally flowed through a microfluidic device for capture, e.g., by a set of particles. Reagents that bind to a molecule of interest, e.g., by hybridization, are optionally flowed across the captured molecules and a molecule of interest is identified, e.g., by its binding specificity. This is especially useful when samples of low concentration are captured because the sample is optionally positioned in a defined location for further analysis or detection, e.g., by specific binding moieties.

In addition to screening for diseases, the arrays of the invention can also be used to select for the presence of desirable traits. For example, in agriculture, many correlations between desirable traits and particular genomic or RNA sequences are well established. For example, crops such as corn, soybean, cotton, potatoes, tomatoes, wheat, millet, and many others are routinely selected, in part, by selecting for the presence or absence of nucleic acids which are correlated with desirable traits such as yield, disease resistance, herbicide resistance, drought tolerance and the like.

Expression Profiling

One particularly useful aspect of array technology is the ability to profile expression of one or more expression products for one or more biological sample. By profiling expression of RNAs and/or proteins, it is possible to determine whether certain disease-related genes (e.g., oncogenes, infectious organisms, or the like) are expressed. In addition, it is possible to use expression profiles to determine combinatorial genetic and polygenetic effects on expression and to predict phenotypes resulting from polygenetic effects. For example, where expression of several genes causes a phenotype, it is possible to monitor expression of these genes on the arrays of the invention. For example, polygenic effects often underlie disease or herbicide resistance in plants, pesticide resistance in insects, and disease states in animals (including humans).

A variety of sources of biological material can be profiled, including animal sources (including human, vertebrate, mammalian, insect, etc.) and plant sources (e.g., wild or domesticated plants, such as crop plants). The biological sources can be from tissues, cells, whole organisms, cell cultures, tissue cultures, or the like. A variety of profiling methods are adaptable to the present system, including hybridization of expressed or amplified nucleic acids to a nucleic acid array, hybridization of expressed polypeptides to a protein array, hybridization of peptides or nucleic acids to an antibody array, subtractive hybridization, differential display and others.

In one preferred embodiment, the expression products which are detected in the methods of the invention are RNAs, e.g., mRNAs expressed from genes within a cell derived from the biological source to be profiled. A number of techniques are available for detecting RNAs, which can be utilized or adapted to the arrays of the invention. For example, northern blot hybridization is widely used for RNA detection, and is generally taught in a variety of standard texts on molecular biology, including: Berger and Kimmel, Sambrook, Ausubel (all supra), etc. Furthermore, one of skill will appreciate that essentially any RNA can be converted into a double stranded DNA using a reverse transcriptase enzyme and a polymerase. See, Ausubel, Sambrook and Berger, id. Thus, detection of mRNAs can be performed by converting, e.g., mRNAs into DNAs, which are subsequently detected in, e.g., a "Southern blot" format.

Furthermore, DNAs can be amplified to aid in the detection of rare molecules by any of a number of well known techniques, including: the polymerase chain reaction (PCR), the ligase chain reaction (LCR), Q-replicase amplification and other RNA polymerase mediated techniques (e.g., NASBA). Examples of these techniques are found in Berger, Sambrook, and Ausubel, id., as well as in those references noted supra regarding in vitro amplification. These amplification steps can be performed in the microfluidic system, or external to the microfluidic system.

Probes can be fixed to array members to create a probe array, and expression products (or in vitro amplified nucleic acids corresponding to expression products) can be labeled and hybridized with the array. For convenience, it may be helpful to use several arrays simultaneously (e.g., in the same or in separate microfluidic devices), or to use arrays of large or small numbers of members, depending on the number of expression products to be detected.

It will be appreciated that probe design is influenced by the intended application. For example, where several allele-specific probe-target interactions are to be detected in a single assay, e.g., on a single array, it can be desirable to have similar melting temperatures for all of the probes (or course this is not necessary, as joule or zone heating can be used to maintain different portions of an array at different temperatures). Accordingly, the length of the probes are optionally adjusted so that the melting temperatures for all of the probes on the array are closely similar (it will be appreciated that different lengths for different probes may be needed to achieve a particular $T_m$ where different probes have different GC contents). Although melting temperature is a primary consideration in probe design, other factors are also optionally used to further adjust probe construction, such as elimination of self-complementarity in the probe (which can inhibit hybridization of a target nucleotide).

One way to compare expression products between two cell populations is to identify mRNA species which are differentially expressed between the cell populations (i.e., present at different abundances between the cell populations). In addition to the techniques noted above, another preferred method is to use subtractive hybridization (Lee et al. (1991) Proc. Natl. Acad. Sci. (U.S.A.) 88:2825) or differential display employing arbitrary primer polymerase chain reaction (PCR) (Liang and Pardee (1992) Science 257:967). Each of these methods has been used by various investigators to identify differentially expressed mRNA species. See, Salesiotis et al. (1995) Cancer Lett. 91:47; Jiang et al. (1995) Oncogene 10:1855; Blok et al. (1995) Prostate 26:213; Shinoura et al. (1995) Cancer Lett. 89:215; Murphy et al. (1993) Cell Growth Differ 4:715; Austruy et al. (1993) Cancer Res. 53:2888; Zhang et al. (1993) Mol. Carcinog. 8:123; and Liang et al. (1992) Cancer Res. 52:6966). The methods have also been used to identify mRNA species which are induced or repressed, e.g., by drugs or certain nutrients (Fisicaro et al. (1995) Mol. Immunol. 32:565; Chapman et al. (1995) Mol. Cell. Endocrinol. 108:108; Douglass et al. (1995) J. Neurosci. 15:2471; Aiello et al. (1994) Proc. Natl. Acad. Sci. (U.S.A.) 91:6231; Ace et al. (1994) Endocrinology 134:1305.

For the technique of differential display, Liang and Pardee (1992), supra provide theoretical calculations for the selection of 5' and 3' arbitrary primers. Correlation of observed results to the theory is also provided. In practice, 5' primers of less than about 9 nucleotides may not provide adequate specificity (slightly shorter primers of about 8 to 10 nucleotides have been used in PCR methods for analysis of DNA polymorphisms. See also, Williams et al. (1991) Nucleic Acids Research 18, 6531). The primer(s) optionally comprise 5'-terminal sequences which serve to anchor other PCR primers (distal primers) and/or which comprise a restriction site or half-site or other ligatable end. Where a restriction site or amplification template for a second primer is incorporated, the primers are optionally longer than those described above by the length of the restriction site, or amplification template site. Standard restriction enzyme sites include 4 base sites, 5 base sites, 6 base sites, 7 base sites, and 8 base sites. An amplification template site for a second primer can be of essentially any length, for example, the site can be about 15-25 nucleotides in length. Any of primers, templates, or other reactants (e.g., enzymes) can be fixed to array particle members.

The amplified products are optionally labeled and are typically resolved e.g., by electrophoresis on a polyacrylamide gel or other sieving matrix in the microfluidic system; the location(s) where label is present are recovered from the sieving matrix, typically by elution or electrokinetic methods. The resultant recovered product species can be subcloned into a replicable vector with or without attachment of linkers, amplified further, and/or detected, or even sequenced directly. As noted, direct sequencing of PCR generated amplicons by selectively incorporating boronated nuclease resistant nucleotides into the amplicons during PCR and digestion of the amplicons with a nuclease to produce sized template fragments has been performed (Porter et al. (1997) Nucleic Acids Research 25(8):1611-1617) and is applicable to the present invention.

It is expected that one of skill can use, e.g., differential display for expression profiling. In addition, companies such as CuraGen Corp. (New Haven Conn.) provide robust expression profiling based upon differential display techniques. See, e.g., WO 97/15690 by Rothenberg et al., and these methods are readily adapted to a microfluidic format.

Expression Profiling of Proteins

In addition to nucleic acid formats, the arrays of the invention can easily be adapted to screening other biological components as well, including cells, antibodies, antibody ligands and the like. The presence or absence of such cells, antibodies and antibody ligands are also known to correlate with desirable or undesirable features. For example, one common assay for the detection of infectious organisms involves an ELISA assay or western blot to detect the presence of antibodies in a patient to a particular infectious agent (e.g., an HIV virus). Such immunological assays are also adaptable to the arrays of the present invention, e.g., by fixing an antibody or antibody target to an array member and exposing the array member to the corresponding antibody or antibody target. Thus, immunological reagents (i.e., those used in an assay in which an antibody is a target or reagent) can be flowed across the arrays of the invention.

In addition to profiling RNAs (or corresponding cDNAs) as described above, it is also possible to profile proteins. In particular, various strategies are available for detecting many proteins simultaneously. As applied to the present invention, detected proteins, corresponding to expression products, can be derived from one of at least two sources. First, the proteins which are detected can be either directly isolated from a cell or tissue to be profiled, providing direct detection (and, optionally, quantification) of proteins present in a cell. Second, mRNAs can be translated into cDNA sequences, cloned and expressed. This increases the ability to detect rare RNAs, and makes it possible to immediately associate a detected protein with its coding sequence. For purposes of the present invention, even an out of frame peptide is an indicator for the presence of a corresponding RNA.

A variety of hybridization techniques, including western blotting, ELISA assays, and the like are available for detection of specific proteins. See, Ausubel, Sambrook and Berger, supra. See also, Antibodies: A Laboratory Manual, (1988) E. Harlow and D. Lane, Cold Spring Harbor Laboratory, Cold Spring Harbor, N.Y. Non-hybridization based techniques such as two-dimensional electrophoresis can also be used to simultaneously and specifically detect large numbers of proteins. Either antibody or two dimensional gel electrophoresis can readily be adapted to microfluidic systems.

One typical technology for detecting specific proteins involves making antibodies to the proteins. By specifically detecting binding of an antibody and a given protein, the presence of the protein can be detected. In addition to available antibodies, one of skill can easily make antibodies using existing techniques, or modify those antibodies which are commercially or publicly available. In addition to the art referenced above, general methods of producing polyclonal and monoclonal antibodies are known to those of skill in the art. See, e.g., Paul (ed.) (1993) Fundamental Immunology, Third Edition Raven Press, Ltd., New York Coligan (1991) Current Protocols in Immunology Wiley/Greene, N.Y.; Harlow and Lane (1989) Antibodies: A Laboratory Manual Cold Spring Harbor Press, NY; Stites et al. (eds.) Basic and Clinical Immunology (4th ed.) Lange Medical Publications, Los Altos, Calif., and references cited therein; Goding (1986) Monoclonal Antibodies: Principles and Practice (2d ed.) Academic Press, New York, N.Y.; and Kohler and Milstein (1975) Nature 256:495-497. Other suitable techniques for antibody preparation include selection of libraries of recombinant antibodies in phage or similar vectors. See, Huse et al. (1989) Science 246:1275-1281; and Ward et al. (1989) Nature 341:544-546. Specific monoclonal and polyclonal antibodies and antisera will usually bind with a KD of at least about 0.1 µM, preferably at least about 0.01 µM or better, and most typically and preferably, 0.001 µM or better. As used herein, an "antibody" refers to a protein consisting of one or more polypeptide substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH—CH1 by a disulfide bond. The F(ab)'2 may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies include single chain antibodies, including single chain Fv (sFv) antibodies in which a variable heavy and a variable light chain are joined together (directly or through a peptide linker) to form a continuous polypeptide.

For purposes of the present invention, antibodies or antibody fragments can be arrayed, e.g., by coupling to an amine moiety fixed to a solid phase particle array member, in a manner similar to that described above for construction of nucleic acid arrays. As above for nucleic acid probes, the antibodies can be labeled, or proteins corresponding to expression products can be labeled. In this manner, it is possible to couple hundreds, or even thousands, of different antibodies to members of an array. In one embodiment, a bacteriophage antibody display library is screened with a polypeptide encoded by a cell, or obtained by expression of mRNAs, differential display, subtractive hybridization or the like. Combinatorial libraries of antibodies have been generated in bacteriophage lambda expression systems which are screened as bacteriophage plaques or as colonies of lysogens (Huse et al. (1989) Science 246:1275; Caton and Koprowski (1990) Proc. Natl. Acad. Sci. (U.S.A.) 87:6450; Mullinax et al (1990) Proc. Natl. Acad. Sci. (U.S.A.) 87:8095; Persson et al. (1991) Proc. Natl. Acad. Sci. (U.S.A.) 88:2432). Various embodiments of bacteriophage antibody display libraries and lambda phage expression libraries have been described (Kang et al. (1991) Proc. Natl. Acad. Sci. (U.S.A.) 88:4363; Clackson et al. (1991) Nature 352:624; McCafferty et al. (1990) Nature 348:552; Burton et al. (1991) Proc. Natl. Acad. Sci. (U.S.A.) 88:10134; Hoogenboom et al. (1991) Nucleic Acids Res. 19:4133; Chang et al. (1991) J. Immunol. 147:3610; Breitling et al. (1991) Gene 104:147; Marks et al. (1991) J. Mol. Biol. 222:581; Barbas et al. (1992) Proc. Natl. Acad. Sci. (U.S.A.) 89:4457; Hawkins and Winter (1992) J. Immunol. 22:867; Marks et al. (1992) Biotechnology 10:779; Marks et al. (1992) J. Biol. Chem. 267:16007; Lowman et al (1991) Biochemistry 30:10832; Lerner et al. (1992) Science 258:1313.

The patterns of hybridization which are detected on the array provide an indication of the presence or absence of expressed protein sequences. As long as the library or array against which a population of proteins are to be screened can be correlated from one experiment to the next (e.g., by noting the x-y coordinates of the library or array member, or by noting the position of markers within the arrays (e.g., where the arrays comprise mobile members)), no sequence information is required to compare expression profiles from one representative sample to another. In particular, the mere presence or absence (or degree) of label provides the ability to determine differences. One advantage of using arrayed libraries of antibodies for protein detection is that the individual library members can be uncharacterized.

More generally, peptide and nucleic acid hybridization to arrays or libraries (or even simple two dimensional gels) can be treated in a manner analogous to a bar code label. Any diverse library or array can be used to screen for the presence or absence of complementary molecules, whether RNA, DNA, protein, or a combination thereof. By measuring corresponding signal information between different sources of test material (e.g., different hybrid or inbred plants, or different tissues, or the like), it is possible to determine differences in expression products for the different source materials. As set forth below, this process is facilitated by various high throughput integrated systems set forth below.

In addition to array based approaches, mass spectrometry is in use for identification of large sets of proteins in samples, and is suitable for identification of many proteins in a sequential or parallel fashion. For example, Hutchens et al. U.S. Pat. No. 5,719,060, describe methods and apparatus for desorption and ionization of analytes for subsequent analysis by mass spectroscopy and/or biosensors. In the present invention, components can be released from array members in a sequential fashion and prepared for mass spectrometry.

Two and three dimensional gel based approaches can also be used for the specific and simultaneous identification and quantification of large numbers of proteins from biological samples. Multi-dimensional gel technology is well-known and described e.g., in Ausubel, supra, Volume 2, Chapter 10. As applied to microfluidic systems, intersecting channels can comprise different separation media. After flowing components through a first media, components can be flowed through a second media in a second channel. The components can be labeled, e.g., by flowing staining reagents into contact with the components. The labeled components are then flowed past a suitable detector (or the entire microfluidic system can be imaged simultaneously, e.g., using a CCD array). Image analysis of multi-dimensional protein separation channels provides an indication of the proteins that are expressed e.g., in a cell or tissue type.

In addition to identifying expression products, such as proteins or RNA, it is also possible to screen for large numbers of metabolites in cell or tissue samples. The presence, absence or level of a metabolite can be treated as a character for comparison purposes in the same way that nucleic acids or proteins are discussed herein. Metabolites can be monitored by any of currently available microfluidic method, including chromatography, uni or multi dimensional gel separations, hybridization to complementary molecules, or the like.

Immunoassays

A particular protein or other biological component can be quantified by a variety of immunoassay methods which can be practiced using the arrays of the invention. For a review of immunological and immunoassay procedures in general, see Stites and Terr (eds.) 1991 *Basic and Clinical Immunology* (7th ed.); Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, NY; Ngo (ed.) (1988) *Non isotopic Immunoassays* Plenum Press, NY and Fundamental Immunology, *Third Edition*, W. E. Paul, ed., Raven Press, N.Y. (1993).

Immunoassays often utilize a labeling agent to specifically bind to and label the binding complex formed by the capture agent and the analyte. The labeling agent may itself be one of the moieties comprising the antibody/analyte complex. Thus, the labeling agent may be a labeled analyte or a labeled anti-analyte antibody. Alternatively, the labeling agent may be a third moiety, such as another antibody, that specifically binds to the antibody/analyte complex, or to a modified capture group (e.g., biotin) which is covalently linked to the analyte or anti-analyte antibody. Any of these components can be e.g., fixed to array members or can be present in reagent trains which are flowed across array members.

In one embodiment, the labeling agent is an antibody that specifically binds to a capture agent (e.g., an antibody which binds either the analyte, an analyte-antibody complex or an antibody which binds the analyte). Such labeling agents are well known to those of skill in the art, and most typically comprise labeled antibodies that specifically bind antibodies of the particular animal species from which the capture agent is derived (e.g., an anti-idiotypic antibody). Thus, for example, where the capture agent is a mouse derived antimarker gene antibody, the label agent may be a goat anti-mouse IgG, i.e., an antibody specific to the constant region of the mouse antibody. Other proteins capable of specifically binding immunoglobulin constant regions, such as streptococcal protein A or protein G are also used as the labeling agent. These proteins are normal constituents of the cell walls of streptococcal bacteria. They exhibit a strong non immunogenic reactivity with immunoglobulin constant regions from a variety of species. See, generally Kronval, et al., (1973) *J. Immunol.*, 111:1401-1406, and Akerstrom, et al., (1985) *J. Immunol.*, 135:2589-2542.

Throughout the assays, incubation and/or washing steps may be required after each combination of reagents. Incubation steps can vary from about 0.5 seconds to several hours. However, the incubation time will depend upon the assay format, analyte, volume of solution, concentrations, and the like. One advantage of the present invention is that incubation times can ordinarily be short, because, in microfluidic systems, small fluid volumes are ordinarily used. Usually, the assays are carried out at ambient temperature, although they can be conducted over a range of temperatures, such as 5 C to 45 C.

(i) Non Competitive Assay Formats

Immunoassays for detecting an analyte can be, e.g., competitive or noncompetitive. Noncompetitive immunoassays are assays in which the amount of captured analyte is directly measured. In a "sandwich" assay, for example, the capture agent (e.g., an antibody) is bound directly to an array member where it is fixed or immobilized. These immobilized antibodies then capture analytes present in a test sample. The analytes which are immobilized are optionally bound by a labeling agent, such as a second antibody bearing a label. Alternatively, the second marker gene antibody may lack a label, but it may, in turn, be bound by a labeled third antibody specific to antibodies of the species from which the second antibody is derived. In another format, a sandwich assay is unnecessary because either the antibody or analyte are labeled, with the complementary component typically being fixed to an array member.

Sandwich assays for an analyte are optionally constructed. As described above, the antibody or antibody ligand bound to an array member specifically binds to the corresponding element present in a sample. A labeled antibody then binds to analyte-antibody complexes. Free labeled antibody is washed away, e.g., by electrophoresis, electroosmosis, electrokinesis or pressure based fluid movement and the remaining bound labeled complex is detected (e.g., using a gamma detector where the label is radioactive, or an optical arrangement where the label is fluorescent or luminescent).

(ii) Competitive Assay Formats

In competitive assays, the amount of analyte present in the sample is measured indirectly by measuring the amount of an added (exogenous) analyte displaced (or competed away) from a capture agent by the analyte present in the sample. In one competitive assay, a known amount of analyte is added to the sample and the sample is contacted with a capture agent, in this case an antibody that specifically binds the analyte. The amount of analyte bound to the antibody is inversely proportional to the concentration of analyte present in the sample.

In one embodiment, the capture agent is immobilized on a solid substrate. The amount of e.g., polypeptide bound to the capture agent is determined either by measuring the amount of analyte present in an analyte-antibody complex, or alternatively by measuring the amount of remaining uncomplexed analyte or antibody. The amount of material in a sample to be assayed can also be detected by providing exogenous labeled marker gene to the assay.

A hapten inhibition assay is another preferred competitive assay. In this assay, a known analyte is fixed on an array member. A known amount of antibody is added to the sample, and the sample is then contacted with the fixed analyte. In this case, the amount of antibody bound to the fixed analyte is proportional to the amount of analyte in the sample. Again the amount of immobilized antibody is detected by quantitating either the immobilized fraction of antibody or the fraction of the antibody that remains in solution. Detection may be direct where the antibody is labeled, or indirect where a labeled moiety is subsequently added which specifically binds to the antibody as described above.

Many other immunoassay formats are known and can be practiced by fixing one or more component of the assay to an array member in a microfluidic array of the invention, e.g., using the coupling techniques described supra.

Downstream Separations

For all of the sequencing and PCR methods noted above, as well as for many other methods noted herein, products can be electrophoresed, e.g., following release from an array, e.g., to facilitate separation and detection of the products. microfluidic systems which combine fluid handling and electrophoresis are described, e.g., in U.S. Ser. No. 09/093,832 (now U.S. Pat. No. 6,306,590) "MICROFLUDIIC MATRIX LOCALIZATION APPARATUS AND METHODS" Burd Mehta and Kopf-Sill filed Jun. 8, 1998. In brief, this application, which describes, e.g., anaphasic and especially multiphasic microfluidic systems, a channel comprising a liquid phase intersects a channel comprising a sieving matrix. Applied to the present invention, products are optionally washed from arrays, where they are flowed into contact with a sieving matrix. The product components typically "stack" at the fluid-sieving matrix interface, and are then electrophoresed through the sieving matrix. The products can then be detected during or after electrophoresis, e.g., by placing a detection element within or proximal to the sieving matrix. The products can also be purified in the sieving matrix and electrokinetically (or by pressure mechanisms) moved into contact with subsequent reactants or additional array members for further processing or for use as reactants in subsequent reactions (e.g., as templates in sequencing reactions, as targets for amplification, as probes to detect amplified products or other targets, etc.).

In uniphasic separatory systems, array components are optionally dispersed within a sieving matrix. Reactions such as sequencing, PCR, LCR, or the like can be conducted on or proximal to the array members, with products being released into the sieving matrix for separation.

In addition to the multiphasic and uniphasic microfluidic systems of the '832 application, a variety of microfluidic electrophoretic applications are described, e.g., in "Closed Loop Biochemical Analyzers" (WO 98/45481), as well as other references available in the art.

Type Switchable Arrays

In one aspect, the arrays are particle type switchable. In this embodiment, arrays are modified by flowing reagents across all, or a portion of the particle sets of the arrays. The reagents chemically interact with (e.g., covalently modify, hybridize to, or the like) particle sets of the array, thereby altering one or more sets of the array. Thus, particle sets can be fixed in place (or flowable) and switchable from one type of particle set to another. For example, in one aspect, the ordered array of a plurality of sets of particles is produced by flowing a substantially homogeneous or heterogeneous set of particles into a particle modification region and flowing a plurality of particle modification reagents across the substantially homogeneous or heterogeneous set of particles. The reagents react with the substantially homogeneous or heterogeneous set of particles to create a plurality of sets of different particles. For example, the homogeneous or heterogeneous sets of particles optionally include a plurality of particles which have one or more molecular tags (e.g., streptavidin, avidin, biotin, an antibody, an antibody ligand, a nucleic acid, a nucleic acid binding molecule, etc.). The plurality of particle modification reagents can include one or more anti-tag ligand. The plurality of particle modification reagents can be flowed sequentially across the substantially homogeneous set of particles, thereby binding the anti-tag ligand to the tag and producing sets of different particles, each set having a different bound particle modification reagent such as a nucleic acid. Tags and tag ligands can be attached to particles or particle modification reagents directly or through a linker, through covalent or non-covalent interactions.

The ability to switch the type of a particle member of an array provides an elegant method for making arrays within microfluidic systems. In particular, arrays are made in situ by exposure to reagents, avoiding the necessity of moving and tracking different particle sets to different array locations.

Moreover, particle type switchability provides for the creation of microfluidic logic circuits. In particular, the presence or absence of a signal from an array location is equivalent to a bit of information in a typical computer system and it is possible to reprogram the array simply by flowing appropriate reagents to appropriate array positions. It should be appreciated that, in at least one sense, these switchable arrays are superior to existing silicon-based computer design. In particular, rather than being limited to a simple digital "on/off" binary programming language, it is possible to obtain analogue information from the arrays. This is because degrees of signal intensity from array locations can be discerned. Thus, a very rich non-binary programming language can be used in programming and interpreting switchable microfluidic arrays. Of course, switchable arrays can incorporate both ordinary binary silicon-based switches, as well as microfluidic switches, providing for design heuristics that incorporate both binary and non-binary programming.

In addition to the creation of logic circuits and array construction, type-switchable arrays can be used as chemical synthesis and purification machines. In particular, array members can have chemical components synthesized in a solid phase fashion on the array members, and subsequently used to purify complementary molecules in a manner similar to affinity chromatography. Alternatively, following synthesis, chemical moieties can be cleaved from the array for subsequent use in other microfluidic assays (or even for purification and use outside of the microfluidic system). This ability to act as a biochemical reactor is a preferred aspect of the present invention.

Reagent Caging and Triggering

The present invention provides for reagent triggering upon contact with an array member. For example, certain reagents are activated by heat or cold, or are activated by changes in pH, light levels, or the like. These reagents can be maintained in an inactive state and activated when they are brought into contact with an array member. Similarly, array members can be maintained in an inactive state and activated by exposure to a temperature change, a change in pH, light, or the like.

Similarly, reagents can be trapped or "caged" by being complexed to a particle and released or "uncaged" from the particle by exposure to an activating reagent or reaction condition. Using these approaches, reagents can be delivered in trapped or inactive packets to a reaction site where they are released and/or activated.

For example, a sequencing reagent such as a nucleic acid template can be fixed to a particle, e.g., by synthesizing or fixing a single-stranded oligonucleotide on the surface of the particle and hybridizing a complimentary nucleic acid to the fixed single stranded nucleic acid. The complimentary nucleic acid can be released by exposure to, e.g., heat, or exposure to a base (e.g., dilute NaOH), or exposure to a denaturant (e.g., guanidine HCL). For example, the particle is optionally flowed to a point where a sequencing reaction is to be performed, and the complimentary strand then released by heat or exposure to base or a denaturant. Alternatively, a sequencing reaction, e.g., by PCR exonuclease digestion, is performed on one or more DNA template attached to a particle, which particle is fixed in the channel, e.g., by a particle retention element, by another set of particles, or the like. The DNA is then optionally released after sequencing for separation or further manipulation. Similarly, proteins can be associated (e.g., by bonding to fixed ligands or antibodies) and released (e.g., by exposure to heat or a base or a denaturant) from the particle. Other molecules such as polymers or large organic molecules can similarly be caged and released from particle members.

Similarly, reagents such as enzymes (e.g., thermostable enzymes), sequencing reagents, or other molecules can be held in an inactive form (e.g., due to heat or presence of blocking groups on the molecules, e.g., those set forth in Greene, et al. (1991) Protective Groups In Organic Chemistry, 2nd Ed., John Wiley & Sons, New York, N.Y.) and flowed into contact with array members. The reagents or other molecules can then be activated, e.g., by exposure to light, changes in temperature, exposure to an acid, base, or a denaturant, or the like. Thus, in one embodiment, reagents are held in a reagent train in an inactive state and are activated only upon exposure to an appropriate activation agent (heat, light, base, acid, denaturant, electric or magnetic field, etc.).

Modulation of Hydrodynamic Resistance with Particle Sets; Iterative Fluid Manipulations The hydrodynamic resistance in a channel can be increased by packing the channel with particles. In addition, electroosmotic flow can be altered significantly by packing the capillary with particles having different surface charges and thus different zeta potential. In one aspect of the present invention, particle manipulation in channels can be used to dynamically control the resistance to pressure or electrokinetic flow to enhance the flexibility of microfluidic operations.

In particular, microbeads or other particles are transported into microchannels by any of the flow methods described herein. The particles are captured (by a physical barrier, electric field, magnetic field, porous matrix, sintered glass frit, a fixed set of particles, etc., as also described supra). By localizing particles to a selected location, it is possible to alter the local zeta potential, surface charge, etc. This, in turn alters flow characteristics in the region, providing for alterations in microfluidic operations, e.g., changes in the rate, or even direction, of fluid flow. Thus, in addition to interacting with components of various reactions, particle sets can also be used to modulate fluid flow in a selected region.

Similarly, a powerful application of this dynamic microfluidic control is to create a "smart" microfluidic system. Applications which use particles in assays are described herein. The combination of flow modulation by microbead localization and e.g., chemical assays on the beads provides for a great deal of flexibility in designing and controlling assays. In addition, with appropriate software feedback control, subsequent assay steps are selectable based upon the results of initial assays. This ability to reconfigure flow conditions and assay components by manipulating particles in response to assay results is a very potent new way of performing iterative reactions.

For example, the integrated assay and flow control features provide very high throughput methods of assessing biochemical components and performing biochemical manipulations. A wide variety of reagents and products are suitably assessed, including libraries of chemical or biological compounds or components, nucleic acid templates, PCR reaction products, and the like. In the integrated systems it is possible to use the results of a first reaction or set of reactions to select appropriate flow conditions, reagents, reactants, products, or the like, for additional analysis. For example, the results of a first sequencing reaction can be used to select primers, templates or the like for additional sequencing, or to select related families of compounds for screening in high-throughput assay methods. These primers or templates (e.g., as components of an array) are then accessed by the system and the process continued.

In one aspect, the invention provides integrated methods of analyzing and manipulating sample materials for fluidic analysis on arrays. In the methods, an integrated microfluidic system including a microfluidic device comprising an array is provided. The device has at least a first reaction channel and at least a first reagent introduction channel, typically etched, machined, printed, or otherwise manufactured in or on a substrate. Optionally, the device can have a second reaction channel and/or reagent introduction channel, a third reaction channel and/or reagent introduction channel or the like, up to and including hundreds or even thousands of reaction and/or reagent introduction channels. The reaction channel and reagent introduction channels are in fluid communication, i.e., fluid can flow between the channels under selected conditions. The device has a material transport system for controllably transporting a material through and among the reagent introduction channel and reaction channel and for positioning array components. For example, the material transport system can include electrokinetic, electroosmotic, electrophoretic or other fluid manipulation aspects (micropumps and microvalves, fluid switches, fluid gates, etc.) which permit controlled movement and mixing of fluids and movement of array members. The device also has a fluidic interface in fluid communication with the reagent introduction channel. Such fluidic interfaces optionally include capillaries, channels, pins, pipettors, electropipettors, or the like, for moving fluids, and optionally further include microscopic, spectroscopic, fluid separatory or other aspects. The fluidic interface samples a plurality of reagents or mixtures of reagents from a plurality of sources of reagents or mixtures of reagents and introduces the reagents or mixtures of reagents into the reagent introduction channel. Essentially any number of reagents or reagent mixtures and or array members can be introduced by the fluidic interface, depending on the desired application. Because microfluidic manipulations are performed in a partially or fully sealed environment, contamination and fluidic evaporation in the systems are minimized.

In the methods, a first reagent from the plurality of sources of reagent or mixtures of reagents is selected. A first sample material and the first reagent or mixture of reagents is introduced into the first reaction channel, whereupon the first sample material and the first reagent or mixture of reagents react. Typically, one of the first sample material or first reagent or reagent mixture are bound to a microparticle in an array. This reaction can take a variety of different forms depending on the nature of the reagents. For example, where the reagents bind to one another, such as where the reagents are an antibody or cell receptor and a ligand, or an amino acid and a binding ligand, the reaction results in a bound component such as a bound ligand (e.g., bound to an array member). Where the reagents are sequencing reagents, a primer extension product results from the reaction. Where the reagents include enzymes and enzyme substrates, a modified form of the substrate typically results. Where two reacting chemical reagents are mixed, a third product chemical typically results.

In the methods, a reaction product of the first sample material and the first reagent or mixture of reagents is analyzed in the context of an array. This analysis can take any of a variety of forms, depending on the application. For example, where the product is a primer extension product, the analysis can take the form of separating reactants by size, or by location on the array and detecting the sized reactants and translating the resulting information to give the sequence of a template nucleic acid. Similarly, because microscale fluidic devices of the invention are optionally suitable for heating and cooling a reaction, a PCR reaction utilizing PCR reagents (thermostable polymerase, nucleotides, templates, primers, buffers and the like) can be performed and the PCR reagents detected. Where the reaction results in the formation of a new product, such as an enzyme-substrate product, a chemical species, or an immunological component such as a bound ligand, the product is typically detected by any of a variety of detection techniques, including fluorescence, autoradiography, microscopy, spectroscopy, or the like.

Based upon the reaction product, a second reagent or mixture of reagents is selected and a second sample material is assessed, optionally following manipulation of particle sets to modify flow conditions. For example, where the product is a DNA sequence, a sequencing primer and/or template for extension of available sequence information is selected. Where the product is a new product such as those above, an appropriate second component such as an enzyme, ligand, antibody, receptor molecule, chemical, or the like, is selected to further test the binding or reactive characteristics of an analyzed material. The second reagent or mixture of reagents is introduced into the first reaction channel, or optionally into a second (or third or fourth . . . or nth) reaction channel in the microfluidic device. The second sample material and the second reagent or mixture of reagents react, forming a new product, which is analyzed as above. The results of the analysis can serve as the basis for the selection and analysis of additional reactants and additional flow conditions for similar subsequent analysis. The second sample material, reagents, or mixtures of reagents can comprise the same or different materials. For example, a single type of DNA template is optionally sequenced in several serial reactions. Alternatively, completing a first sequencing reaction, as outlined above, serves as the basis for selecting additional templates (e.g., overlapping clones, PCR amplicons, or the like).

Accordingly, in a preferred aspect, the invention provides methods of sequencing a nucleic acid by an iterative process on an array. For example, in one typical method, the biochemical components of a sequencing reaction (e.g., a target nucleic acid, a first and optionally, second sequencing primer, a polymerase (optionally including thermostable polymerases for use in PCR), dNTPs, and ddNTPs) are mixed in a microfluidic device in contact with one or more array member under conditions permitting target dependent polymerization of the dNTPs. Polymerization products are optionally separated in the microfluidic device to provide a sequence of the target nucleic acid, or as in the case of pyrophosphate methods described above, can be read directly from the array, depending on the position of components in the array (similarly, sequencing by hybridization methods do not require separation of products, with results being determined by position on an array). Typically, sequencing information acquired by this method is used to select additional sequencing primers and/or templates or probes, and the process is reiterated, optionally following movement of array components to modulate flow conditions.

In one integrated sequencing system, methods of sequencing a target nucleic acid are provided in which an integrated microfluidic system comprising a microfluidic device having an array is utilized in the sequencing method. The integrated microfluidic device has at least a first sequencing reaction channel and at least a first sequencing reagent introduction channel, the sequencing reaction channel and sequencing reagent introduction channel being in fluid communication and at least one of the channels comprising one or more array component. The integrated microfluidic system also has a material transport system for controllably transporting sequencing reagents through the sequencing reagent introduction channel and sequencing reaction channel and a fluidic interface in fluid communication with the sequencing reagent introduction channel for sampling a plurality of sequencing reagents, or mixtures of sequencing reagents, from a plurality of sources of sequencing reagents or mixtures of sequencing reagents and introducing the sequencing reagents or mixtures of sequencing reagents into the sequence reagent introduction channel. For example, the system set forth in U.S. Pat. No. 5,779,868 can be used. As discussed above, the interface optionally includes capillaries, pins, pipettors and the like. In the method, a first sequencing primer sequence complementary to a first subsequence of a first target nucleic acid sequence is introduced into the sequence reagent introduction channel. The first primer is hybridized to the first subsequence and the first primer is extended with a polymerase enzyme along the length of the target nucleic acid sequence to form a first extension product that is complementary to the first subsequence and a second subsequence of the target nucleic acid. Again, any of these components are optionally coupled to one or more array member. The sequence of the first extension product is determined and, based upon the sequence of the first extension product, a second primer sequence complementary to a second subsequence of the target nucleic acid sequence is selected, hybridized and extended as above.

In the sequence methods herein, it is sometimes advantageous to select sequencing primers from a large set of sequencing primers, rather than synthesizing primers to match a particular target nucleic acid. For example, 5 or 6-mer primers can be made to hybridize specifically to a target, e.g., where the primers are modular and hybridize to a single region of a nucleic acid. All possible 5 or 6 mers can be synthesized for selection in the methods herein, or any subset of 5 or 6 mers can also be selected. In some embodiments, the primers are transferred to the microfluidic apparatus, e.g., by a capillary, an electropipettor, or using sipping technology, from a microtiter plate or from and array of oligos. The primers are used to hybridize to bound targets fixed to array members (see also, above, under discussions of modular primer strategies). In other embodiments, the primers are located on a region of a microfluidic device, chip or other substrate.

In another, similar aspect, the devices, systems arrays and methods of the invention are useful in performing fluidic operations that require a large number of successive fluid manipulations, i.e., in performing a number of preparative and analytical reactions or operations on a given sample. By "successive fluid manipulations" is generally meant a fluidic operation that involves the successive treatment of a given fluid sample volume, i.e., combination/reaction with reactants, incubation, purification/separation, analysis of products, and the like. Where successive fluid manipulations are performed at the bench scale, e.g., the performance of numerous, different manipulations on a particular sample such as combination with reagents, incubation, separation and detection, such manipulations can also become cumbersome as the number of steps increases, as with each step, the possibility of introducing an error into the operation or experiment increases. This complexity, and the consequent increased possibility of errors increases substantially as the number of samples to be passed through the operation increases. Thus, the devices or systems of the present invention are also particularly useful in performing fluidic operations which require successive fluid manipulations of a given sample or fluid of interest, e.g., more than 2 steps or different manipulations, typically greater than 5 steps or different manipulations, preferably greater than 10 steps or different fluid manipulations. The systems are also useful and readily capable of performing fluidic operations that include greater than 20, 50, 100, 1000 steps or different fluid manipulations on a given fluid volume.

In a related, but alternate aspect, the devices, arrays, systems and methods of the invention are useful in performing fluidic operations that require a large number of parallel fluid manipulations, i.e., to screen biological samples, screen test compounds for drug discovery, e.g., as set forth in WO/98/00705 and WO 98/00231 and incorporated herein by reference. To carry out these operations, a substrate will typically employ parallel channels and/or channel networks, interconnected by one or more common channels, with at least one particle array dispersed within the device. Fluids required for the subject reaction, e.g., samples or reagents, are directed along one or more of the common channels, and are delivered to each of the parallel channels.

As used herein, "parallel fluid manipulations" means the substantially concurrent movement and/or direction, incubation/reaction, separation or detection of discrete fluid volumes to a plurality of parallel channels and/or channel networks, or chambers of a microfluidic device, i.e., greater than about 10 distinct parallel channels or chambers, typically greater than 20 distinct channels or chambers, preferably greater than about 50 distinct channels or chambers, and often greater than about 100 distinct channels or chambers. As used herein, the term "parallel" refers to the ability to concomitantly or substantially concurrently process two or more separate fluid volumes, and does not necessarily denote a specific channel or chamber structure or layout.

Ultra high-throughput analysis systems are provided, for example for performing nucleic acids-based diagnostic and sequencing applications, e.g., in a reference laboratory setting. The system typically has several components: a specimen and reagents handling system; an "operating system" for processing integrated microchip experimentation steps; application-specific analysis devices; a signal detection system, and multiple software components that allow the user to interact with the system, and run processing steps, interpret data, and report results.

Integrated Systems for Assay Normalization

One similar application of the integrated systems and arrays of the invention is the titration of assay components into the dynamic range of an assay. For example, an assay can first be performed where one or more components of the assay are not within the range necessary for adequate performance of the assay, e.g., if the assay is performed using a concentration which is too high or too low for some components, the assay may not provide quantitative results. This need to titrate assay components into the dynamic range of an assay typically occurs where one or more component of the assay is present at an unknown activity or concentration. Ordinarily, the assay must be run at several concentrations of components, i.e., the assay is run a first time, components are diluted, the assay is run a second time, etc. until the assay can be performed within the dynamic range of the assay. It will be appreciated that this iterative approach can involve several unknown concentrations simultaneously, requiring considerable trial and error.

In the integrated array systems of the invention, an assay can be performed at as many concentrations of components as necessary to titrate the assay components into the dynamic range of the assay, with the results of each assay being used to optimize additional assay points. Similarly, titration curves, which are often the result of multiple assay runs with different component concentrations are determined by performing repeated assays with different concentrations of components. Different concentrations of assay components in separate assays can be monitored serially or in parallel. In brief, one simply runs the assay at one or more array location, detecting the results. If assays are simultaneously (or even separately) run at additional array locations with known components, it is possible to use these known components as normalization elements for the array and the assay. Thus, arrays can include positive or negative control elements (reagents, templates, etc.), calibration components (e.g., an array can include a labeled array member and an unlabeled array member for calibration purposes, or even include members comprising gradations of label intensity).

For example, in one aspect, the invention comprises any of "blank," "dummy," "calibration," "control," "positive control," "negative control," "sample," "test" or "tracking" particles, e.g., interspersed with each other or with other elements of an array. Blank particles are particles which do not comprise a label. Dummy particles are either blank, or comprise a known signal component. Calibration particles comprise a selected quantity of labeled component, or of a component to be labeled. For example, calibration particles (or any of the other particles herein) can comprise one or more quantum dot (Warren and Nie (1998) Science, 281: 2016-2018). Control particles comprise one or more selected known element. Positive control particles comprise a known component which, if the assay or other use for the array member is working properly, will result in accumulation or display of a detectable signal. Conversely, a negative control particle is a particle that, if the assay or other use for the array member is working properly will not result in a significant accumulation, release or display of a detectable signal. A "sample" particle comprises an assay or reaction element of interest. A "test" particle is a particle that comprises an unknown element to be tested, or which interacts with such an element in an assay or reaction, depending on the specified context of the invention. A "tracking" particle is a particle which displays a detectable signal, or which displays a known absence of signal within a labeled array, and which is used to track the position of array elements.

It will be appreciated that many useful particle types will meet more than one of the above criteria. For example a negative control particle can also be a blank, a tracking element, or the like. Furthermore, the particles can be placed in any selected relative positional conformation. For example, blank particles can be interspersed with different sample particles to maintain separation and prevent contamination between the different sample sets. Calibration particles can be interspersed with sample particles in any manner to provide signals for calibration of assays, reactions, etc. Many such variations will be apparent upon review.

The ability to titrate and optimize assays is useful for diagnostic assays, for determining concentrations or activities of selected components in a system (proteins, enzymes, nucleic acids, small molecules, etc.). Furthermore, the present integrated systems provide for rational selection of assay conditions as data is acquired. For example, in one embodiment, a diagnostic assay needs to be performed using several components which are present at initially unknown concentrations or activities. A first series of concentration or activity assays is performed on the array to determine the activity or concentration of particular components, e.g., enzyme, protein, inhibitor, co-factor, nucleic acid, or the like. After these assays are performed and the concentrations or activities of some or all of the components for the diagnostic assay are determined, the integrated system selects appropriate amounts of the assay components, performs any necessary dilutions, combines the assay components and performs the diagnostic assay. Similarly, further data points can be collected by adjusting the concentrations or amounts of diagnostic assay components and re-running the assay. All of the fluid manipulations can be performed rapidly and the integrated system is able to assess and compile the results of individual data points or individual assays to select which additional assays need to be performed for assay verification.

In its most basic form, assay optimization involves the identification of factors affecting a reaction result, followed by the systematic variation of each of these variables until optimal reaction conditions are identified. This is generally termed an "OFAT" method for "one factor at a time." Thus, assuming a simple two reagent reaction, one would first identify the factors affecting the outcome, e.g., concentration of reagent A, concentration of reagent B and, e.g., temperature. One would then run the assay where one factor was varied while the others remained constant. For example, one would perform the same reaction at numerous different concentrations of reagent A, while maintaining the concentration of reagent B and the temperature. Next, reagent B would be varied while reagent A and temperature remained constant, and finally, the temperature would be varied.

Even in this simplest form, the number and complexity of necessary reactions is apparent. When one considers that most reactions will have far more than three variables, and that these variable will not be independent of each other, the possibility of manually performing these assays, or even performing them in currently available automated formats becomes a daunting prospect. For example, while robotic systems using microwell plates can perform large numbers of manipulations to optimize assay parameters, such systems are very expensive. Further, as these systems are typically limited to the bench scale volumes described above, they require large volumes of reagents and large amounts of space in which to operate.

In contrast, the devices, systems and methods of the present invention permit the optimization of large numbers of different assays, by providing an extremely low volume, automatable and sealed format in which such optimization can occur rapidly and automatically. For example, the devices can run a first fluidic operation by combining a preselected volume of a first reactant with a preselected volume of a second reactant, at a desired or preselected temperature for a desired or preselected amount of time. The device then repeats the assay, but varies at least one of the volume of the first or second reactants, the temperature, or the amount of time allowed for the reaction. This is repeated until a desired number of varied reactions are performed, i.e., generating sufficient data to permit an estimation of optimal assay conditions which will produce an optimal result of the reaction, within a desired range of statistical significance. "optimal assay conditions" include those conditions that are required to achieve the desired result of the reaction. Such desired results can include maximization of reaction yields, but also includes assay conditions which are optimized for sensitivity to one variable, e.g., inhibitor concentration, and the like.

Drug Screening Assays

In addition to sequencing, the integrated microfluidic systems and arrays of the invention are broadly useful in a variety of screening assays where the results of mixing one or more components are to be determined, and particularly, where the results determined are used to select additional reagents to be screened.

As described more fully below, the integrated microfluidic system of the invention can include a very wide variety of storage elements for storing reagents to be assessed. These include well plates, matrices, membranes and the like. The reagents are stored in liquids (e.g., in a well on a microtiter plate), or in lyophilized form (e.g., dried on a membrane), and can be transported to an array component of the microfluidic device using conventional robotics, or using an electropipettor as described below.

Because of the breadth of the available sample storage formats for use with the present invention, virtually any set of reagents can be sampled and assayed in an integrated system of the present invention. For example, enzymes and substrates, receptors and ligands, antibodies and ligands, proteins and inhibitors, cells and growth factors or inhibitors, viruses and virus binding components (antibodies, proteins, chemicals, etc.) immunochemicals and immunoglobulins, nucleic acids and nucleic acid binding chemicals, proteins, or the like, reactant chemicals (acids, bases, organic molecules, hydrocarbons, silicates, etc.) can all be assayed using the integrated systems of the invention. For example, where a molecule which binds a protein is desired, potential binding moieties (chemicals, peptides, nucleic acids, lipids, etc.) are sequentially mixed with the protein in a reaction channel, and binding is measured (e.g., by change in electrophoretic mobility, quenching of fluorescent protein residues, or the like). Thousands of compounds are easily screened using this method, in a short period of time (e.g., less than an hour).

An advantage of the integrated nature of the present system is that it provides for rational selection of structurally or functionally homologous compounds or components as the assay progresses. For example, where one compound is found to have binding activity in an array based assay, the selection of a second compound to be tested can be performed based upon structural similarity to the first active compound. Similarly, where a compound is shown to have activity in a cell (e.g., up-regulation of a gene of interest) a second compound affecting the same cellular pathway (e.g., calcium or inositol phosphate second messenger systems, etc.) can be selected from the group of available compounds for testing. In this way, it is possible to focus screening assays from purely random at the outset to increasingly focused on likely candidate compounds as the assays progress.

Integrated Microfluidic Array Systems

Device Integration

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquoting, and the like. Similarly, downstream operations may include similar operations, including, e.g., separation of sample components, labeling of components, assays and detection operations, electrokinetic or pressure-based injection of components into contact with particle sets, or materials released from particle sets, or the like.

Assay and detection operations include, without limitation, probe interrogation assays, e.g., nucleic acid hybridization assays utilizing individual probes, free or tethered within the channels or chambers of the device and/or probe arrays having large numbers of different, discretely positioned probes, receptor/ligand assays, immunoassays, and the like. Any of these elements can be fixed to array members, or fixed, e.g., to channel walls, or the like.

Loading of Array Components and Reagents

Array members and reagents can be loaded into microfluidic structures, e.g., by placing the reagent or array member in a well fluidly coupled to a microfluidic channel network. The reagent or array member is then flowed through the microchannel network as described supra, e.g., by pressure (positive or negative) or by electrokinesis, or by moving a magnetic field relative to the array member (i.e., where the array member is magnetic).

Alternatively, array or particle members can be stored external to the microfluidic system in a system of wells, plates, or even as dried components stored on a surface. Thus, the integrated systems of the invention optionally include such external storage elements. In one aspect, the present invention includes a microwell plate (e.g., a 96, 384 or more well plate) having array members stored within wells of the plate.

To introduce array members or reagents into the microfluidic system, either pressure-based, electrokinetic or centrifugal approaches can be used. For example, electropipettors (which can include one or multiple "sipper" channels) can be used to access wells, plates or to re-hydrate soluble or suspendable dried components from dry storage media. A variety of access systems for coupling reagent storage and microfluidic systems are described in Knapp et al. "Closed Loop Biochemical Analyzers" WO 98/45481. As applied to the present invention, these coupling devices and strategies are also used for flowing particle sets into microfluidic systems.

Instrumentation

In the present invention, the materials in the arrays are optionally monitored and/or detected so that velocity can be determined. From velocity measurements, decisions are then made regarding subsequent fluidic operations.

The systems described herein generally include microfluidic devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Controllers

A variety of controlling instrumentation is optionally utilized in conjunction with the microfluidic devices described above, for controlling the transport and direction of fluids and/or materials within the devices of the present invention, e.g., by pressure-based or electrokinetic control.

For example, in many cases, fluid transport and direction are controlled in whole or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357. In such systems, fluid direction is often accomplished through the incorporation of microfabricated valves, which restrict fluid flow in a controllable manner. See, e.g., U.S. Pat. No. 5,171,132.

As noted above, the systems described herein can also utilize electrokinetic material direction and transport systems. As such, the controller systems for use in conjunction with the microfluidic devices typically include an electrical power supply and circuitry for concurrently delivering appropriate voltages to a plurality of electrodes that are placed in electrical contact with the fluids contained within the microfluidic devices. Examples of particularly preferred electrical controllers include those described in, e.g., published PCT application WO 98/00707 and in U.S. Pat. No. 5,800,690. In brief, the controller uses electric current control in the microfluidic system. The electrical current flow at a given electrode is directly related to the ionic flow along the channel(s) connecting the reservoir in which the electrode is placed. This is in contrast to the requirement of determining voltages at various nodes along the channel in a voltage control system. Thus the voltages at the electrodes of the microfluidic system are set responsive to the electric currents flowing through the various electrodes of the system. This current control is less susceptible to dimensional variations in the process of creating the microfluidic system in the device itself. Current control permits far easier operations for pumping, valving, dispensing, mixing and concentrating subject materials and buffer fluids in a complex microfluidic system. Current control is also preferred for moderating temperature effects (e.g., joule heating) within the channels.

The present invention also provides novel methods of controlling fluid flow, particle flow, or the like in microfluidic channels. By flowing reagents, samples, and/or particle arrays through a microfluidic network using a system of split wells, contamination by components of previous reactions is avoided. In an assay involving many components, the components typically vary in charge. Therefore when transporting materials using electrokinetic techniques, components may move in different directions depending on their charge, especially in buffers in which the electroosmotic mobility is low. Therefore, a sample introduction step may not properly introduce all components to the reaction area and a washing step may not clear away all reaction components to the waste reservoir(s) before the next reaction or phase. Therefore, some components may carry over from a first reaction to a second reaction in a sequential system, e.g., a high throughput system.

For example, in a pyrosequencing reaction in which the DNA template is immobilized on beads, all sequencing reagents are optionally present in a reaction mixture along with reagents used to transform any generated pyrophosphate into chemiluminescence. The DNA sequencing reagents, e.g., dNTPs, and the pyrophosphate are negatively charged, but some enzymes can be positively charged. The present system clears away both positively and negatively charged components before the next base extension reaction begins, thus avoiding contamination between samples.

To provide more complete washing of oppositely charged components, e.g., from a microfluidic system, a pair of wells is provided on each side of a reaction region. Reactions of interest, e.g., pyrosequencing, occur, e.g., in a network of microscale channels or capillaries, in the reaction area. One well of each pair is used as a waste well and the other is used as a reagent source or reservoir, e.g., for reagents of a certain charge. For example, see FIG. 18, Panel A. Well 1810 comprises a source of positive and neutral reagents and well 1830 comprises a source for negative reagents (or those reagents whose total electrokinetic mobility is negative). Wells 1820 and 1840 comprise waste wells. Reagents are optionally loaded into the microfluidic system, e.g., reaction area 1850, by applying a positive voltage to well 1810 relative to well 1830. Substantially zero current is applied at wells 1820 and 1840. All reagents are loaded simultaneously using this method. Positive and neutral reagents flow from well 1810 to the reaction area 1850 and negative reagents flow from well 1830 to reaction area 1850. Typically, the reagents are loaded quickly to avoid generation of reaction products during loading. Alternatively, the positive and/or neutral reagents are loaded separately from the negative reagents. Positive and neutral reagents only are loaded by applying a positive voltage at well 1810 relative to well 1840 and substantially zero current at wells 1830 and 1820. The negative reagents alone are loaded by applying a positive voltage at well 1820 relative to well 1830 and substantially zero current at wells 1840 and 1810. Reagents are removed from reaction area 1850 in a similar manner. A positive voltage is applied to well 1820 relative to well 1840 and substantially zero voltage at wells 1810 and 1830. This step does not use either of the reagent wells, 1810 and 1830, thereby preventing contamination as reagents are removed or rinsed from the device.

Figure 18A:
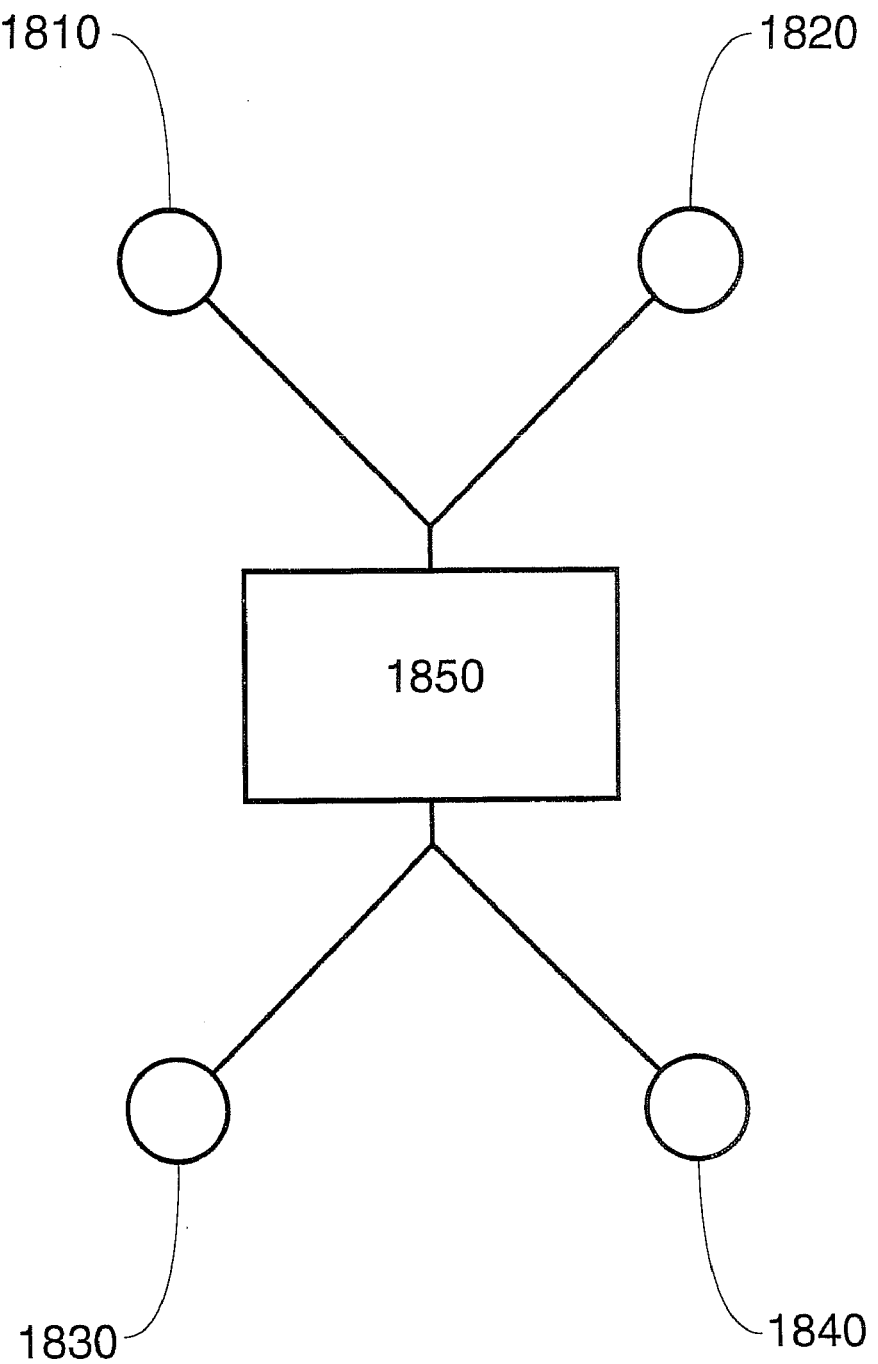
FIG. 18, panels A, B, and C, provides schematic views of example microfluidic devices useful in split well loading and unloading, e.g., of reagents and particles, e.g., to avoid contamination.
Figure 18B:
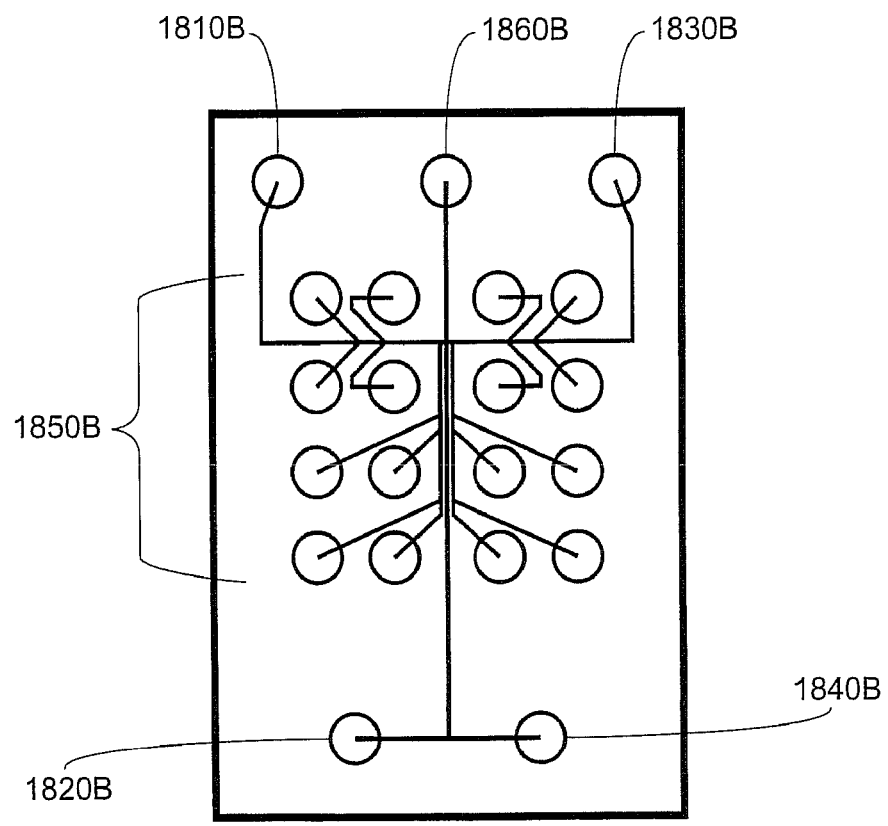
Figure 18C:
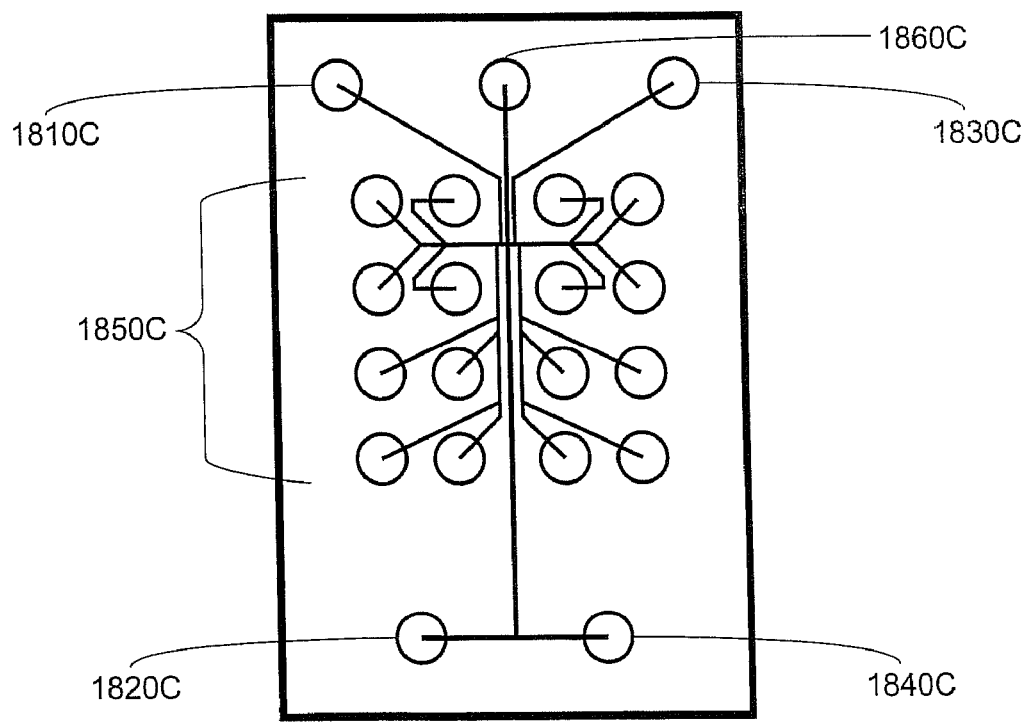

Alternative channel configurations are provided in FIG. 18, panels B and C. Reaction areas 1850b and 1850c illustrate possible channel configurations. Other configurations as described herein are also optionally used. Wells 1810b and 1810c are optionally used for positive and/or neutral reagents and wells 1830b and 1830c optionally comprise negative reagents. Introduction of reagents optionally comprises applying a positive voltage at well 1810b or 1810c relative to 1830b or 1830c. Alternatively, a positive voltage is applied at well 1810b or 1810c relative to one or more of wells 1860b, 1860c, 1820b, 1820c, 1840b, and 1840c. Negative reagents are optionally introduced by applying a positive voltage at any of wells 1860b, 1860c, 1820b, 1820c, 1840b, and 1840c relative to well 1830b or 1830c. Removal of reagents is achieved, e.g., by applying a positive voltage at 1860b or 1860c relative to 1840b or 1840c. Other possible methods of flowing reagents through the devices of FIG. 18 will be readily apparent upon further review.

Typically, the controller systems are appropriately configured to receive a microfluidic device as described herein. In particular, the controller and/or detector (as described in greater detail, below), includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also used to provide for electrokinetic injection or withdrawal of material downstream of the region of interest to control an upstream flow rate. The same instrumentation and techniques described above are also utilized to inject a fluid into a downstream port to function as a flow control element.

Detector

The devices herein optionally include signal detectors, e.g., which detect fluorescence, phosphorescence, radioactivity, pH, charge, absorbance, luminescence, temperature, magnetism or the like. The detectors optionally monitor a plurality of signals from the plurality of particle sets, either simultaneously or sequentially. For example, the detector can monitor a plurality of optical signals which correspond in position to sets of particles within the array. Example detectors include of photo multiplier tubes, a CCD array, a scanning detector or galvo-scann or the like. Particles from the array which emit a detectable signal can be flowed past the detector, or, alternatively, the detector can move relative to the array to determine particle position (or, preferably, the detector can simultaneously monitor a number of spatial positions corresponding to array members, e.g., as in a CCD array). The detector can include or be operably linked to a computer, e.g., which has software for converting detector signal information into nucleic acid sequence information, converting detector signal information into reaction kinetic information, converting signal information into antibody binding data, converting signal information into cell receptor binding data converting signal information into hybridization data, or the like.

Signals from arrays are optionally calibrated, e.g., by calibrating the microfluidic system by monitoring a signal from a known member of the array, e.g., a calibration or marker particle, or from a known particle set external to the array. Similarly the relative positions of particle sets and signals from the array is monitored, e.g., by determining the position of one or more members of the array by monitoring a signal from a known member of the array, thereby determining the position of the known member of the array.

In the microfluidic systems described herein, a variety of detection methods and systems are employed, depending upon the specific operation that is being performed by the system. A microfluidic system can also employ multiple different detection systems for monitoring the output of the system. Detection systems of the present invention are used to detect and monitor the materials in the detection window. Once detected, the flow rate and velocity of particles in the channels is optionally measured and controlled as described above.

Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials, the detector will typically include a light source which produces light at an appropriate wavelength for activating the fluorescent material, as well as optics for directing the light source through the detection window to the material contained in the channel or chamber. The light source can be any number of light sources that provides an appropriate wavelength, including lasers, laser diodes and LEDs. Other light sources required for other detection systems. For example, broad band light sources are typically used in light scattering/transmissivity detection schemes, and the like. Typically, light selection parameters are well known to those of skill in the art.

The detector can exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

Computer

As noted above, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring of materials in the channels, so that flow rate and velocity may be determined. Additionally the software is optionally used to control electrokinetic injection or withdrawal of material. The electrokinetic or withdrawal is used to modulate the flow rate as described above.

Kits

Generally, the microfluidic devices described herein are packaged to include many if not all of the necessary reagents for performing the device's preferred function. For example, the kits can include any of microfluidic devices comprising arrays, particle array members, reagents (e.g., sequencing or PCR reagents), sample materials, control materials, or the like. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (of course, in one preferred embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

The discussion above is generally applicable to the aspects and embodiments of the invention described below.

Moreover, modifications can be made to the method and apparatus described herein without departing from the spirit and scope of the invention as claimed, and the invention can be put to a number of different uses including the following:

The use of a microfluidic system containing at least a first substrate and having a first channel and a second channel intersecting the first channel, at least one of the channels having at least one cross-sectional dimension in a range from 0.1 to 500 µm, in order to test the effect of each of a plurality of test compounds on a biochemical system, the system including an array.

The use of a microfluidic system as described herein, wherein a biochemical system flows through one of said channels substantially continuously, providing for, e.g., sequential testing of a plurality of test compounds.

The use of an array in a microfluidic device as described herein to modulate reactions within microchannels or microchambers.

The use of electrokinetic injection in a microfluidic device as described herein to modulate or achieve flow in the channels.

The use of a combination of wicks, electrokinetic injection and pressure based flow elements in a microfluidic device as described herein to modulate or achieve flow of materials to arrays, or array members to materials, e.g., in the channels of the device.

The use of split waste wells or split reagent wells to load or unload reagents from a microfluidic device as described herein.

An assay utilizing a use of any one of the microfluidic systems or substrates described herein.

Microfluidic devices and bioassays which can be adapted to the present invention by the addition of arrays include various PCT applications and issued U.S. patents, such as, U.S. Pat. No. 5,699,157 (J. Wallace Parce) issued Dec. 16, 1997, U.S. Pat. No. 5,779,868 (J. Wallace Parce et al.) issued Jul. 14, 1998, U.S. Pat. No. 5,800,690 (Calvin Y. H. Chow et al.) issued Sep. 1, 1998, and U.S. Pat. No. 5,842,787 (Anne R. Kopf-Sill et al.) issued Dec. 1, 1998; and published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548, which are all incorporated herein by reference.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were so individually denoted.

What is claimed is:

1. A method of performing a plurality of chemical reactions in a microfluidic device, the method comprising:
   providing a microfluidic device comprising an interior cavity, the cavity comprising a main channel and first and second side channels, the first and second side channels intersecting the main channel, thereby forming first and second channel intersections, the cavity further comprising first and second wells, the first well being in fluid communication with the first side channel and the second well being in fluid communication with the second side channel;
   providing a mobile ordered array comprising first, second, and third sets of particles within the main channel of the interior cavity;
   providing first and second liquid reagents within the interior cavity, the first liquid reagent being disposed within the first well and the second liquid reagent being disposed within the second well;
   transporting the first set of particles as the mobile ordered array through the main channel into the first channel intersection by fluid pressure;
   flowing the first liquid reagent from the first well through the first side channel into the first channel intersection, wherein the first liquid reagent contacts the first set of particles in the main channel, thereby providing a first chemical reaction in the microfluidic device;
   transporting the first set of particles as the mobile ordered array through the main channel into the second channel intersection; and
   flowing the second liquid reagent from the second well through the second side channel into the second channel intersection, wherein the second liquid reagent contacts the first set of particles in the main channel, thereby providing a second chemical reaction in the microfluidic device;
   wherein the particles are beads.

2. The method of claim 1, the method further comprising:
   transporting the second set of particles through the main channel into the first channel intersection; and
   flowing the first liquid reagent through the first side channel into the first channel intersection, wherein the first reagent contacts the second set of particles in the main channel.

3. The method of claim 1, the method further comprising detecting a signal resulting from contact of the first set of particles by one of the first and the second liquid reagents.

4. The method of claim 1, the method further comprising detecting a plurality of signals resulting from contact of the first set of particles by the first and the second liquid reagents.

5. The method of claim 2, the method further comprising detecting a plurality of signals resulting from contact of the first and second sets of particles by the first liquid reagent.

6. The method of claim 5, wherein detecting a plurality of signals resulting from contact of the first and second sets of particles by the first liquid reagent comprises detecting simultaneous or sequential signal emissions from the first and second sets of particles.

7. The method of claim 1, wherein at least one of the first and second liquid reagents is a nucleic acid sequencing reagent selected from the group consisting of a liquid solution comprising a nucleotide, a liquid solution comprising a polymerase, a liquid solution comprising a dNTP or ddNTP, a liquid solution comprising a fluorescently labeled nucleotide, a liquid solution comprising a nucleotide analog, a liquid solution comprising a sufurylase, a liquid solution comprising an apyrase, a liquid solution comprising inorganic phosphate, a liquid solution comprising ATP, a liquid solution comprising a thermostable polymerase, a liquid solution comprising an endonuclease, a liquid solution comprising an exonuclease, a liquid solution comprising Mg++, a liquid solution comprising a molecular crowding agent, a liquid solution comprising a buffer, a liquid solution comprising an intercalating dye, a liquid solution comprising a reducing agent, a liquid solution comprising a phosphatase or an enzyme with phosphatase activity, a liquid solution comprising a salt, and combinations thereof.

8. The method of claim 1, wherein at least one of the first and second liquid reagents is a binding reagent selected from the group consisting of a first nucleic acid that is fully or partially complementary to a second nucleic acid complexed with at least one of the first and second particle sets, a first protein that specifically binds to one or more component of at least one of the first and second particle sets, a first antibody that specifically binds to one or more component of at least one of the first and second particle sets, a binding buffer, a blocking reagent, an immunoassay reagent, a labeled probe nucleic acid, and combinations thereof; and wherein the method further comprises flowing the at least one of the first and second liquid reagents into contact with at least one of the first and second sets of particles and detecting resulting binding of the liquid reagent to the at least one of the first and second sets of particles.

9. The method of claim 1, wherein at least one of the first and second sets of particles comprises at least one set of nucleic acid templates and at least one set of nucleic acid primers, wherein at least one of the first and second liquid reagents comprises one or more nucleotide analogs, and wherein at least one of the first and the second chemical reactions comprises adding at least one of the one or more nucleotide analogs to at least one member of the set of primers.

10. The method of claim 9, wherein the one or more nucleotide analogs comprise reversible chain-terminating nucleotide analogs.

11. The method of claim 10, wherein the reversible chain-terminating nucleotide analogs comprise a compound having formula (I) or formula (II), and wherein B comprises a nitrogenous base and $R^4$ comprises a label moiety:

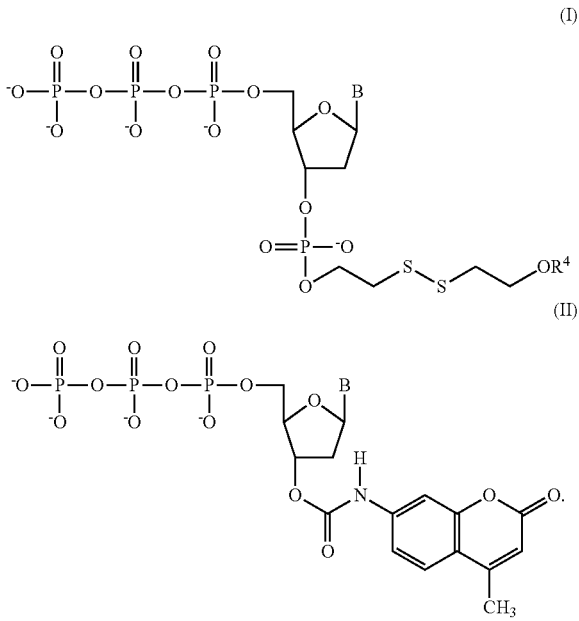

12. The method of claim 1, wherein at least one of the first and second sets of particles comprises at least one set of nucleic acid templates and at least one set of nucleic acid primers, wherein at least one of the liquid reagents comprises one or more nucleotides, and wherein at least one of the first and second chemical reactions results in a double-stranded nucleic acid region, the method further comprising flowing an intercalating dye into contact with the double-stranded nucleic acid region, which intercalating dye intercalates into the double-stranded region.

13. The method of claim 1, further comprising adding an intercalating dye to a nucleic acid complementary to a template molecule bound to one or more of the first and second sets of particles, the method further comprising detecting the intercalating dye.

14. The method of claim 1, the cavity further comprising third and fourth side channels, the third and fourth side channels intersecting the main channel, thereby forming third and fourth channel intersections, the method further comprising:
providing third and fourth liquid reagents, wherein each of the first, second, third, and fourth liquid reagents comprises one of A, G, C, or T nucleotides;
transporting the first set of particles through each of the third and fourth channel intersections;
flowing the third reagent through the third side channel into the third channel intersection; and
flowing the fourth reagent through the fourth side channel into the fourth channel intersection,
wherein each of the third and fourth liquid reagents contacts the first set of particles in the main channel.

15. The method of claim 2, the cavity further comprising third and fourth side channels, the third and fourth side channels intersecting the main channel, thereby forming third and fourth channel intersections, the method further comprising:
providing third and fourth liquid reagents, wherein each of the first, second, third, and fourth liquid reagents comprises one of A, G, C, or T nucleotides;
transporting the second set of particles through each of the second, third, and fourth channel intersections;
flowing the second reagent through the second side channel into the third channel intersection;
flowing the third reagent through the third side channel into the third channel intersection; and
flowing the fourth reagent through the fourth side channel into the fourth channel intersection,
wherein each of the second, third, and fourth liquid reagents contacts the second set of particles in the main channel.

16. The method of claim 1, further comprising sequencing by synthesis, the sequencing by synthesis method comprising addition of an intercalating dye to a nucleic acid complementary to a template molecule bound to a member of the mobile ordered array, the method further comprising detecting the intercalating dye.

17. The method of claim 1, further comprising sequencing by synthesis, the method comprising addition of a chain terminator to a nucleic acid complementary to a template molecule bound to a member of the mobile ordered array, the chain terminator comprising a label.

18. The method of claim 1, further comprising sequencing by synthesis, the method comprising addition of a reversible chain terminator to a nucleic acid complementary to a template molecule bound to a member of the mobile ordered array, the reversible chain terminator comprising a label, and the method further comprising cleavage of the reversible chain terminator.

* * * * *